(12) United States Patent
Nakayama et al.

(10) Patent No.: US 8,362,169 B2
(45) Date of Patent: Jan. 29, 2013

(54) ACRYLATE ESTER DERIVATIVES AND POLYMER COMPOUNDS

(75) Inventors: Osamu Nakayama, Niigata (JP); Takashi Fukumoto, Niigata (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 2 days.

(21) Appl. No.: 12/918,689

(22) PCT Filed: Feb. 20, 2009

(86) PCT No.: PCT/JP2009/052979
§ 371 (c)(1),
(2), (4) Date: Nov. 12, 2010

(87) PCT Pub. No.: WO2009/104722
PCT Pub. Date: Aug. 27, 2009

(65) Prior Publication Data
US 2011/0060112 A1    Mar. 10, 2011

(30) Foreign Application Priority Data

Feb. 22, 2008  (JP) ................................. 2008-041009

(51) Int. Cl.
C08F 228/06 (2006.01)
C08F 224/00 (2006.01)
C07D 327/02 (2006.01)
C07D 327/06 (2006.01)
C07D 319/12 (2006.01)
C07D 323/00 (2006.01)

(52) U.S. Cl. ............ 526/266; 526/257; 549/10; 549/14; 549/347; 549/378

(58) Field of Classification Search .................. 526/257, 526/266; 549/10, 14, 347, 378
See application file for complete search history.

(56) References Cited

U.S. PATENT DOCUMENTS

| 4,908,381 | A | 3/1990 | Greenwald et al. |
| 5,072,029 | A | 12/1991 | Hertler |
| 2007/0269741 | A1 | 11/2007 | Iijima et al. |

FOREIGN PATENT DOCUMENTS

| JP | 2 59570 | 2/1990 |
| JP | 2 231482 | 9/1990 |
| JP | 5 88367 | 4/1993 |
| JP | 7 295221 | 11/1995 |
| JP | 9 73173 | 3/1997 |
| JP | 2000 154169 | 6/2000 |
| JP | 2003 246825 | 9/2003 |
| JP | 2007 308586 | 11/2007 |
| JP | 2008 138073 | 6/2008 |
| WO | 91 15453 | 10/1991 |
| WO | 2007 094474 | 8/2007 |

OTHER PUBLICATIONS

STN structure search results (Apr. 26, 2012).*
Machine translation of JP 07-295221 A (Nov. 10, 1995).*
Satoshi Takechi, et al., "Impact of 2-Methyl-2-Adamantyl Group Used for 193-nm Single-Layer Resist", Journal of Photopolymer Science and Technology, vol. 9, No. 3, 1996, pp. 475-487.
International Technology Roadmap for Semiconductors, "Lithography", Update version, 2006, 20 pages.
Antolini, L., et al., "The Reaction of the Acetates of α-Chloro Methyl Hemiacetals with Nucleophiles. Synthesis of 2-Hydroxy-1, 4-Dithianes," Gazzetta Chimica Italiana, vol. 127, pp. 11-17, (1997).
Brimfield, A.A., et al., "Thiodiglycol, the hydrolysis product of sulfur mustard: Analysis of in vitro biotransformation by mammalian alcohol dehydrogenases using nuclear magnetic resonance," Toxicology and Applied Pharmacology, vol. 213, pp. 207-215, (2006).
Szarek, W.A., et al., "Synthesis and biological activity of nucleoside analogs involving modifications in the carbohydrate ring," Can. J. Chem., vol. 63, p. 2149-2161, (1985).
Herzig, C., et al., "2-Chloroxirane als Synthone zur Darstellung sechsgliedriger Heterocyclen," Chem. Ber., vol. 114, pp. 2348-2354, (1981).
Bulman-Page, P.C., et al., "On the Reaction of Thioacetals with Sulphuryl Chloride," Journal of Chemical Society, Perkin Transactions 1: Organic and Bio-Organic Chemistry, No. 2, pp. 457-461, (1981).
Frieze, D.M., et al., "Structural studies of organosulfur compounds. 3. Stereochemistry and conformational distortions in trans-hexahydro-1, 4-benzoxathiane S-oxides," J. Org. Chem., vol. 42, No. 13, pp. 2208-2211, (1977).
Schubert, H., et al., "On the Reactions of 2-hydroxy-1, 4-oxathianes," Z. Chem., vol. 16, No. 4, pp. 147-148, (1976).
Buck, K.W., et al., "Derivatives of 2-hydroxy-1, 4-Oxathiane and 2-Hydroxymorpholine. A New Class of Sugar," Carbohydrate Research, vol. 2, pp. 14-23, (1966).
International Search Report issued May 26, 2009 in PCT/JP09/052979 filed Feb. 20, 2009.
U.S. Appl. No. 12/918,527, filed Aug. 23, 2010, Nakayama, et al.
U.S. Appl. No. 12/918,675, filed Aug. 23, 2010, Sato, et al.

* cited by examiner

*Primary Examiner* — Vu A Nguyen
(74) *Attorney, Agent, or Firm* — Oblon, Spivak, McClelland, Maier & Neustadt, L.L.P.

(57) ABSTRACT

Provided are 1) a polymer which is excellent in a reactivity to acid and a heat stability and which is less swollen in developing, 2) a compound shown below which is a raw material for the above polymer and 3) a photoresist composition which contains the above polymer and which is improved in LWR and excellent in a heat resistance.

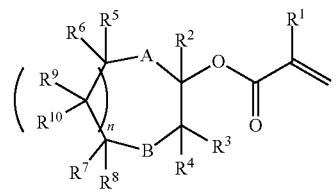

(wherein n represents an integer of 0 to 2; $R^1$ represents a hydrogen atom, methyl or the like; $R^2$ to $R^{10}$ each represent independently a hydrogen atom, a linear alkyl group, a branched alkyl group or the like; and A and B each represent independently an oxygen atom or a sulfur atom).

7 Claims, No Drawings

ACRYLATE ESTER DERIVATIVES AND POLYMER COMPOUNDS

TECHNICAL FIELD

The present invention relates to an acrylic ester derivative and raw materials for the same, a production process for them, a polymer obtained by polymerizing a raw material containing the acrylic ester derivative described above and a photoresist composition containing the above polymer.

The acrylic ester derivative of the present invention is useful as a raw material for a polymer obtained, for example, by polymerizing the above acrylic ester derivative as one of raw materials and a photoresist composition obtained by using the above acrylic ester derivative as a component. Further, alcohol obtained in the present invention is useful as a raw material for the above acrylic ester derivative.

BACKGROUND ART

In recent years, electronic devices are highly required to be increased in integration in the electronic device production field represented by integrated circuit device production, and this allows a photolithographic technique for forming fine patterns to be required. Accordingly, photoresist compositions corresponding to photolithography using as exposure light, radial rays having a wavelength of 200 nm or less such as an ArF excimer laser (wavelength: 193 nm), an $F_2$ excimer laser (wavelength: 157 nm) and the like are actively developed, and proposed are a large number of chemically amplified resist compositions comprising polymers having an acid-dissociable functional group and compounds (herein referred to as "a photoacid generator") which generate acid by irradiation (herein referred to as "exposure") of a radial ray. The above polymer having an acid-dissociable functional group comprises a basic structure in which a part of an alkali-readily soluble site of an alkali-soluble polymer is protected by a suitable acid-dissociable functional group, and selection of the above acid-dissociable functional group is very important in terms of controlling the performances of the photoresist composition.

Known as the existing acid-dissociable functional group are 1) groups having an adamantane structure (refer to a non-patent document 1 and a patent document 1) and 2) groups comprising a tetrahydropyranyl group (refer to a patent document 2). The acid-dissociable functional group is required to have both a high reactivity to acids and a stability in which it is not decomposed at a baking step, and is requested to have a heat stability of 130° C. or higher (refer to a non-patent document 3).

One of large problems of lithographic techniques in recent years includes line width variation of formed patterns which is called a line width roughness (herein referred to as "LWR"), and an allowable value thereof is required to be less than 8% of a line width (refer to a non-patent document 3). It is necessary for improving LWR to inhibit patterns from being deformed by swelling of a photoresist, that is, to allow a polymer which is a photoresist composition component to be less liable to be swollen.

Patent document 1: Japanese Patent Application Laid-Open No. 73173/1997
Patent document 2: Japanese Patent Application Laid-Open No. 88367/1993
Non-patent document 1: Journal of Photopolymer Science and Technology, Vol. 9, No. 3, p. 475 to 487 (1996)
Non-patent document 2: ITRS 2006, UP DATE version, part of lithography, p. 8
Non-patent document 3: ITRS 2006, UP DATE version, part of lithography, p. 7

DISCLOSURE OF THE INVENTION

Problems to be Solved by the Invention

The polymers described in the patent document 1 and the non-patent document 1 into which a group having an adamantane structure is introduced as an acid-dissociable functional group have a high reactivity to acids and a heat stability. However, the above polymers have a high hydrophobicity and are not satisfactory in an affinity with a developer to allow parts which are not dissolved in developing to remain in an exposed part, and it brings about swelling to result in causing a problem of increasing LWR. On the other hand, the polymer described in the patent document 2 into which a group having a tetrahydropyranyl group is introduced as an acid-dissociable functional group has the advantage that it has a high reactivity in terms of an acid dissociability, but it is lacking in a heat stability and is not satisfactory in a fundamental performance of a resist.

Accordingly, polymers for a photoresist composition which have a heat stability and are less liable to be swollen are still anxious to be developed, and the existing situation is that compounds having an acid-dissociable functional group for achieving the above matter are strongly anxious to be developed.

In order to solve the problems described above, the present invention has been made by paying attentions to an acid-dissociable functional group of a compound having an acid-dissociable functional group and intensely investigating it. The object of the present invention is to provide 1) a polymer which is excellent in a reactivity to acid and a heat stability and which is less swollen in developing, 2) a compound which is a raw material for the above polymer and 3) a photoresist composition which contains the above polymer and which is improved in LWR and excellent in a heat stability.

Means for Solving the Problems

Intense investigations carried out by the present inventors on relations of structures and physical properties of various polymers used for photoresist compositions with a swelling property in developing have resulted in finding that a polymer having a specific repetitive unit which has a high dissolution rate of an exposed part in a developer is effective for inhibiting a photoresist from being swollen, and thus they have completed the present invention.

That is, the present invention is achieved by providing:
1. an acrylic ester derivative (hereinafter referred to as an acrylic ester derivative (I)) represented by Formula (I) shown below:

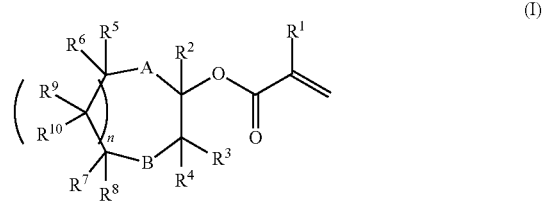

(wherein R¹ represents a hydrogen atom, methyl or trifluoromethyl;
combination of R², R³ and R⁴ is any of:
1) R², R³ and R⁴ each represent independently a hydrogen atom, a linear alkyl group having 1 to 6 carbon atoms, a branched alkyl group having 3 to 6 carbon atoms or a cyclic alkyl group having 3 to 6 carbon atoms;
2) R² and R³ are combined to represent an alkylene group having 3 to 6 carbon atoms, and R⁴ represents a hydrogen atom, a linear alkyl group having 1 to 6 carbon atoms, a branched alkyl group having 3 to 6 carbon atoms or a cyclic alkyl group having 3 to 6 carbon atoms; or
3) R² represents a hydrogen atom, a linear alkyl group having 1 to 6 carbon atoms, a branched alkyl group having 3 to 6 carbon atoms or a cyclic alkyl group having 3 to 6 carbon atoms, and R³ and R⁴ are combined to represent an alkylene group having 3 to 6 carbon atoms;
in n, R⁵, R⁶, R⁷, R⁸, R⁹ and R¹⁰,
1) when n is 0, R⁵ and R⁸ each represent independently a hydrogen atom, a linear alkyl group having 1 to 6 carbon atoms, a branched alkyl group having 3 to 6 carbon atoms or a cyclic alkyl group having 3 to 6 carbon atoms; R⁶ and R⁷ each represent independently a hydrogen atom, a linear alkyl group having 1 to 6 carbon atoms, a branched alkyl group having 3 to 6 carbon atoms or a cyclic alkyl group having 3 to 6 carbon atoms, or R⁶ and R⁷ are combined to represent an alkylene group having 3 to 6 carbon atoms; or
2) when n is 1 or 2, R⁵, R⁶, R⁷, R⁸, R⁹ and R¹⁰ each represent independently a hydrogen atom, a linear alkyl group having 1 to 6 carbon atoms, a branched alkyl group having 3 to 6 carbon atoms or a cyclic alkyl group having 3 to 6 carbon atoms; A and B each represent independently an oxygen atom or a sulfur atom, but A and B are not a sulfur atom at the same time),
2. a polymer (hereinafter referred to as a polymer (VIII)) obtained by polymerizing a raw material containing the acrylic ester derivative (I),
3. a photoresist composition containing the polymer according to the above item 2,
4. a production process for the acrylic ester derivative (I), comprising the step of:
reacting a cyclic alcohol (hereinafter referred to as cyclic alcohol (II)) represented by Formula (II) shown below:

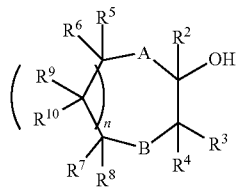

(II)

(wherein n, R², R³, R⁴, R⁵, R⁶, R⁷, R⁸, R⁹, R¹⁰, A and B are the same as defined above) with a polymerizable group-introducing agent represented by a formula CH₂=CR¹COX¹ (wherein R¹ is the same as defined above), a formula (CH₂=CR¹CO)₂O (wherein R¹ is the same as defined above), a formula CH₂=CR¹COOC(=O)R¹⁵ (wherein R¹ is the same as described above, and R¹⁵ represents t-butyl or 2,4,6-trichlorophenyl) or a formula CH₂=CR¹COOSO₂R¹⁶ (wherein R¹ is the same as described above, and R¹⁶ represents methyl or p-tolyl) in the presence of a basic substance,
5. a production process for an acrylic ester derivative (hereinafter referred to as an acrylic ester derivative (I-1)) represented by Formula (I-1) shown below:

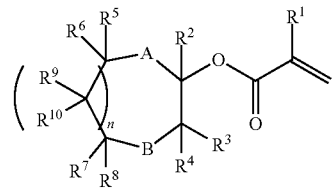

(I-1)

(wherein n, R¹, R², R³, R⁵, R⁶, R⁷, R⁸, R⁹ and R¹⁰ are the same as defined above; R⁴ represents a hydrogen atom; A represents an oxygen atom, and B represents an oxygen atom or a sulfur atom), comprising the step of:
reacting a cyclic olefin (hereinafter referred to as a cyclic olefin (III)) represented by Formula (III) shown below:

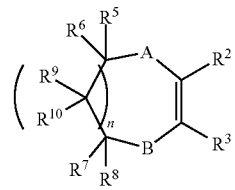

(III)

(wherein n, R², R³, R⁵, R⁶, R⁷, R⁸, R⁹ and R¹⁰ are the same as defined above; A represents an oxygen atom, and B represents an oxygen atom or a sulfur atom) with acrylic acid, methacrylic acid or 2-trifluoromethylacrylic acid,
6. an alcohol (hereinafter referred to as a cyclic alcohol (II-1)) represented by Formula (II-1) shown below:

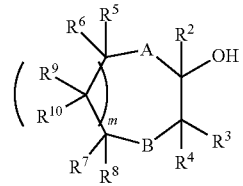

(II-1)

(wherein R², R³, R⁴, R⁵, R⁶, R⁷, R⁸, R⁹ and R¹⁰ are the same as defined above; m represents 1 or 2; A represents an oxygen atom, and B represents an oxygen atom or a sulfur atom),
7. a production process for the cyclic alcohol (II-1), comprising the steps of:
reacting an acetal compound (hereinafter referred to as an acetal compound (VI)) represented by Formula (IV) shown below:

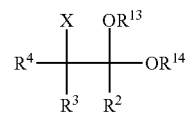

(IV)

(wherein R², R³ and R⁴ are the same as defined above; R¹³ and R¹⁴ each represent independently a linear alkyl group having 1 to 3 carbon atoms or a branched alkyl group having 3 to 6 carbon atoms; and X represents a chlorine atom, a bromine atom or an iodine atom) with a heteroalcohol (hereinafter referred to as a heteroalcohol (V-1)) represented by Formula (V-1) shown below:

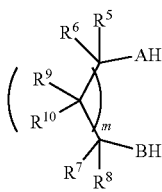

(V-1)

(wherein $R^5$, $R^6$, $R^7$, $R^8$, $R^9$ and $R^{10}$ are the same as defined above; m represents 1 or 2; A represents an oxygen atom, and B represents an oxygen atom or a sulfur atom) in the presence of a base and subjecting a resulting hydroxyacetal (hereinafter referred to as a hydroxyacetal (VI)) represented by Formula (VI) shown below:

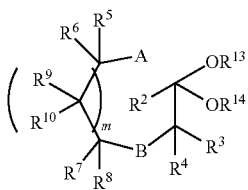

(VI)

(wherein $R^2$, $R^3$, $R^4$, $R^5$, $R^6$, $R^7$, $R^8$, $R^9$, $R^{10}$, $R^{13}$ and $R^{14}$ are the same as defined above; m represents 1 or 2; A represents an oxygen atom, and B represents an oxygen atom or a sulfur atom) to hydrolysis and cyclization reaction in the presence of an acid catalyst, 8. the acrylic ester derivative (the acrylic ester derivative (I-1)) according to the above item 1, wherein A is an oxygen atom, and $R^4$ is a hydrogen atom,
9. the acrylic ester derivative according to the above item 1, wherein n is 0 or 1; A is an oxygen atom; and $R^2$, $R^3$, $R^4$, $R^5$, $R^6$, $R^7$, $R^8$, $R^9$ and $R^{10}$ are a hydrogen atom or methyl,
10. the alcohol according to the above item 6, wherein m is 1 and
11. the alcohol according to the above item 6, wherein m is 1, and $R^2$, $R^3$, $R^4$, $R^5$, $R^6$, $R^7$, $R^8$, $R^9$ and $R^{10}$ are a hydrogen atom or methyl.

Effect of the Invention

According to the present invention, capable of being provided are 1) a polymer capable of providing a photoresist composition which is excellent in a reactivity to acid and a heat stability and which is less swollen in developing, 2) a compound which is a raw material for the above polymer and 3) a photoresist composition which contains the above polymer and which is improved in LWR and excellent in a heat stability.

BEST MODE FOR CARRYING OUT THE INVENTION

Acrylic Ester Derivative (I):

$R^1$ in the acrylic ester derivative (I) represents a hydrogen atom, methyl or trifluoromethyl. $R^1$ is preferably a hydrogen atom or methyl, more preferably methyl.

A and B in the acrylic ester derivative (I) each represent independently an oxygen atom or a sulfur atom, but A and B are not a sulfur atom at the same time.

Combination of $R^2$, $R^3$ and $R^4$ in the acrylic ester derivative (I) is any of 1), 2) and 3) shown below:
1) $R^2$, $R^3$ and $R^4$ each represent independently a hydrogen atom, a linear alkyl group having 1 to 6 carbon atoms, a branched alkyl group having 3 to 6 carbon atoms or a cyclic alkyl group having 3 to 6 carbon atoms;
2) $R^2$ and $R^3$ are combined to represent an alkylene group having 3 to 6 carbon atoms, and $R^4$ represents a hydrogen atom, a linear alkyl group having 1 to 6 carbon atoms, a branched alkyl group having 3 to 6 carbon atoms or a cyclic alkyl group having 3 to 6 carbon atoms; and
3) $R^2$ represents a hydrogen atom, a linear alkyl group having 1 to 6 carbon atoms, a branched alkyl group having 3 to 6 carbon atoms or a cyclic alkyl group having 3 to 6 carbon atoms, and $R^3$ and $R^4$ are combined to represent an alkylene group having 3 to 6 carbon atoms.

The above linear alkyl groups having 1 to 6 carbon atoms include, for example, methyl, ethyl, n-propyl, n-butyl, n-pentyl, n-hexyl and the like in all cases. The above branched alkyl groups having 3 to 6 carbon atoms include, for example, isopropyl, isobutyl, sec-butyl and the like in all cases. The above cyclic alkyl groups having 3 to 6 carbon atoms include, for example, cyclopropyl, cyclobutyl, cyclopentyl, cyclohexyl and the like in all cases.

The alkylene group having 3 to 6 carbon atoms in a case where $R^2$ and $R^3$ are combined includes, for example, propane-1,3-diyl, butane-1,4-diyl, pentane-1,5-diyl, hexane-1,6-diyl and the like. Among them, butane-1,4-diyl is preferred.

The alkylene group having 3 to 6 carbon atoms in a case where $R^3$ and $R^4$ are combined includes, for example, propane-1,3-diyl, butane-1,4-diyl, pentane-1,5-diyl, hexane-1,6-diyl and the like.

The combination of $R^2$, $R^3$ and $R^4$ is preferably 1) described above, and $R^2$, $R^3$ and $R^4$ each are more preferably a hydrogen atom or methyl, and $R^3$ is particularly preferably a hydrogen atom. All of them are further preferably a hydrogen atom.

In the acrylic ester derivative (I), n, $R^5$, $R^6$, $R^7$, $R^8$, $R^9$ and $R^{10}$ are any of 1) and 2) shown below.
1) When n is 0, $R^5$ and $R^8$ each represent independently a hydrogen atom, a linear alkyl group having 1 to 6 carbon atoms, a branched alkyl group having 3 to 6 carbon atoms or a cyclic alkyl group having 3 to 6 carbon atoms; $R^6$ and $R^7$ each represent independently a hydrogen atom, a linear alkyl group having 1 to 6 carbon atoms, a branched alkyl group having 3 to 6 carbon atoms or a cyclic alkyl group having 3 to 6 carbon atoms or $R^6$ and $R^7$ are combined to represent an alkylene group having 3 to 6 carbon atoms.
2) When n is 1 or 2, $R^5$, $R^6$, $R^7$, $R^8$, $R^9$ and $R^{10}$ each represent independently a hydrogen atom, a linear alkyl group having 1 to 6 carbon atoms, a branched alkyl group having 3 to 6 carbon atoms or a cyclic alkyl group having 3 to 6 carbon atoms.

The above linear alkyl groups having 1 to 6 carbon atoms include, for example, methyl, ethyl, n-propyl, n-butyl, n-pentyl, n-hexyl and the like in all cases. The above branched alkyl groups having 3 to 6 carbon atoms include, for example, isopropyl, isobutyl, sec-butyl and the like in all cases. The above cyclic alkyl groups having 3 to 6 carbon atoms include, for example, cyclopropyl, cyclobutyl, cyclopentyl, cyclohexyl and the like in all cases.

The alkylene group having 3 to 6 carbon atoms in a case where $R^6$ and $R^7$ are combined includes, for example, propane-1,3-diyl, butane-1,4-diyl, pentane-1,5-diyl, hexane-1,6-diyl and the like. Among them, butane-1,4-diyl is preferred.

The term n is preferably 0 or 1, more preferably 0.

When n is 0, $R^5$, $R^6$, $R^7$ and $R^8$ each are preferably a hydrogen atom or methyl.

When n is 1, $R^5$, $R^6$, $R^7$, $R^8$, $R^9$ and $R^{10}$ each are preferably a hydrogen atom or methyl, and all of $R^5$, $R^6$, $R^7$, $R^8$, $R^9$ and $R^{10}$ are more preferably a hydrogen atom.

The acrylic ester derivative (I) includes, for example, compounds represented by Formulas (1-1) to (1-20) shown below, but it shall not specifically be restricted to them.

(1-1)
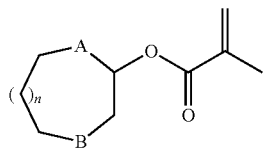

(1-2)
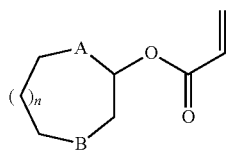

(1-3)
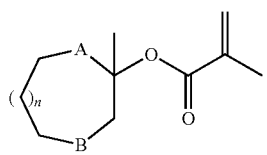

(1-4)
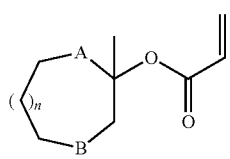

(1-5)
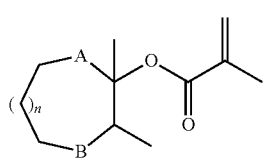

(1-6)
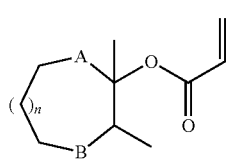

(1-7)
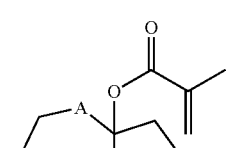

(1-8)
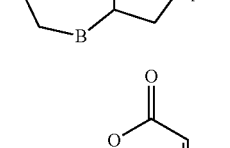

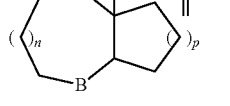

(1-9)
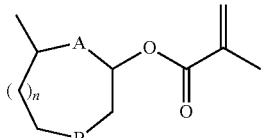

(1-10)
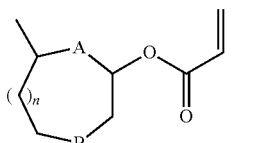

(1-11)
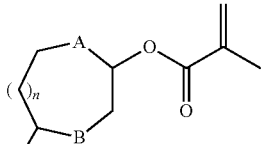

(1-12)
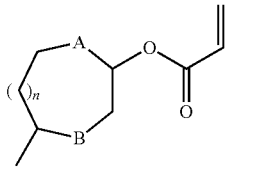

(1-13)
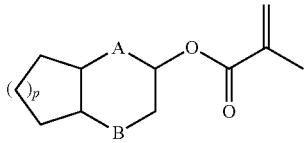

(1-14)
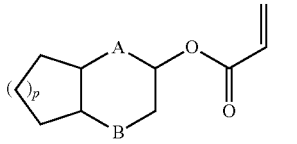

(1-15)
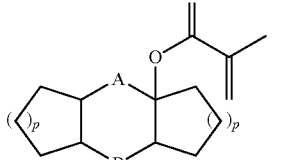

(1-16)
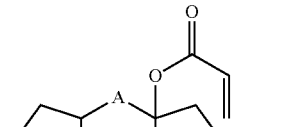

(1-17)

-continued
(1-18)
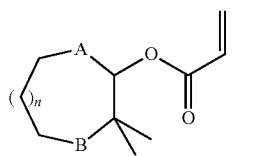
(1-19)
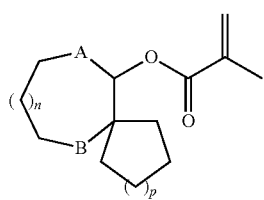
(1-20)
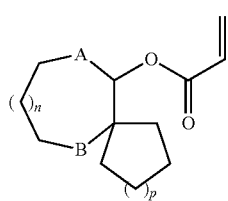
In the formulas described above, A, B and n are the same as defined above, and p represents 1 or 2.
The specific examples of the compounds represented by Formulas (1-1) to (1-20) include compounds represented by Formulas (2-1) to (2-114) shown below, but they shall not specifically be restricted to the above compounds:
(2-1)
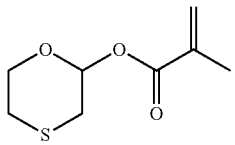
(2-2)
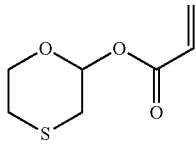
(2-3)
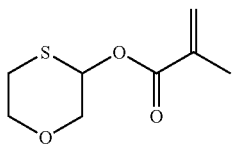
(2-4)
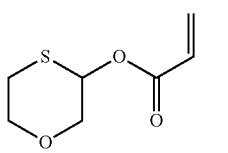
(2-5)
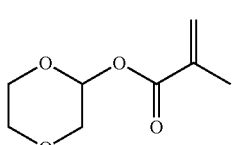
(2-6)
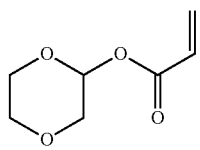
(2-7)
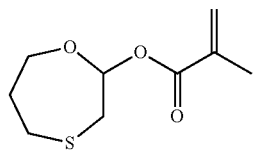
(2-8)
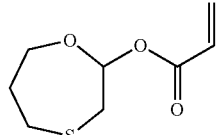
(2-9)
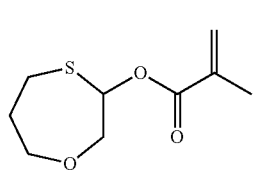
(2-10)
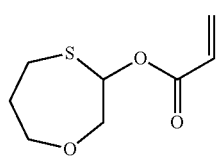
(2-11)
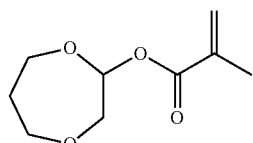
(2-12)
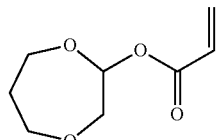
(2-13)
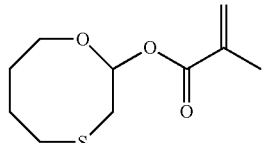
(2-14)
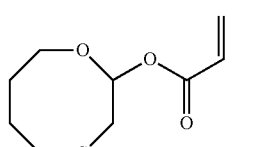
(2-15)
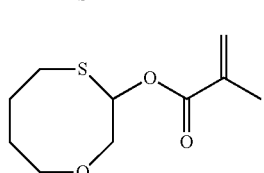

(2-16) 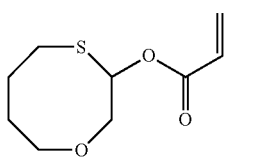
(2-17) 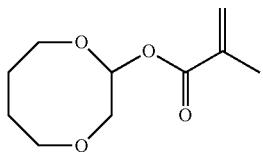
(2-18) 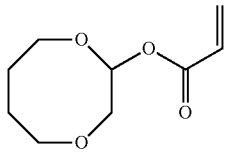
(2-19) 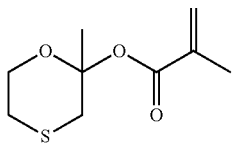
(2-20) 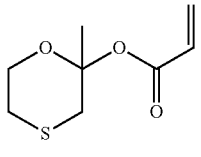
(2-21) 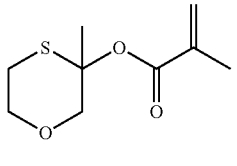
(2-22) 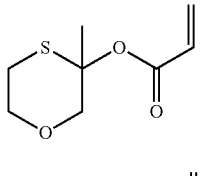
(2-23) 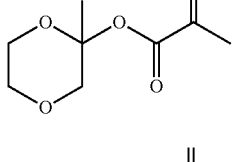
(2-24) 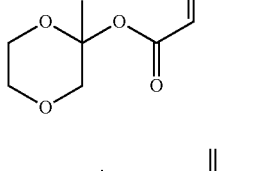
(2-25) 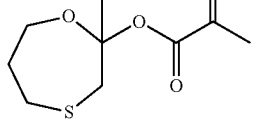
(2-26) 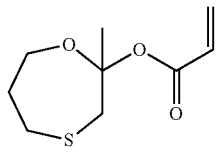
(2-27) 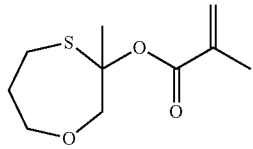
(2-28) 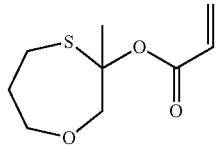
(2-29) 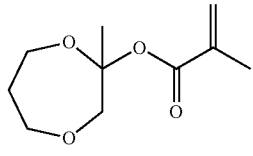
(2-30) 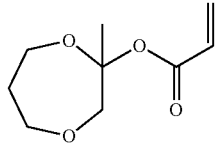
(2-31) 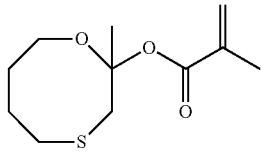
(2-32) 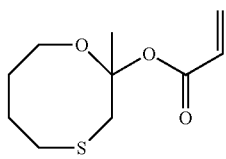
(2-33) 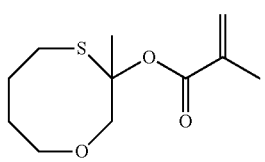
(2-34) 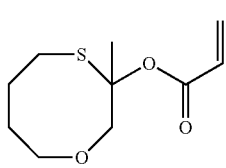
(2-35) 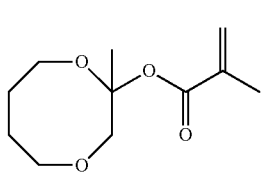

(2-36)
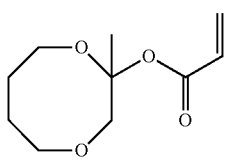
(2-37)
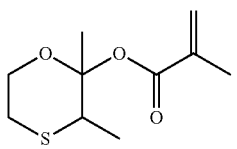
(2-38)
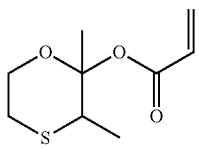
(2-39)
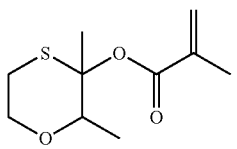
(2-40)
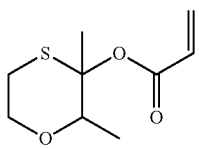
(2-41)
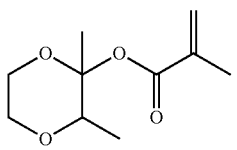
(2-42)
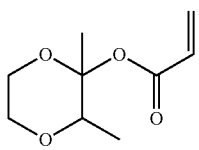
(2-43)
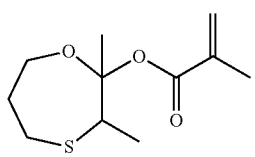
(2-44)
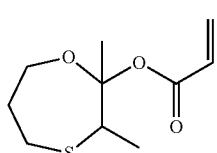
(2-45)
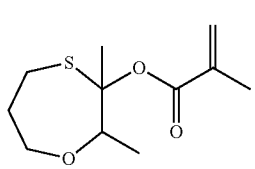
(2-46)
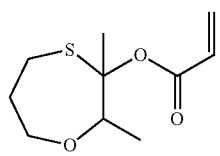
(2-47)
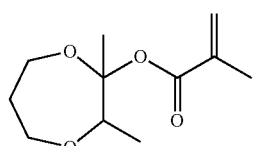
(2-48)
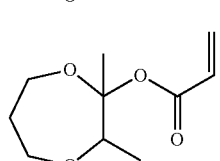
(2-49)
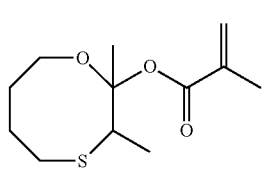
(2-50)
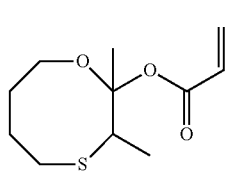
(2-51)
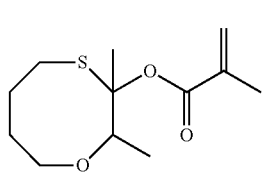
(2-52)
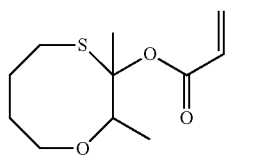
(2-53)
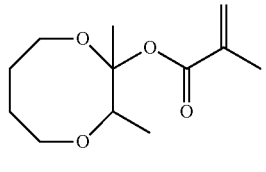
(2-54)
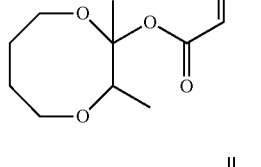
(2-55)
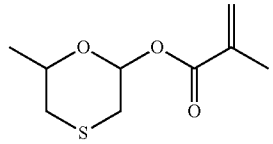

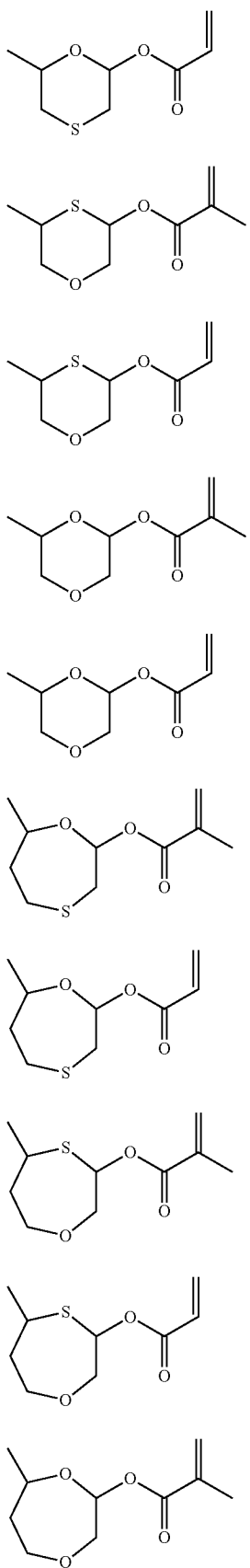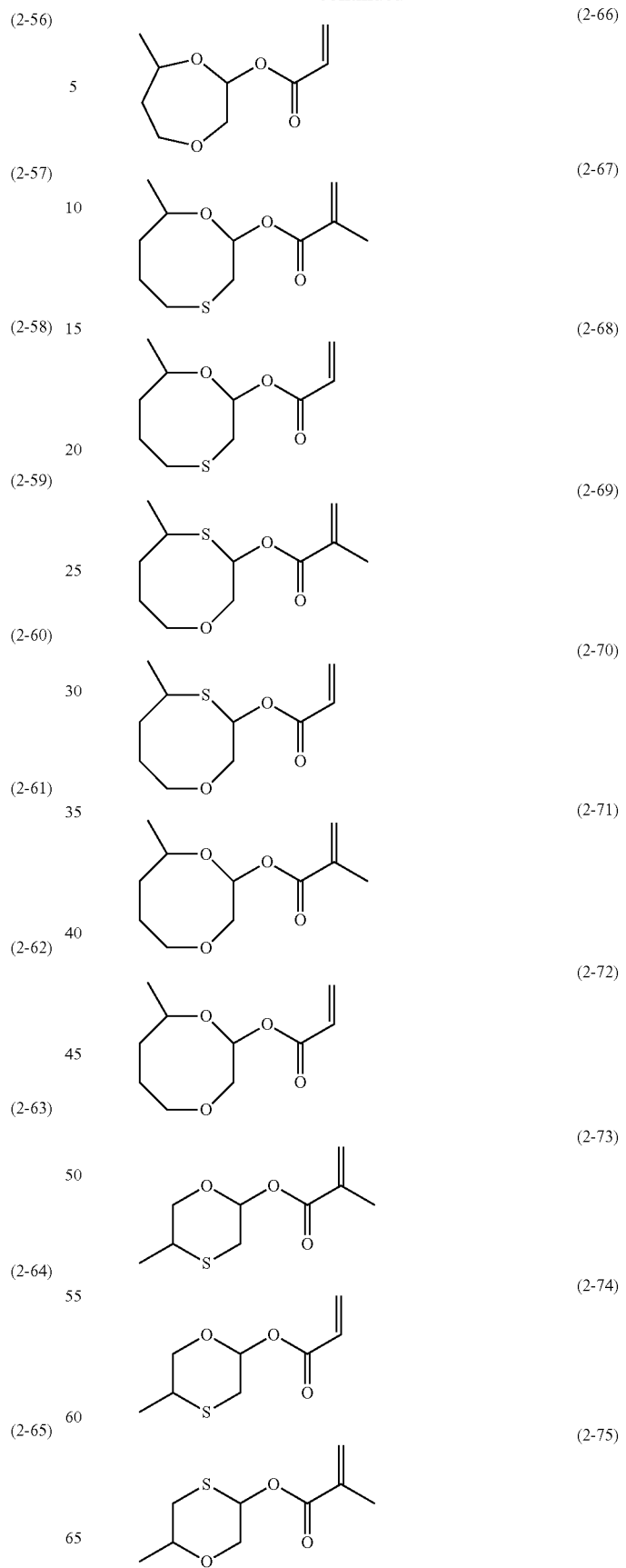

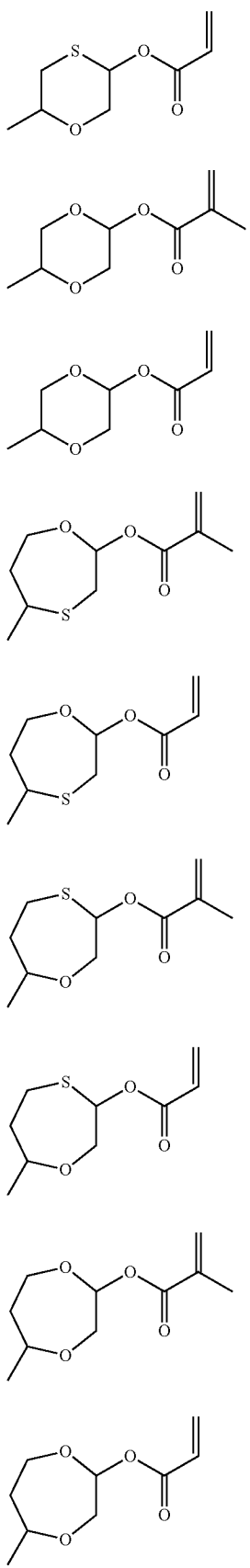
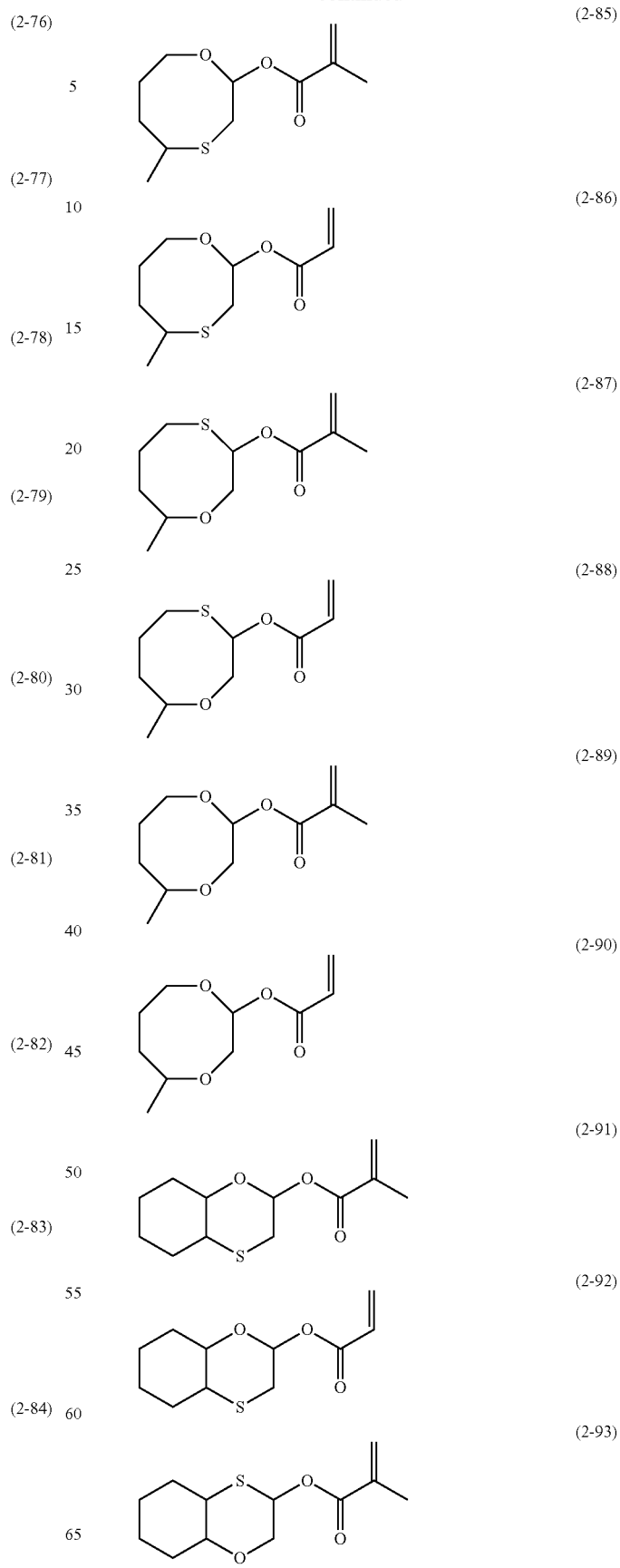

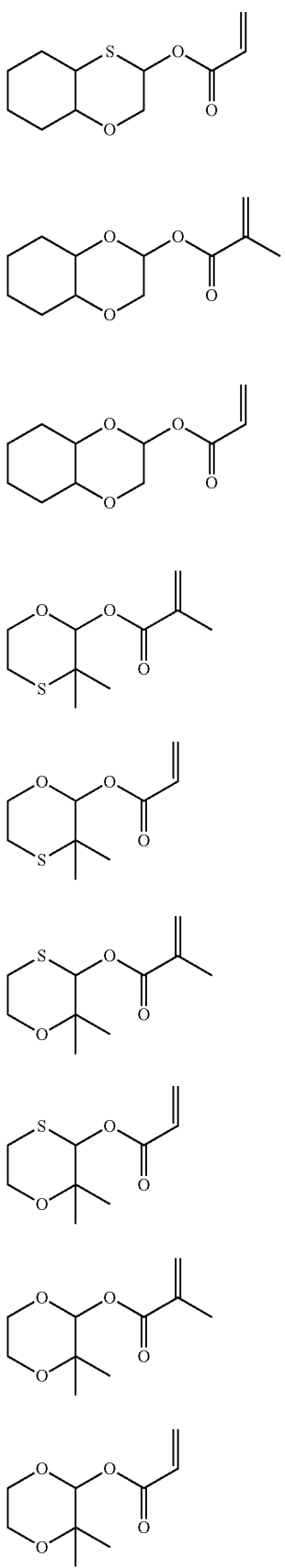
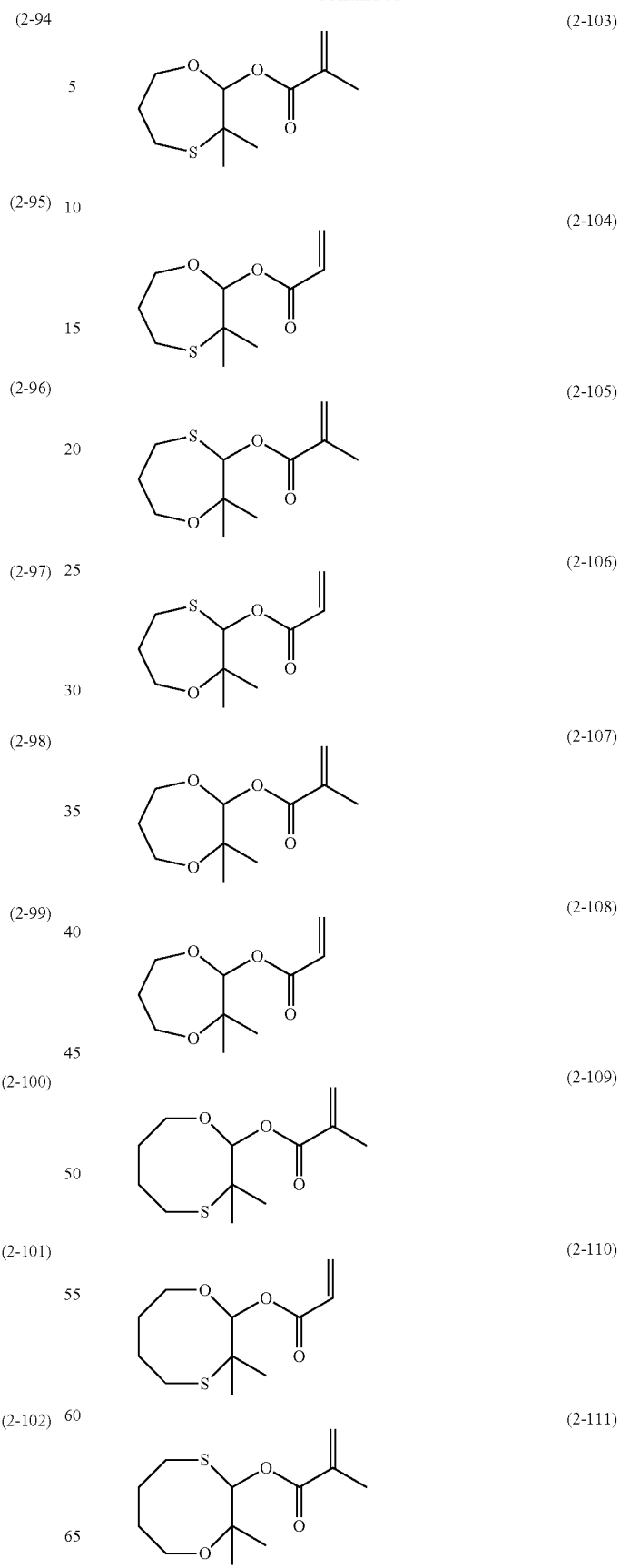

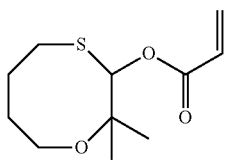
(2-112)

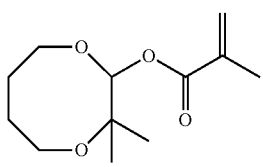
(2-113)

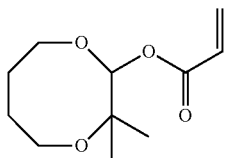
(2-114)

Production Process for Acrylic Ester Derivative (I):

The acrylic ester derivative (I) can be produced, for example, by processes A and B shown by the following schemes. In the process A, the acrylic ester derivative (I) can be produced. Further, in the process B, the acrylic ester derivative (I-1) can be produced.

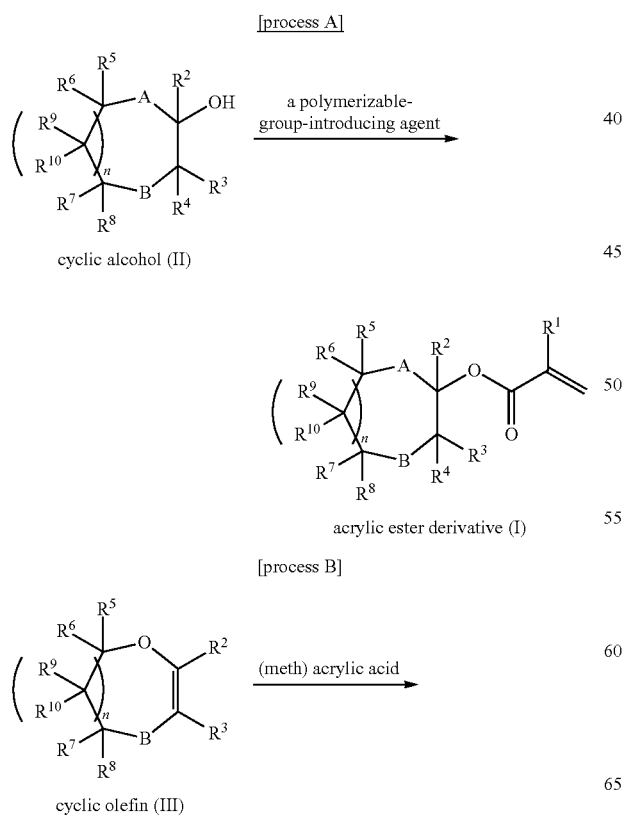

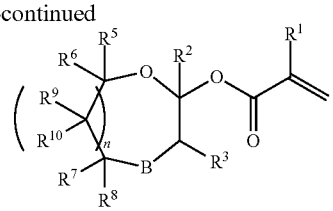
acrylic ester derivative (I-1)

In the schemes shown above, n, $R^1$, $R^2$, $R^3$, $R^4$, $R^5$, $R^6$, $R^7$, $R^8$, $R^9$, $R^{10}$, A and B are the same as defined above.

The process A and the process B in the schemes shown above shall be explained in order.

Process A:

Among the cyclic alcohols (II) used in the process A, the cyclic alcohols (II-1) in which n is 1 or 2 and in which A is an oxygen atom are novel compounds. A production method for the above cyclic alcohols (II) shall be explained later.

The cyclic alcohols (II) other than the cyclic alcohols (II-1) are industrially available or can be produced by a process in which ester compounds produced by a method described in Gazzeta Chimica Italiana, 127 (1), p. 11 to 17 (1997) and a method described in Journal of Medicinal Chemistry, Vol. 25, No. 5, p. 522 to 526 (1982) are subjected to hydrolysis reaction.

The cyclic alcohol (II) includes, for example, compounds represented by Formulas (3-1) to (3-100) shown below, but it shall not specifically be restricted to them:

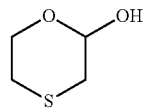
(3-1)

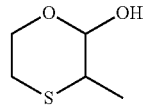
(3-2)

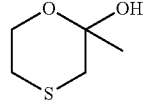
(3-3)

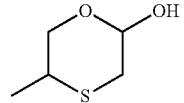
(3-4)

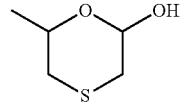
(3-5)

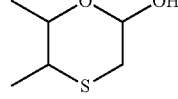
(3-6)

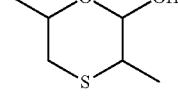
(3-7)

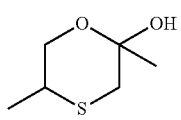 (3-8)
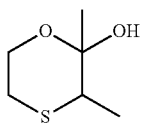 (3-9)
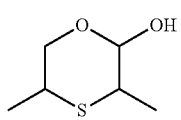 (3-10)
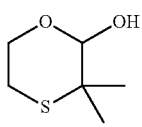 (3-11)
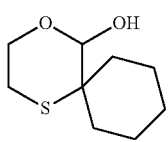 (3-12)
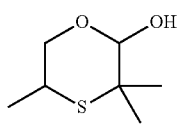 (3-13)
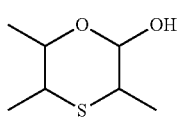 (3-14)
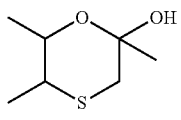 (3-15)
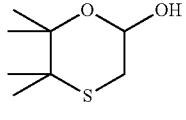 (3-16)
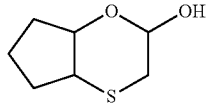 (3-17)
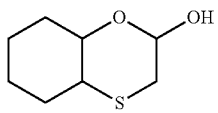 (3-18)
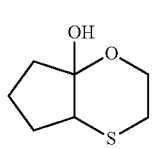 (3-19)
(3-20)
(3-21)
(3-22)
(3-23)
(3-24)
(3-25)
(3-26)
(3-27)
(3-28)
(3-29)
(3-30)
(3-31)

(3-32) 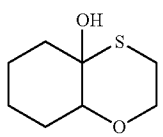
(3-33) 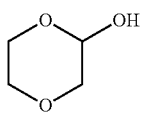
(3-34) 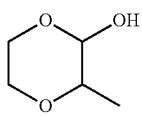
(3-35) 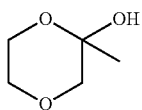
(3-36) 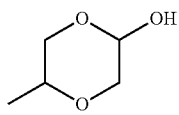
(3-37) 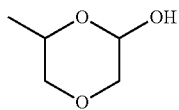
(3-38) 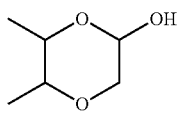
(3-39) 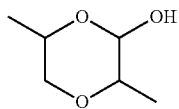
(3-40) 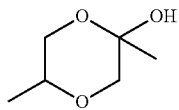
(3-41) 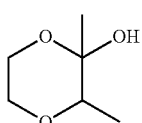
(3-42) 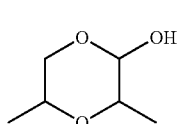
(3-43) 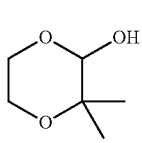
(3-44) 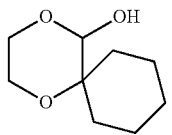
(3-45) 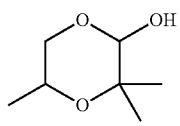
(3-46) 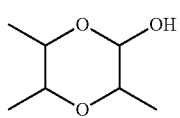
(3-47) 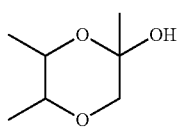
(3-48) 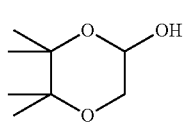
(3-49) 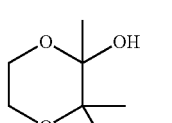
(3-50) 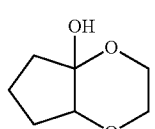
(3-51) 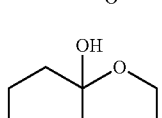
(3-52) 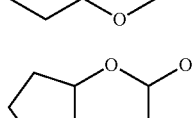
(3-53) 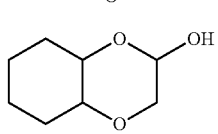
(3-54) 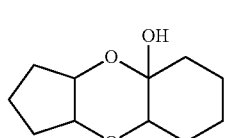
(3-55) 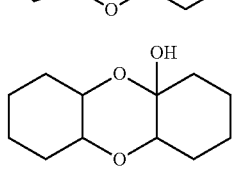

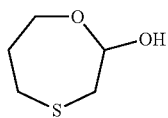 (3-56)
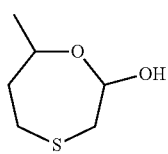 (3-57)
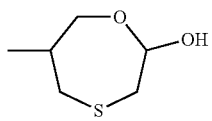 (3-58)
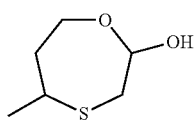 (3-59)
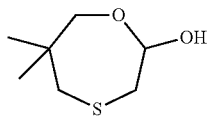 (3-60)
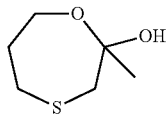 (3-61)
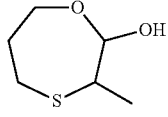 (3-62)
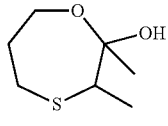 (3-63)
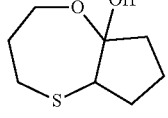 (3-64)
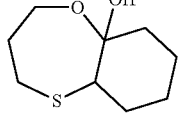 (3-65)
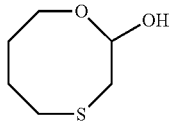 (3-66)
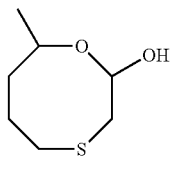 (3-67)
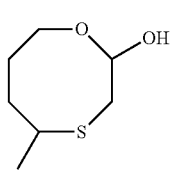 (3-68)
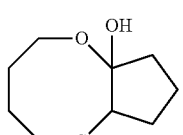 (3-69)
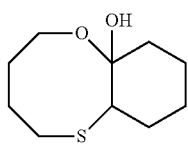 (3-70)
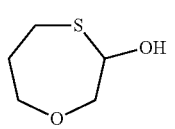 (3-71)
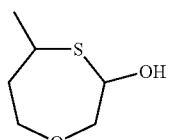 (3-72)
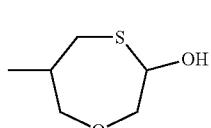 (3-73)
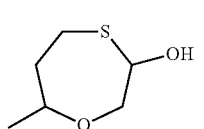 (3-74)
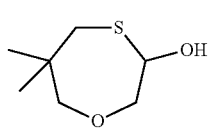 (3-75)
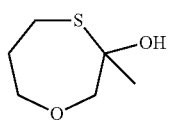 (3-76)
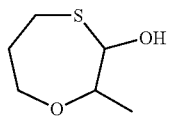 (3-77)

(3-78) 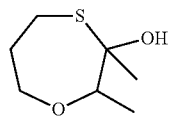
(3-79) 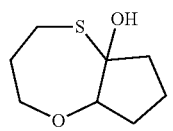
(3-80) 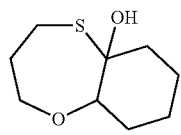
(3-81) 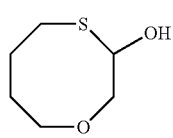
(3-82) 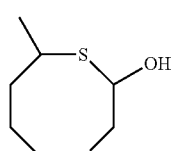
(3-83) 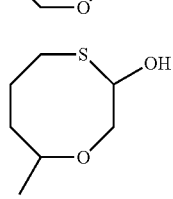
(3-84) 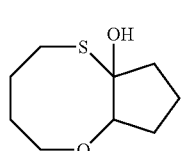
(3-85) 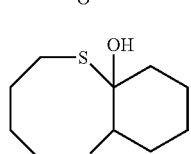
(3-86) 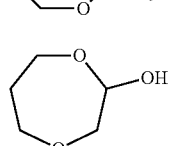
(3-87) 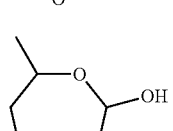
(3-88) 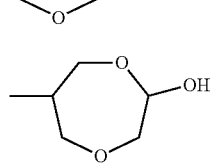
(3-89) 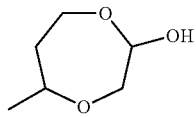
(3-90) 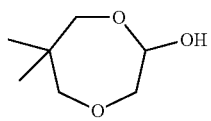
(3-91) 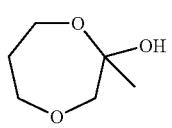
(3-92) 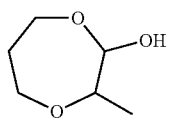
(3-93) 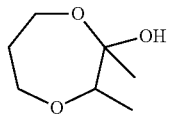
(3-94) 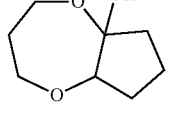
(3-95) 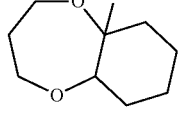
(3-96) 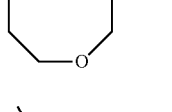
(3-97) 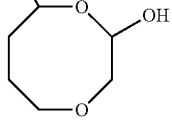
(3-98) 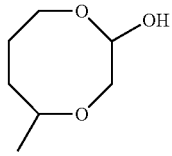
(3-99) 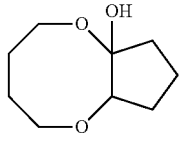

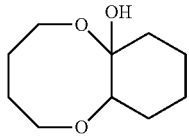

(3-100)

The production process for the acrylic ester derivative (I) by the process A can be carried out by reacting the cyclic alcohol (II) with a compound (hereinafter referred to as a polymerizable group-introducing agent) represented by a formula $CH_2=CR^1COX^1$, a formula $(CH_2=CR^1CO)_2O$, a formula $CH_2=CR^1COOC(=O)R^{15}$ or a formula $CH_2=CR^1COOSO_2R^{16}$ in the presence of a basic substance.

In the polymerizable group-introducing agent described above, all of $R^1$ are the same as $R^1$ in the acrylic ester derivative (I) described above, and the preferred groups are the same as well. $X^1$ represents a chlorine atom, a bromine atom or an iodine atom, and it is preferably a chlorine atom or a bromine atom. $R^{15}$ represents t-butyl or 2,4,6-trichlorophenyl. $R^{16}$ represents methyl or p-tolyl.

The specific examples of the polymerizable group-introducing agent represented by the formula $CH_2=CR^1COX^1$ which is used in the process A include, for example, acrylic chloride, methacrylic chloride, 2-trifluoromethylacrylic chloride and the like.

The specific examples of the polymerizable group-introducing agent represented by the formula $(CH_2=CR^2CO)_2O$ include acrylic anhydride, methacrylic anhydride, 2-trifluoromethylacrylic anhydride and the like.

The specific examples of the polymerizable group-introducing agent represented by the formula $CH_2=CR^2COOC(=O)R^{15}$ include acrylic pivalic anhydride, acrylic 2,4,6-trichlorobenzoic anhydride, methacrylic pivalic anhydride, methacrylic 2,4,6-trichlorobenzoic anhydride, 2-trifluoromethylacrylic pivalic anhydride, 2-trifluoromethylacrylic 2,4,6-trichlorobenzoic anhydride and the like.

The specific examples of the polymerizable group-introducing agent represented by the formula $CH_2=CR^2COOSO_2R^{16}$ include acrylic methanesulfonic anhydride, acrylic p-toluenesulfonic anhydride, methacrylic methanesulfonic anhydride, methacrylic p-toluenesulfonic anhydride, 2-trifluoromethylacrylic methanesulfonic anhydride, 2-trifluoromethylacrylic p-toluenesulfonic anhydride and the like.

Among them, the polymerizable group-introducing agents represented by the formula $CH_2=CR^1COX^1$ are preferred, and acrylic chloride and methacrylic chloride are more preferred.

A use amount of the polymerizable group-introducing agent falls in a range of preferably 0.8 to 5 moles, more preferably 0.8 to 3 moles based on 1 mole of the cyclic alcohol (II) from the viewpoints of an economical efficiency and easiness in after-treatment.

Any of an inorganic base and an organic base can be used for the basic substance used in the process A. The inorganic base includes, for example, alkali metal hydrides such as sodium hydride, potassium hydride and the like; alkali metal hydroxides such as sodium hydroxide, potassium hydroxide and the like; and alkali metal carbonates such as sodium carbonate, potassium carbonate and the like. The organic base includes, for example, tertiary amines such as triethylamine, tributylamine, N,N-dimethylaniline, diazabicyclo[2.2.2]octane and the like; and nitrogen-containing heterocyclic aromatic compounds such as pyridine, 4-(N,N-dimethylamino) pyridine and the like. They may be used alone or in a mixture of two or more kinds thereof. Among them, the tertiary amines are preferred.

A use amount of the basic substance falls in a range of preferably 0.8 to 5 moles, more preferably 0.8 to 3 moles based on 1 mole of the cyclic alcohol (II) from the viewpoints of an economical efficiency and easiness in after-treatment.

The process A can be carried out in the presence or the absence of a solvent. The solvent shall not specifically be restricted as long as the reaction is not inhibited, and it includes, for example, ethers such as diethyl ether, diisopropyl ether, tetrahydrofuran and the like; aliphatic hydrocarbons such as hexane, heptane, octane and the like; halogenated hydrocarbons such as methylene chloride, 1,2-dichloroethane and the like; aromatic hydrocarbons such as toluene, xylene, cymene and the like; N,N-dimethylformamide; dimethylsulfoxide and the like. They may be used alone or in a mixture of two or more kinds thereof.

When the solvent is used, a use amount thereof shall not specifically be restricted and falls usually in a range of preferably 0.1 to 20 parts by mass, more preferably 0.1 to 10 parts by mass based on 1 part by mass of the cyclic alcohol (II).

The process A is carried out in a range of preferably −80 to 100° C., more preferably −50 to 80° C. and further preferably −20 to 40° C. The reaction time is varied depending on the kinds and the use amounts of the cyclic alcohol (II) and the polymerizable group-introducing agent, the kind and the use amount of the basic substance, the kind and the use amount of the solvent and the reaction temperature, and it falls usually in a range of 10 minutes to 10 hours.

In the process A, the reaction can be terminated by adding water and/or alcohol. Such alcohol includes, for example, methanol, ethanol, n-propanol, i-propanol and the like.

A use amount of water and/or alcohol is preferably 1 mole or more based on excess 1 mole of the polymerizable group-introducing agent to the cyclic alcohol (II) from the viewpoints of completely decomposing the unreacted polymerizable group-introducing agent and inhibiting by-products.

The acrylic ester derivative (I) obtained via the above process A is preferably separated and refined, if necessary, by a conventional method. For example, the reaction mixture is washed with water and then concentrated, and a purity thereof can be elevated by a conventional method used for separating and refining organic compounds, such as distillation, column chromatography or recrystallization.

Further, the acrylic ester derivative (I) obtained can be decreased, if necessary, in a metal content by chelate agent treatment with nitrilotriacetic acid, ethylenediaminetetraacetic acid and the like or metal-removing filter treatment by Zeta Plus (trade name, manufactured by Cuno K.K.) and Protego (trade name, manufactured by Nihon Microlis K.K.).

Process B:

The process B is a process in which acrylic acid, methacrylic acid or 2-trifluoromethylacrylic acid (hereinafter referred generically to as (meth)acrylic acid) is added to the cyclic olefin (III).

The cyclic olefin (III) includes, for example, compounds represented by Formulas (4-1) to (4-51) shown below, but it shall not specifically be restricted to them:

(4-1)

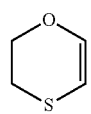

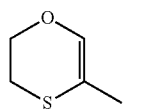 (4-2)
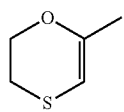 (4-3)
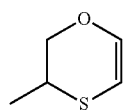 (4-4)
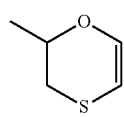 (4-5)
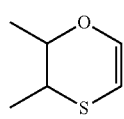 (4-6)
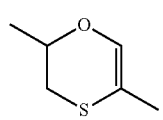 (4-7)
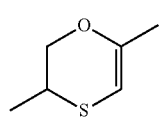 (4-8)
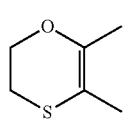 (4-9)
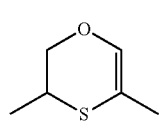 (4-10)
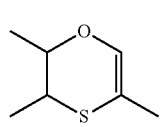 (4-11)
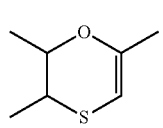 (4-12)
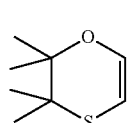 (4-13)
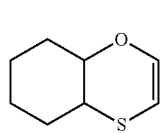 (4-14)
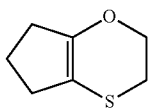 (4-15)
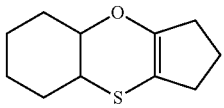 (4-16)
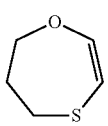 (4-17)
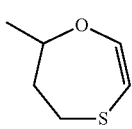 (4-18)
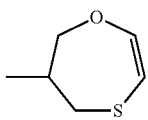 (4-19)
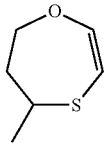 (4-20)
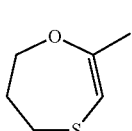 (4-21)
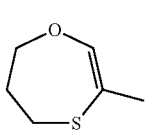 (4-22)
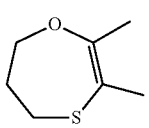 (4-23)
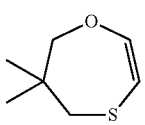 (4-24)
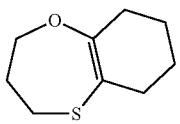 (4-25)
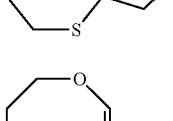
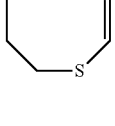 (4-26)

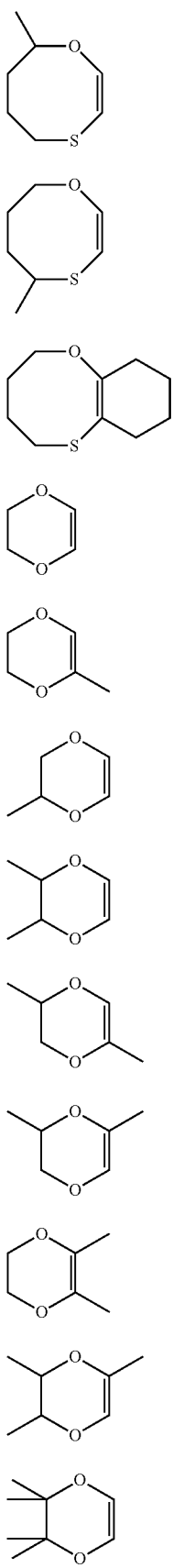
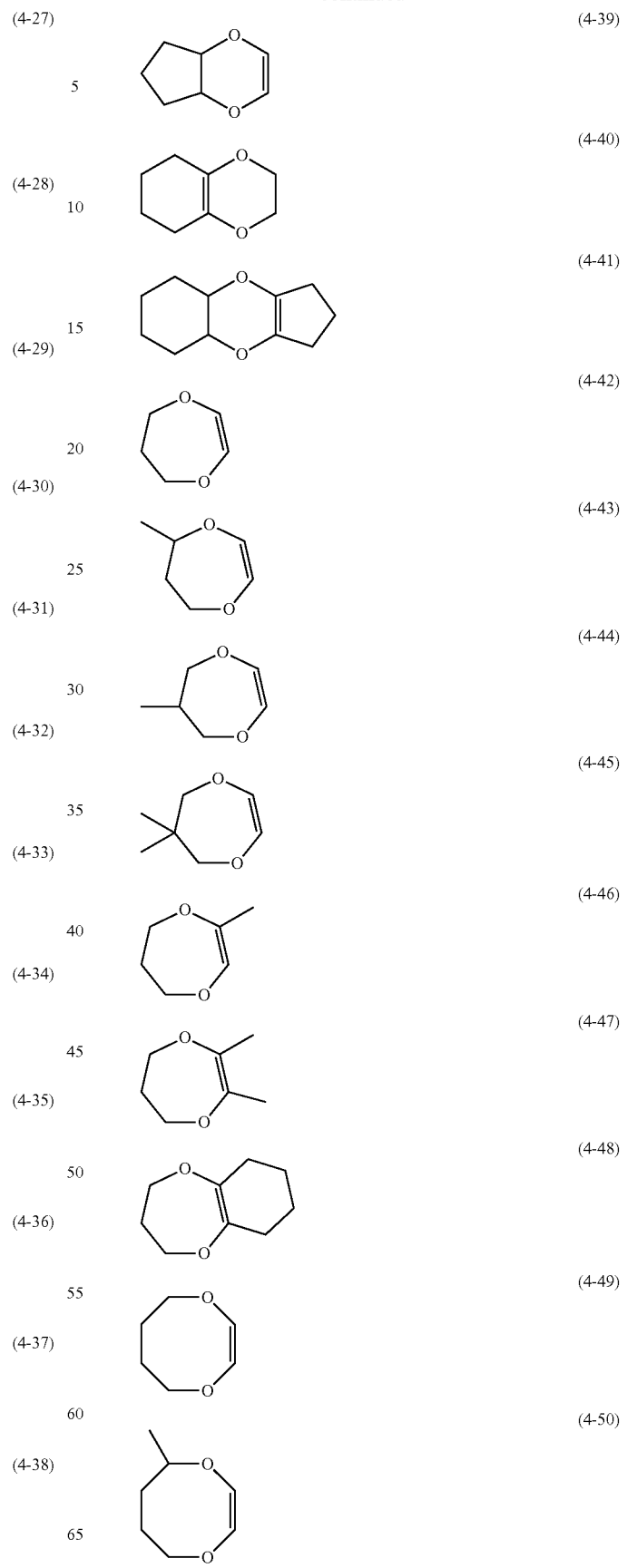

-continued (4-51)

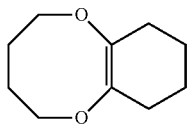

The cyclic olefin (III) used in the process B is industrially available or can be produced by a method described in Journal of the American Chemical Society, 77, p. 1169 to 1174 (1955).

The process B is carried out preferably in the presence of a polymerization inhibitor. The polymerization inhibitor used includes, for example, hydroquinone, p-methoxyphenol, phenothiazine, 4-methoxy-1-naphthol, methylhydroquinone, tert-butylhydroquinone and the like. They may be used alone or in a mixture of two or more kinds thereof.

When the polymerization inhibitor is used, a use amount thereof is preferably 1 to 10000 ppm, more preferably 10 to 5000 ppm based on (meth)acrylic acid from the viewpoints of an economical efficiency and easiness in after-treatment.

The process B can be carried out in the presence or the absence of a solvent. The solvent shall not specifically be restricted as long as the reaction is not inhibited, and it includes, for example, aliphatic hydrocarbons such as hexane, heptane, octane and the like; aromatic hydrocarbons such as toluene, xylene, cymene and the like; halogenated hydrocarbons such as methylene chloride, dichloroethane and the like; ethers such as tetrahydrofuran (THF), diisopropyl ether and the like. They may be used alone or in a mixture of two or more kinds thereof. Further, (meth)acrylic acid or the cyclic olefin (III) can be used as a solvent-cum-reactant.

When (meth)acrylic acid is used as a solvent-cum-reactant, a use amount thereof falls in a range of preferably 0.1 to 10 mass times, more preferably 0.1 to 5 mass times based on the cyclic olefin (III) from the viewpoints of an economical efficiency and easiness in after-treatment. Also, when the cyclic olefin (III) is used as a solvent-cum-reactant, a use amount thereof falls in a range of preferably 0.1 to 10 mass times, more preferably 0.1 to 5 mass times based on (meth)acrylic acid.

The process B is carried out preferably in the presence of an acid catalyst. (Meth)acrylic acid can also be functioned as an acid catalyst, but the following acids are preferably used.

The acid catalyst includes, for example, carboxylic acids such as trichloroacetic acid, trifluoroacetic acid and the like; sulfonic acids such as toluenesulfonic acid, p-toluenesulfonic acid, methanesulfonic acid, ethanesulfonic acid, 10-camphorsulfonic acid, trifluoromethanesulfonic acid and the like; and mineral acids such as sulfuric acid, hydrochloric acid, phosphoric acid and the like.

When the acid catalyst is used, a use amount thereof falls in a range of preferably 0.001 to 1 time mole, more preferably 0.01 to 0.5 time mole based on the cyclic olefin (III) from the viewpoints of an economical efficiency and easiness in after-treatment.

A reaction temperature in the process B is varied depending on the kinds of the cyclic olefin (III), (meth)acrylic acid and the acid catalyst suitably used, and it falls in a range of preferably 0 to 100° C.

A pressure in the process B is varied depending on the kinds of the cyclic olefin (III), (meth)acrylic acid and the solvent, and it is preferably atmospheric pressure from the viewpoint of easiness in operation.

In the process B, the reaction can be terminated by neutralizing the acid catalyst with a neutralizer or removing the acid catalyst from the reaction system.

The neutralizer includes, for example, alkali metal hydroxides such as sodium hydroxide, potassium hydroxide and the like; alkali metal carbonates such as sodium carbonate, potassium carbonate and the like; alkali metal hydrogencarbonates such as sodium hydrogencarbonate, potassium hydrogencarbonate and the like; tertiary amines such as triethylamine, tributylamine and the like; nitrogen-containing heterocyclic aromatic hydrocarbons such as pyridine and the like.

When the neutralizer is used to terminate the reaction, a use amount of the neutralizer falls in a range of preferably 1 to 3 equivalents based on the acid catalyst from the viewpoints of an economical efficiency and easiness in after-treatment.

A method for terminating the reaction by removing the acid catalyst from the reaction system includes, for example, a method in which a reaction solution under reaction is suitably diluted with a suited reaction solvent and in which it is then washed with water or an alkaline aqueous solution. The solvent shall not specifically be restricted as long as the reaction is not inhibited, and esters such as methyl acetate, ethyl acetate, butyl acetate and the like in addition to the solvents described above which can be used in the process B are suitably used. A use amount of the above solvent falls in a range of preferably 0.1 to 10 mass times, more preferably 0.1 to 5 mass times based on a whole mass of the reaction solution from the viewpoints of an economical efficiency and easiness in after-treatment.

Also, the basic substance in the alkaline aqueous solution includes, for example, inorganic bases such as sodium hydroxide, potassium hydroxide, sodium carbonate, sodium hydrogencarbonate, potassium carbonate, potassium hydrogencarbonate and the like. When the alkaline aqueous solution is used, a use amount of the basic substance falls in a range of preferably 0.1 to 3 equivalents based on the acid catalyst from the viewpoints of an economical efficiency and easiness in after-treatment.

The acrylic ester derivative (I-1) obtained via the above process B is preferably separated and refined, if necessary, by a conventional method. For example, the reaction mixture is washed with water and then concentrated, and a purity thereof can be elevated by a conventional method used for separating and refining organic compounds, such as distillation, column chromatography or recrystallization.

Further, the acrylic ester derivative (I-1) obtained can be decreased, if necessary, in a metal content by chelate agent treatment by nitrilotriacetic acid, ethylenediaminetetraacetic acid and the like or metal-removing filter treatment by Zeta Plus (trade name, manufactured by Cuno K.K.) and Protego (trade name, manufactured by Nihon Microlis K.K.).

The acrylic ester derivative (I-1) includes, for example, the compounds represented by Formulas (1-1) to (1-16) described above, and the specific examples thereof include the compounds represented by Formulas (2-1) to (2-96) described above, but it shall not specifically be restricted to them.

Production Process for Cyclic Alcohol (II-1):

Among the cyclic alcohols (II) used in the process A described above, the cyclic alcohols (II-1) in which n is 1 or 2 (in this case, n is represented by m) and in which A is an oxygen atom include, for example, compounds represented by Formulas (5-1) to (5-38) shown below, but they shall not specifically be restricted to them:

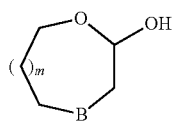 (5-1)
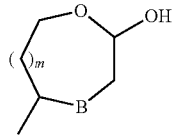 (5-2)
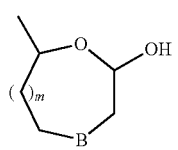 (5-3)
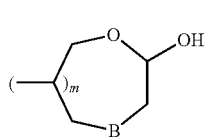 (5-4)
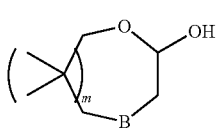 (5-5)
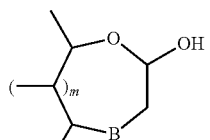 (5-6)
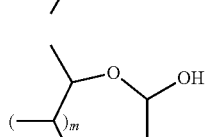 (5-7)
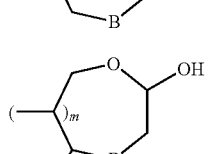 (5-8)
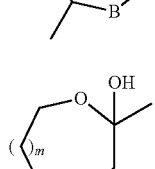 (5-9)
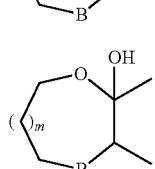 (5-10)
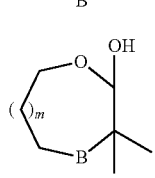 (5-11)
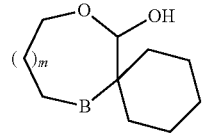 (5-12)
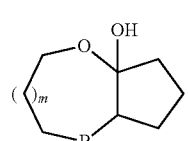 (5-13)
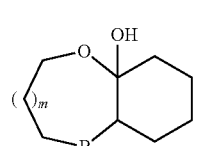 (5-14)
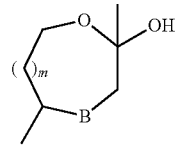 (5-15)
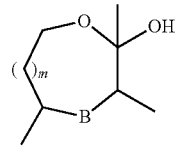 (5-16)
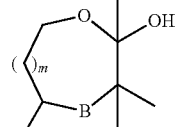 (5-17)
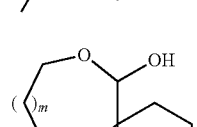 (5-18)
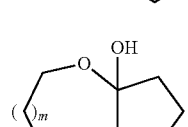 (5-19)
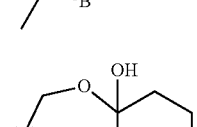 (5-20)
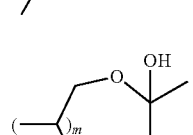 (5-21)

(5-22) 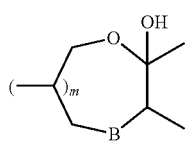
(5-23) 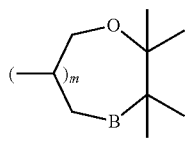
(5-24) 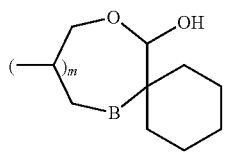
(5-25) 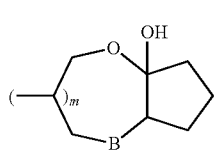
(5-26) 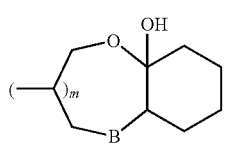
(5-27) 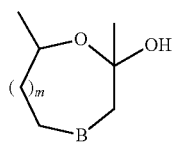
(5-28) 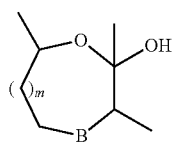
(5-29) 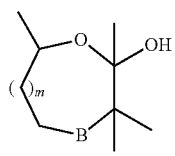
(5-30) 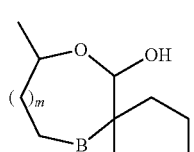
(5-31) 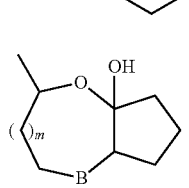
(5-32) 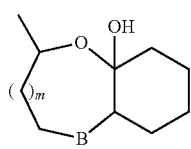
(5-33) 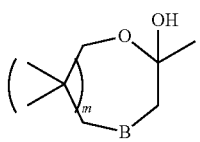
(5-34) 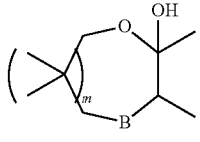
(5-35) 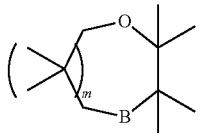
(5-36) 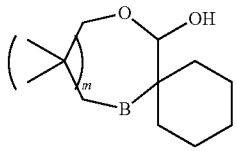
(5-37) 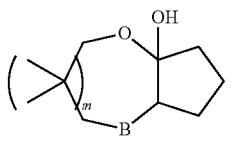
(5-38) 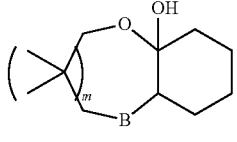
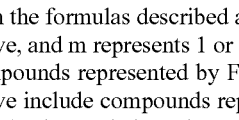
In the formulas described above, B is the same as defined above, and m represents 1 or 2. The specific examples of the compounds represented by Formulas (5-1) to (5-38) shown above include compounds represented by Formulas (6-1) to (6-30) shown below, but they shall not specifically be restricted to them:
(6-1) 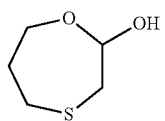
(6-2) 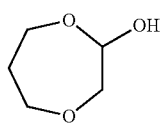

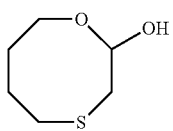 (6-3)
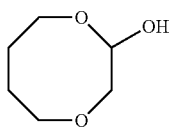 (6-4)
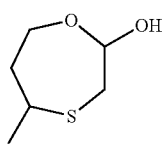 (6-5)
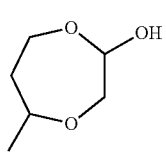 (6-6)
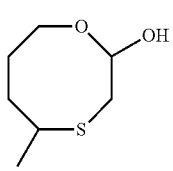 (6-7)
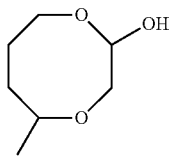 (6-8)
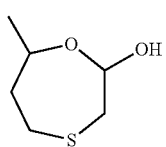 (6-9)
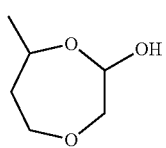 (6-10)
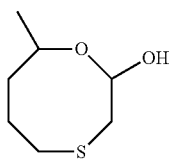 (6-11)
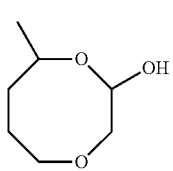 (6-12)
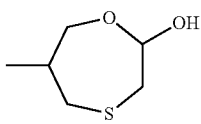 (6-13)
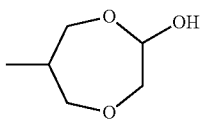 (6-14)
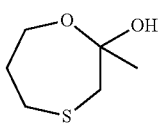 (6-15)
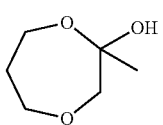 (6-16)
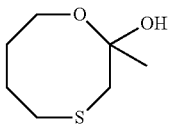 (6-17)
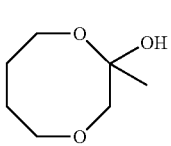 (6-18)
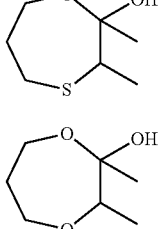 (6-19)
(6-20)
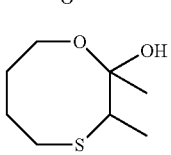 (6-21)
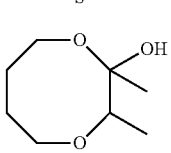 (6-22)
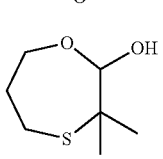 (6-23)
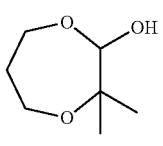 (6-24)

-continued

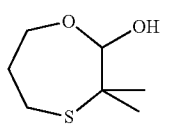
(6-25)

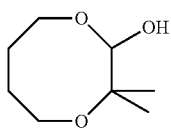
(6-26)

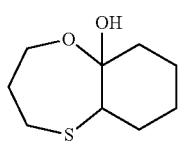
(6-27)

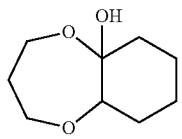
(6-28)

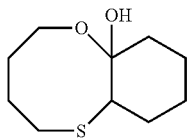
(6-29)

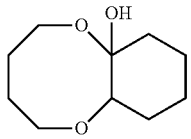
(6-30)

The cyclic alcohol (II-1) can be produced by a method shown below:

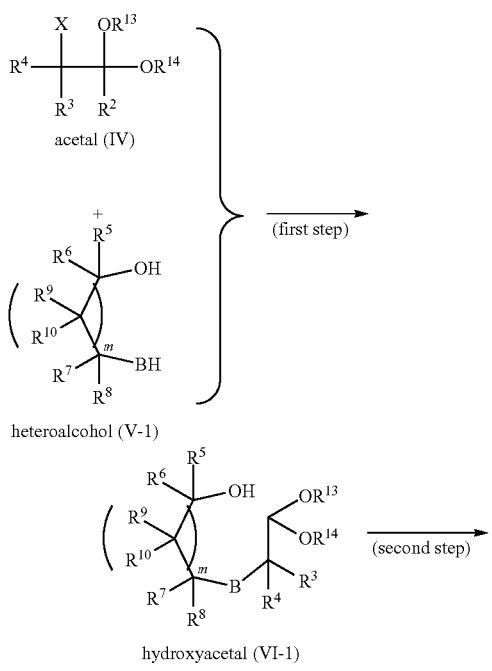

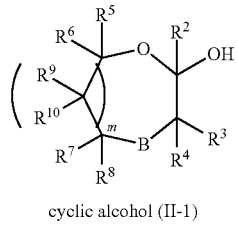

cyclic alcohol (II-1)

In the schemes shown above, $R^2$, $R^3$, $R^4$, $R^5$, $R^6$, $R^7$, $R^8$, $R^9$, $R^{10}$, $R^{13}$, $R^{14}$ and B are the same as defined above, and m represents 1 or 2.

A first step and a second step shown in the schemes described above shall be explained in order.

First Step:

The first step is a step in which an acetal (IV) is reacted with a heteroalcohol (V-1) in the presence of a base to produce a hydroxyacetal (VI-1).

The acetal (IV) is industrially available or can be produced by subjecting a corresponding α-haloketone compound or an α-haloaldehyde to normal acetalization.

The acetal (IV) include, for example, crotonaldehyde=dimethyl=acetal, crotonaldehyde=diethyl=acetal, bromoacetaldehyde=dimethyl=acetal, bromoacetaldehyde=diethyl=acetal, 1-bromo-2,2-dimethoxypropane, 1-iodo-2,2-diethoxypropane, 2-bromo-3,3-diethoxybutane, 1-chloro-2,2-dimethoxyhexane, 1-chloro-2,2-dimethoxyheptane, 1-chloro-2,2-dimethoxycyclopentane, 1-chloro-2,2-dimethoxycyclohexane, 1-bromo-2,2-dimethoxycycloheptane and the like, but they shall not specifically be restricted to the above compounds.

The heteroalcohol (V-1) includes, for example, 3-mercapto-1-butanol, 2-methyl-3-mercapto-1-propanol, 4-mercapto-2-butanol, 3-methyl-3-mercapto-1-butanol, 2,2-dimethyl-3-mercapto-1-propanol, 2-isopropyl-2-methyl-3-mercapto-1-propanol, 2-methyl-4-mercapto-2-butanol, 2-ethyl-2-methyl-3-mercapto-1-propanol, 1-mercapto-3-pentanol, 2-ethyl-3-mercapto-1-propanol, 3-mercapto-1-propanol, 4-mercapto-1-butanol, 5-mercapto-2-pentanol, 2-methyl-5-mercapto-2-pentanol, 4-mercapto-1-pentanol, 1,3-propanediol, 2-methyl-1,3-propanediol, 2,2-dimethyl-1,3-propanediol, 2-ethyl-2-methyl-1,3-propanediol, 2,2-diethyl-1,3-propanediol, 1,3-butanediol, 2,4-pentanediol, 2-methyl-2,4-pentanediol, 2,4-dimethyl-2,4-pentanediol, 2,2,4-trimethyl-1,3-pentanediol, 1,4-butanediol, 1,4-pentanediol, 2,5-dimethyl-2,5-hexanediol and the like, but it shall not specifically be restricted to them.

Among the heteroalcohols (V-1), the heteroalcohols in which B represents a sulfur atom are industrially available or can be produced by a method in which a corresponding halogenated alcohol is reacted with sodium hydrosulfide or potassium hydrosulfide and a method in which a corresponding halogenated alcohol is reacted with benzyl sulfide and then reduced.

Among the heteroalcohols (V-1), the heteroalcohols in which B represents an oxygen atom are industrially available or can be produced by substituting halogen atoms of corresponding dihalides and halogenated alcohols with hydroxyl groups in the presence of silver nitrate and water or reducing corresponding diketone compounds and diester compounds.

The base used in the first step may be any of an inorganic base and an organic base. The inorganic base includes, for example, alkali metal hydrides such as sodium hydride, potassium hydride and the like; alkali metal hydroxides such as sodium hydroxide, potassium hydroxide and the like; alkali metal carbonates such as sodium carbonate, potassium carbonate and the like. The organic base includes, for example, alkali metal salts of alcohols such as sodium methoxide, sodium ethoxide and the like; tertiary amines such as triethylamine, tributylamine, N,N-dimethylaniline, diazabicyclo[2.2.2]octane and the like; nitrogen-containing heterocyclic aromatic compounds such as pyridine, 4-(N,N-dimethylamino)pyridine and the like. They may be used alone or in a mixture of two or more kinds thereof.

A use amount of the base falls in a range of preferably 0.8 to 5 moles, more preferably 0.8 to 3 moles based on 1 mole of the heteroalcohol (V-1) from the viewpoints of an economical efficiency and easiness in after-treatment.

The first step can be carried out in the presence or the absence of a solvent. The solvent shall not specifically be restricted as long as the reaction is not inhibited, and it includes, for example, aliphatic hydrocarbons such as hexane, heptane, octane and the like; aromatic hydrocarbons such as toluene, xylene, cymene and the like; halogenated hydrocarbons such as methylene chloride, dichloroethane and the like; alcohols such as methanol, ethanol, n-propanol, 2-propanol, n-butanol and the like; ethers such as tetrahydrofuran, diisopropyl ether and the like. They may be used alone or in a mixture of two or more kinds thereof.

Further, the acetal (IV) or the heteroalcohol (V-1) can be used as a solvent-cum-reactant. When the acetal (IV) is used as a solvent-cum-reactant, a use amount thereof falls in a range of preferably 0.1 to 10 mass times, more preferably 0.1 to 5 mass times based on the heteroalcohol (V-1) from the viewpoints of an economical efficiency and easiness in after-treatment. When the heteroalcohol (V-1) is used as a solvent-cum-reactant, a use amount thereof falls in a range of preferably 0.1 to 10 mass times, more preferably 0.1 to 5 mass times based on the acetal (IV).

A reaction temperature in the first step is varied depending on the kinds of the acetal (IV), the heteroalcohol (V-1), the base and the solvent used, and it falls in a range of preferably 0 to 100° C.

A pressure in the first step shall not specifically be restricted and is preferably atmospheric pressure from the viewpoint of easiness in operation.

The targeted heteroalcohol (V-1) produced in the first step can be isolated and refined, for example, by removing salts produced in the reaction by filtering after finishing the reaction, concentrating the filtrate obtained and then distilling the concentrate. Ordinary separation and refining operations for organic compounds such as neutralization, extraction by solvents, distillation, column chromatography, recrystallization and the like can suitably be combined as well.

Second Step:

The second step is a step in which the hydroxyacetal (VI-1) produced in the first step is hydrolyzed and cyclized in the presence of an acid catalyst.

The acid catalyst includes, for example, carboxylic acids such as acetic acid, propionic acid, benzoic acid and the like; sulfonic acids such as benzenesulfonic acid, p-toluenesulfonic acid, 10-camphorsulfonic acid, methanesulfonic acid and the like; and mineral acids such as sulfuric acid, hydrochloric acid, phosphoric acid and the like.

A use amount of the acid catalyst falls in a range of preferably 0.0001 to 1 time mole, more preferably 0.001 to 0.1 time mole based on the hydroxyacetal (VI-1) from the viewpoints of an economical efficiency and easiness in after-treatment.

An amount of water used for hydrolysis in the second step is preferably 1 time mole or more based on the hydroxyacetal (VI-1), and it is preferably a large excess amount based on the hydroxyacetal (VI-1) from the viewpoint of enhancing a yield of the cyclic alcohol (II-1). It is more preferably 1 to 10000 times mole, more preferably 10 to 1000 times mole based on the hydroxyacetal (VI-1) from the viewpoints of an economical efficiency and easiness in after-treatment.

The second step can be carried out in the presence or the absence of a solvent. The solvent shall not specifically be restricted as long as the reaction is not inhibited, and it includes, for example, aliphatic hydrocarbons such as hexane, heptane, octane and the like; aromatic hydrocarbons such as toluene, xylene, cymene and the like; halogenated hydrocarbons such as methylene chloride, dichloroethane and the like; ethers such as diethyl ether, tetrahydrofuran, 1,4-dioxane, diisopropyl ether, 1,2-dimethoxyethane and the like. Further, water can be used as a solvent-cum-reactant.

When the solvent is used, a use amount thereof falls in a range of preferably 0.1 to 10 mass times, more preferably 0.1 to 5 mass times based on the hydroxyacetal (VI-1) from the viewpoints of an economical efficiency and easiness in after-treatment.

A reaction temperature in the second step is varied depending on the kinds of the hydroxyacetal (VI-1), the acid catalyst and the solvent, and it falls in a range of preferably 0 to 100° C.

A pressure in the second step is varied depending on the kinds of the hydroxyacetal (VI-1), the acid catalyst and the solvent, and it can be carried out under either atmospheric pressure or reduced pressure.

$R^{13}OH$ and $R^{14}OH$ (in the formulas, $R^{13}$ and $R^{14}$ are the same as defined above) which are alcohols originating in the hydroxyacetal (VI-1) are by-produced in the second step, and in order to enhance a yield of the targeted cyclic alcohol (II-1), the reaction is carried out preferably while removing the above alcohols to an outside of the system. A method for removing the above alcohols to an outside of the system is preferably a method in which the alcohols are removed by distillation by carrying out the reaction under reduced pressure from the viewpoint of easiness in the operation. A pressure in carrying out the reaction at reduced pressure is preferably 1.3 to 93.1 kPa, more preferably 6.7 to 53.2 kPa.

The reaction in the second step can be terminated by neutralizing the acid catalyst with a neutralizer or removing the acid catalyst from the reaction system.

The neutralizer includes, for example, alkali metal hydroxides such as sodium hydroxide, potassium hydroxide and the like; alkali metal carbonates such as sodium carbonate, potassium carbonate and the like; alkali metal hydrogencarbonates such as sodium hydrogencarbonate, potassium hydrogencarbonate and the like; tertiary amines such as triethylamine, tributylamine and the like; and nitrogen-containing heterocyclic aromatic hydrocarbons such as pyridine and the like.

When the neutralizer is used to terminate the reaction, a use amount of the neutralizer falls in a range of preferably 1 to 3 equivalents based on the acid catalyst from the viewpoints of an economical efficiency and easiness in after-treatment.

A method for terminating the reaction by removing the acid catalyst from the reaction system includes, for example, a method in which a reaction solution under reaction is suitably diluted with a suited reaction solvent and in which it is then washed with water or an alkaline aqueous solution. The solvent shall not specifically be restricted as long as the reaction is not inhibited, and esters such as methyl acetate, ethyl acetate, butyl acetate and the like in addition to the solvents described above which can be used in the second step are suitably used. A use amount of the above solvent falls in a range of preferably 0.1 to 10 mass times, more preferably 0.1 to 5 mass times based on a whole mass of the reaction solution from the viewpoints of an economical efficiency and easiness in after-treatment.

Also, the basic substance in the alkaline aqueous solution includes, for example, inorganic bases such as sodium hydroxide, potassium hydroxide, sodium carbonate, sodium hydrogencarbonate, potassium carbonate, potassium hydrogencarbonate and the like. When the alkaline aqueous solution is used, a use amount of the basic substance falls in a range of preferably 0.1 to 3 equivalents based on the acid catalyst from the viewpoints of an economical efficiency and easiness in after-treatment.

The cyclic alcohol (II-1) thus obtained can be separated and refined by carrying out suitably ordinary separation and refining operations for organic compounds such as extraction by solvents, distillation, column chromatography, recrystallization and the like in combination.

Polymer (VIII):

The polymer (VIII) is prepared by polymerizing a raw material containing the acrylic ester derivative (I) of the present invention, whereby it can be used as a component for a photoresist composition.

The polymer (VIII) is a polymer prepared by homopolymerizing the acrylic ester derivative (I) or a copolymer prepared by copolymerizing the acrylic ester derivative (I) with other polymerizable compounds, and it has a structural unit based on the acrylic ester derivative (I). Usually, a content of the structural unit based on the acrylic ester derivative (I) in the polymer shall not specifically be restricted and falls in a range of preferably 10 to 90 mole %, more preferably 20 to 80 mole % from the viewpoints of a solubility to a developer for a photoresist composition described later, a heat stability and a reduction of LWR. The specific examples of the structural unit based on the acrylic ester derivative (I) include units represented by the following formulas (7-1) to (7-22), but they shall not be restricted to these units.

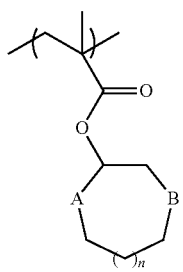

(7-1)

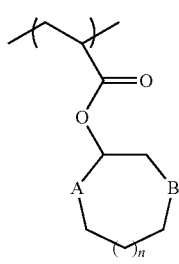

(7-2)

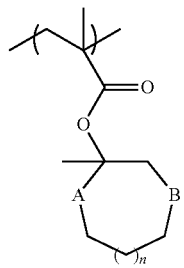

(7-3)

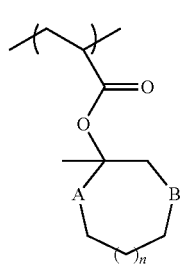

(7-4)

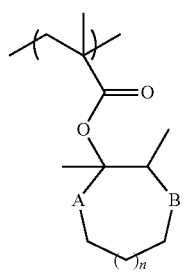

(7-5)

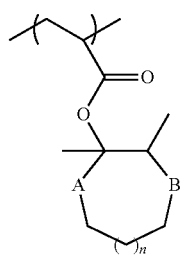

(7-6)

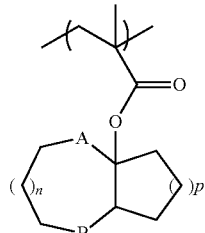

(7-7)

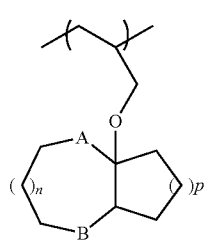

(7-8)

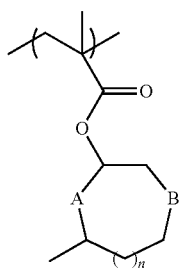 (7-9)
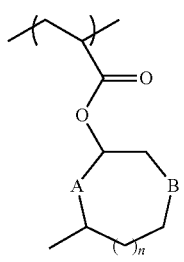 (7-10)
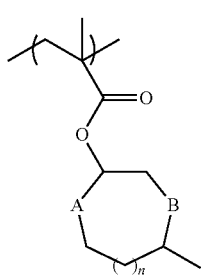 (7-11)
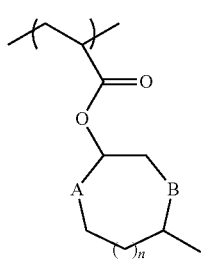 (7-12)
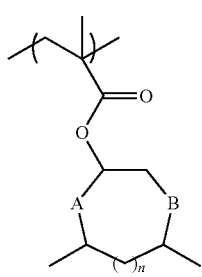 (7-13)
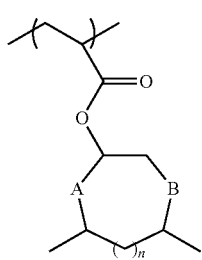 (7-14)
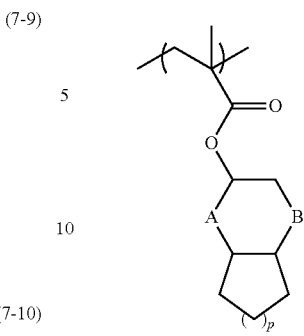 (7-15)
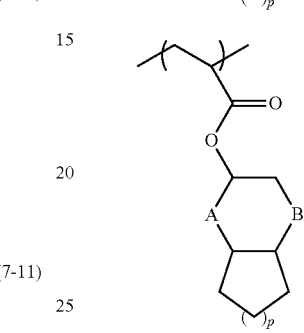 (7-16)
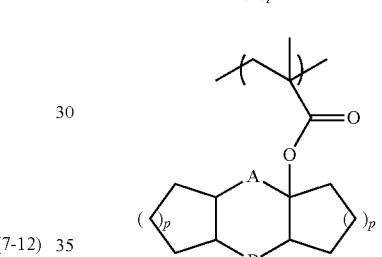 (7-17)
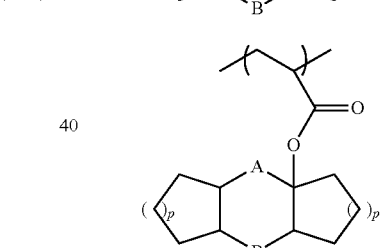 (7-18)
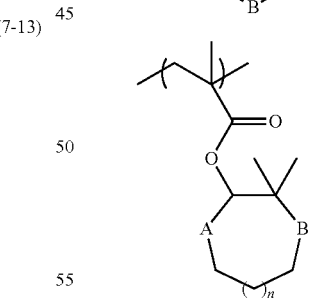 (7-19)
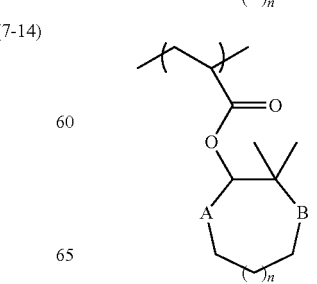 (7-20)

-continued (7-21)

[structure with A, B ring and cyclopentane, (p, n subscripts)]

(7-22)

[structure with A, B ring and cyclopentane, (p, n subscripts)]

The other polymerizable compounds (hereinafter referred to as the copolymerization monomer (VII)) which can be copolymerized with the acrylic ester derivative (I) include, for example, compounds (C-1) to (C-9) represented by the following chemical formulas:

(C-1)

[adamantane with $R^{17}$ and $OR^{18}$]

(C-2)

[adamantane with $OR^{18}$]

[adamantane with OH]

(C-3)

[adamantane with $OR^{18}$]

(C-4)

[norbornane lactone with $R^{18}O$ and $R^{19}$]

(C-5)

[tetrahydropyranone with $OR^{18}$]

-continued (C-6)

[γ-butyrolactone with $OR^{18}$]

(C-7)

[maleic anhydride]

(C-8)

[norbornene]

(C-9)

$R^{18}—O—R^{21}$ (wherein $R^{17}$ represents a hydrogen atom or an alkyl group having 1 to 3 carbon atoms; $R^{18}$ represents a polymerizable group; $R^{19}$ represents a hydrogen atom or —$COOR^{20}$, and $R^{20}$ represents an alkyl group having 1 to 3 carbon atoms; and $R^{21}$ represents an alkyl group or a cycloalkyl group in which a carbon atom forming a ring may be substituted with an oxygen atom), but they shall not specifically be restricted to these compounds.

In the copolymerization monomer (VII), the alkyl group having 1 to 3 carbon atoms each represented independently by $R^{17}$ and $R^{20}$ includes methyl, ethyl, n-propyl and isopropyl. The alkyl group represented by $R^{21}$ includes, for example, an alkyl group having 1 to 8 carbon atoms such as methyl, ethyl, n-propyl, isopropyl, n-butyl, isobutyl, s-butyl, t-butyl and the like. The cycloalkyl group represented by $R^{21}$ in which a carbon atom forming a ring may be substituted with an oxygen atom includes cyclopentyl, cyclohexyl, 1-methylcyclohexyl, cyclooctyl, tetrahydropyran-2-yl, 4-methyltetrahydropyran-4-yl and the like. The polymerizable group represented by $R^{18}$ includes, for example, acryloyl, methacryloyl, 2-trifluoromethylacryloyl, vinyl, crotonoyl and the like.

$R^{17}$ is preferably a hydrogen atom, methyl, ethyl or isopropyl. $R^{18}$ is preferably acryloyl or methacryloyl. $R^{19}$ is preferably a hydrogen atom. $R^{21}$ is preferably an alkyl group having 1 to 8 carbon atoms.

The other polymerizable compounds which can be copolymerized with the acrylic ester derivative (I) are preferably the compounds (C-1), (C-2), (C-4), (C-5), (C-6) and (C-9), more preferably the compounds (C-2), (C-4) and (C-6).

Production Process for the Polymer (VIII):

The polymer (VIII) can be produced by a radical polymerization according to a conventional method. In particular, a living radical polymerization can be listed as a method for synthesizing the polymer having a narrow molecular weight distribution. In a conventional radical polymerization method, at least one of the acrylic ester derivatives (I) according to necessity and at least one of the copolymerization monomers (VII) according to necessity are polymerized in the presence of a radical initiator, a solvent and, if necessary, a chain transfer agent.

The above radical polymerization method shall be explained below.

A method for carrying out the radical polymerization shall not specifically be restricted, and capable of being used are conventional methods used in producing, for example, acrylic polymers, such as a solution polymerization method, an emulsion polymerization method, a suspension polymerization method, a bulk polymerization method and the like.

The radical initiator includes, for example, hydroperoxides such as t-butyl hydroperoxide, cumene hydroperoxide and the like; dialkyl peroxides such as di-t-butyl peroxide, t-butyl-α-cumyl peroxide, di-α-cumyl peroxide and the like; diacyl peroxides such as benzoyl peroxide, diisobutyryl peroxide and the like; and azo compounds such as 2,2'-azobisisobutyronitrile, dimethyl-2,2'-azobisisobutylate and the like.

A use amount of the radical initiator can suitably be selected according to the polymerization conditions such as the kinds and the use amounts of the acrylic ester derivative (I), the copolymerization monomer (VII), the chain transfer agent and the solvent which are used for the polymerization reaction and the polymerization temperature and the like, and it falls in a range of usually 0.005 to 0.2 mole, preferably 0.01 to 0.15 mole based on 1 mole of the whole polymerizable compounds (showing a total amount of the acrylic ester derivative (I) and the copolymerization monomer (VII), and hereinafter the same shall apply).

The chain transfer agent includes, for example, thiols such as dodecanethiol, mercaptoethanol, mercaptopropanol, mercaptoacetic acid, mercaptopropionic acid and the like. They may be used alone or in a mixture of two or more kinds thereof.

When the chain transfer agent is used, a use amount thereof falls in a range of usually 0.005 to 0.2 mole, preferably 0.01 to 0.15 mole based on 1 mole of the whole polymerizable compounds.

The present radical polymerization is carried out usually in the presence of a solvent. The solvent shall not specifically be restricted as long as the reaction is not inhibited, and it includes, for example, glycol ethers such as propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether and the like; esters such as ethyl lactate, methyl 3-methoxypropionate, methyl acetate, ethyl acetate, propyl acetate and the like; ketones such as acetone, methyl ethyl ketone, methyl isopropyl ketone, methyl isobutyl ketone, methyl amyl ketone, cyclopentanone, cyclohexanone and the like; and ethers such as diethyl ether, diisopropyl ether, dibutyl ether, tetrahydrofuran, 1,4-dioxane and the like. They may be used alone or in a mixture of two or more kinds thereof.

A use amount of the solvent falls in a range of usually 0.5 to 20 parts by mass based on 1 part by mass of the whole polymerizable compounds, and it falls in a range of preferably 1 to 10 parts by mass from the viewpoint of an economical efficiency.

A reaction temperature in the radical polymerization falls usually in a range of preferably 40 to 150° C., and it falls in a range of more preferably 60 to 120° C. from the viewpoint of a stability of the polymer (VIII) produced.

A reaction time in the radical polymerization is varied according to the polymerization conditions such as the kinds and the use amounts of the acrylic ester derivative (I), the copolymerization monomer (VII), the initiator and the solvent, the polymerization temperature and the like, and it falls usually in a range of preferably 30 minutes to 48 hours, more preferably 1 hour to 24 hours.

The polymer (VIII) thus obtained can be isolated by ordinary operation such as reprecipitation.

A solvent used in the operation of the reprecipitation described above includes, for example, aliphatic hydrocarbons such as pentane, hexane and the like; alicyclic hydrocarbons such as cyclohexane and the like; aromatic hydrocarbons such as benzene, xylene and the like; halogenated hydrocarbons such as methylene chloride, chloroform, chlorobenzene, dichlorobenzene and the like; nitrated hydrocarbons such as nitromethane and the like; nitriles such as acetonitrile, benzonitrile and the like; ethers such as diethyl ether, diisopropyl ether, tetrahydrofuran, 1,4-dioxane and the like; ketones such as acetone, methyl ethyl ketone and the like; carboxylic acids such as acetic acid and the like; esters such as ethyl acetate, butyl acetate and the like; carbonates such as dimethyl carbonate, diethyl carbonate, ethylene carbonate and the like; alcohols such as methanol, ethanol, propanol, isopropyl alcohol, butanol and the like; water and the like. They may be used alone or in a mixture of two or more kinds thereof.

A use amount of the solvent is varied depending on the kind of the polymer (VIII) and the kind of the solvent, and it falls usually in a range of preferably 0.5 to 100 parts by mass based on 1 part by mass of the polymer (VIII); and it falls in a range of more preferably 1 to 50 parts by mass from the viewpoint of an economical efficiency.

The polymer (VIII) thus isolated can be dried by vacuum drying and the like.

The polymer (VIII) obtained by the method described above includes, for example, polymers represented by the following chemical formulas (8-1) to (8-135) and (9-1) to (9-182) (wherein $R^{22}$ to $R^{52}$ each represent independently a hydrogen atom, methyl or trifluoromethyl; a, b, c, d and e represent the mole ratios of the respective repetitive units; a+b is equal to 1, and c+d+e is equal to 1), but it shall not be restricted to these polymers.

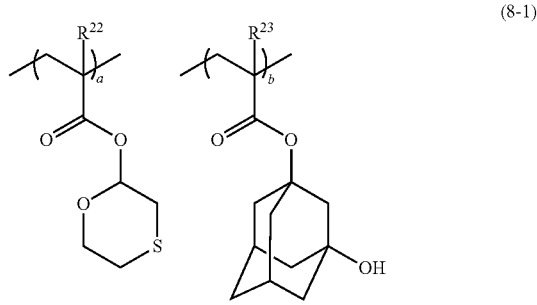

(8-1)

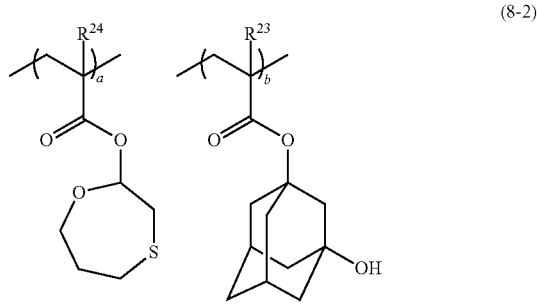

(8-2)

(8-3)
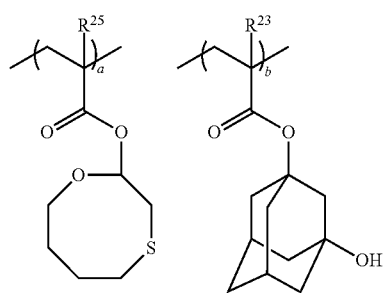
(8-4)
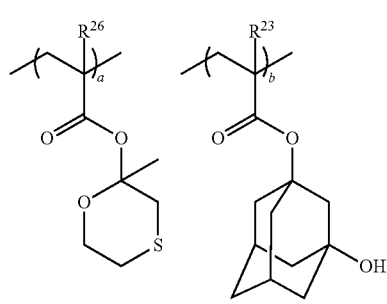
(8-5)
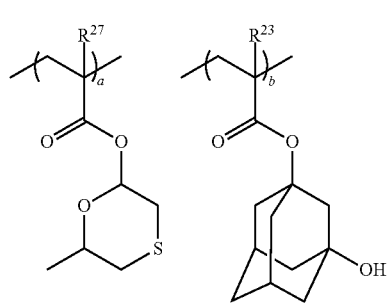
(8-6)
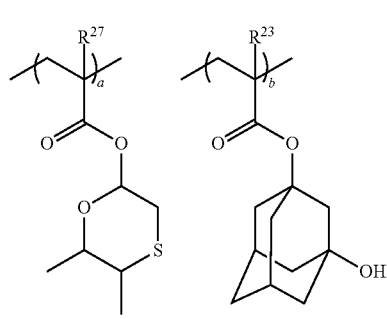
(8-7)
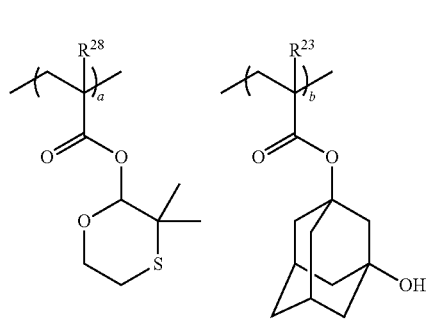
(8-8)
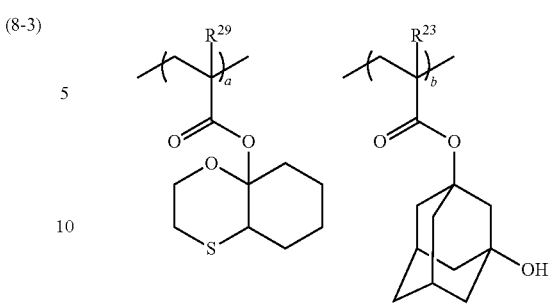
(8-9)
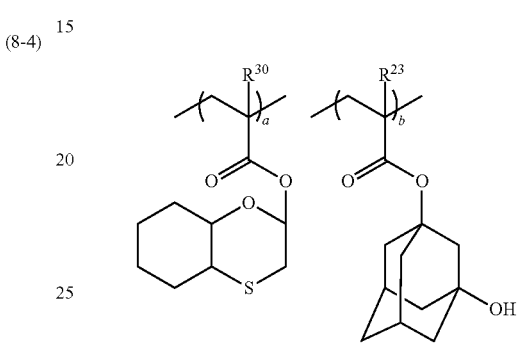
(8-10)
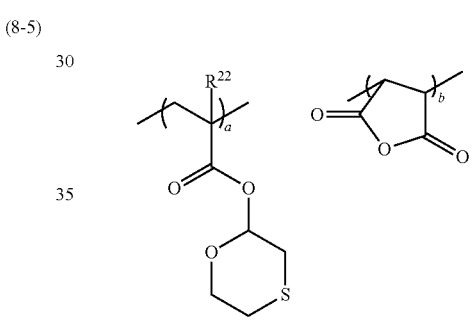
(8-11)
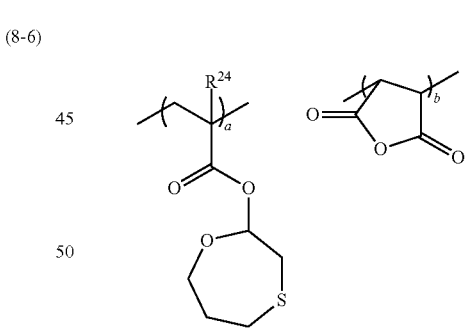
(8-12)
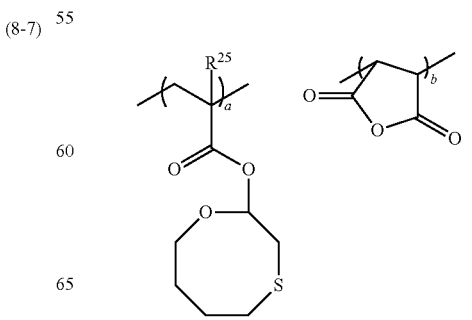

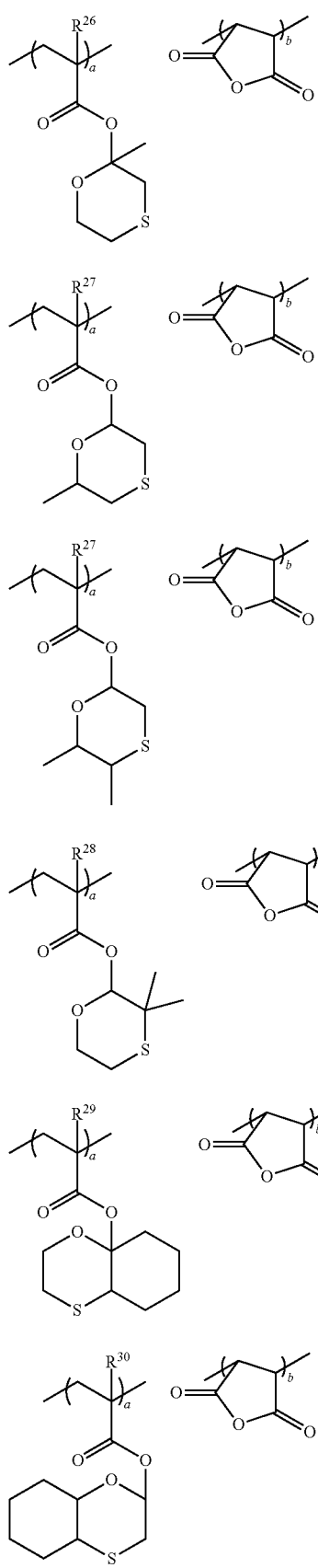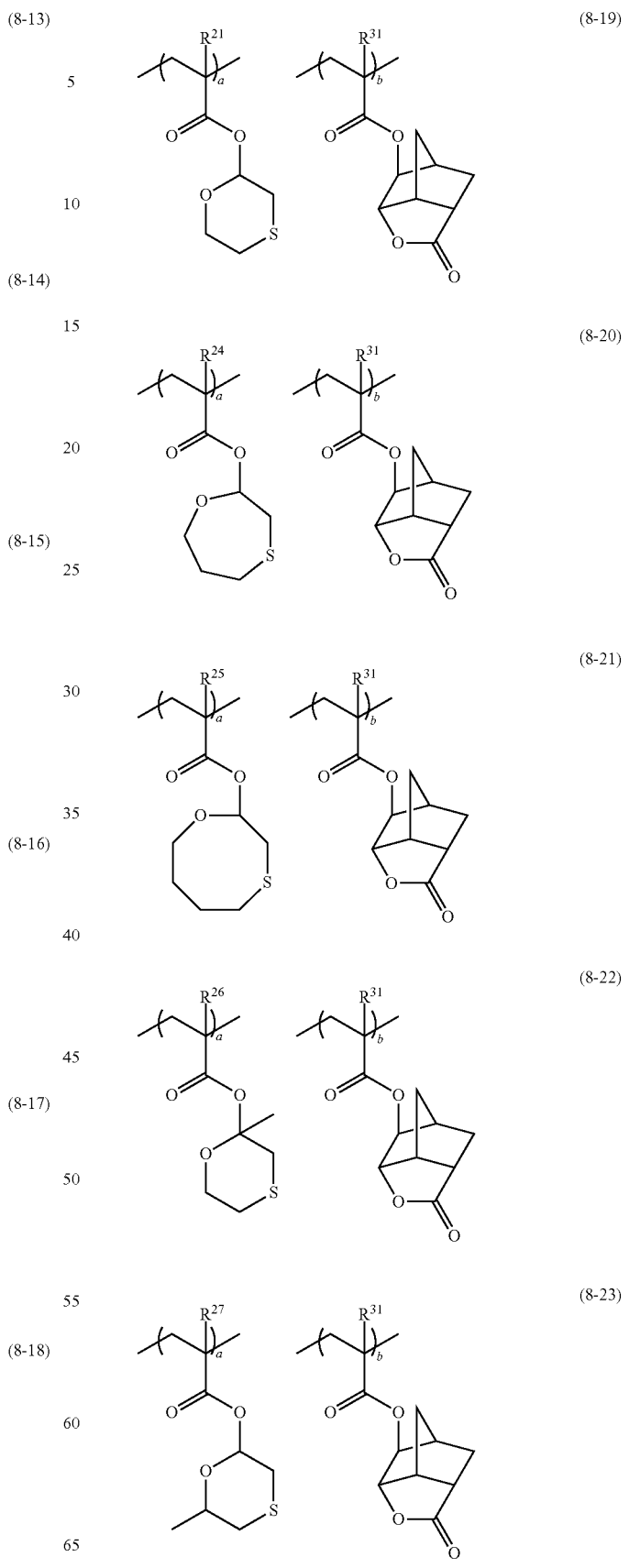

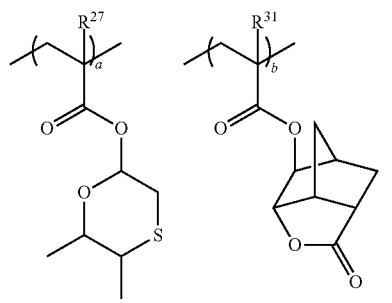
(8-24)
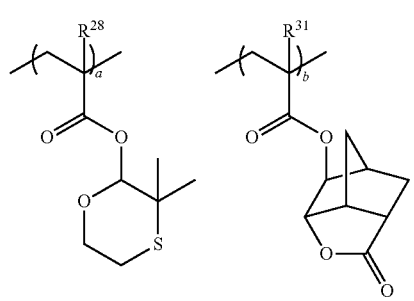
(8-25)
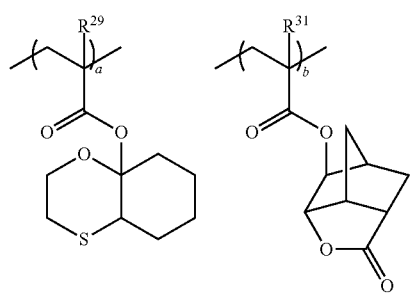
(8-26)
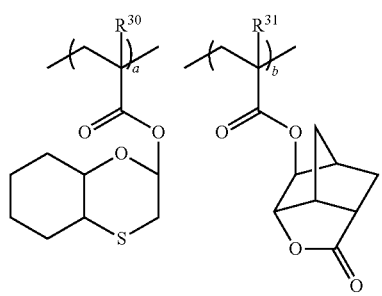
(8-27)
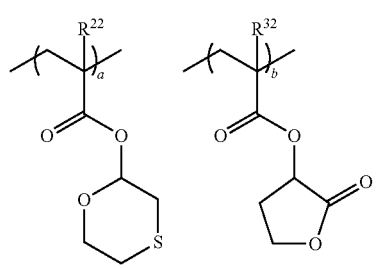
(8-28)
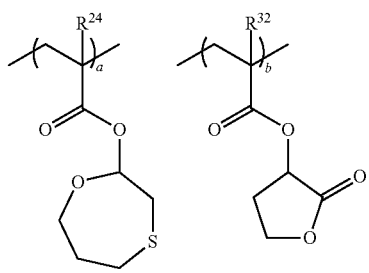
(8-29)
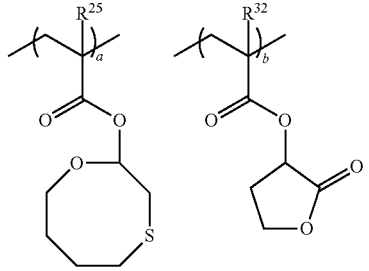
(8-30)
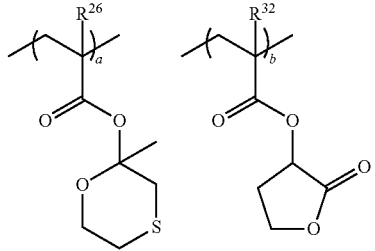
(8-31)
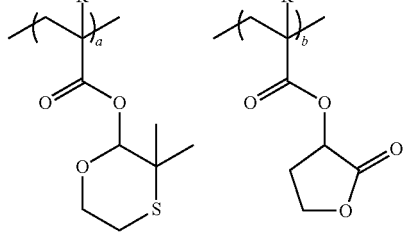
(8-32)
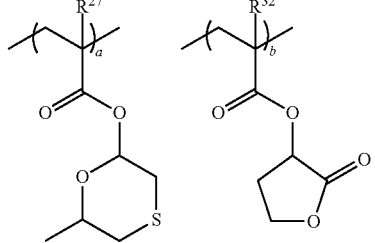
(8-33)
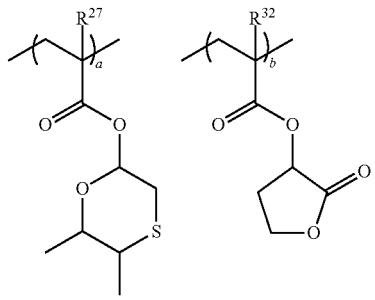
(8-34)

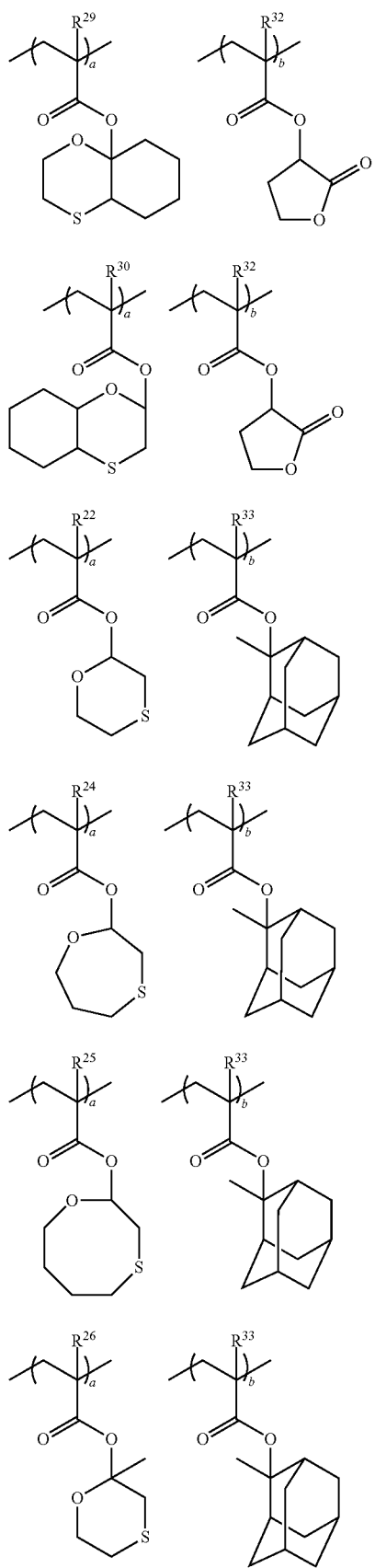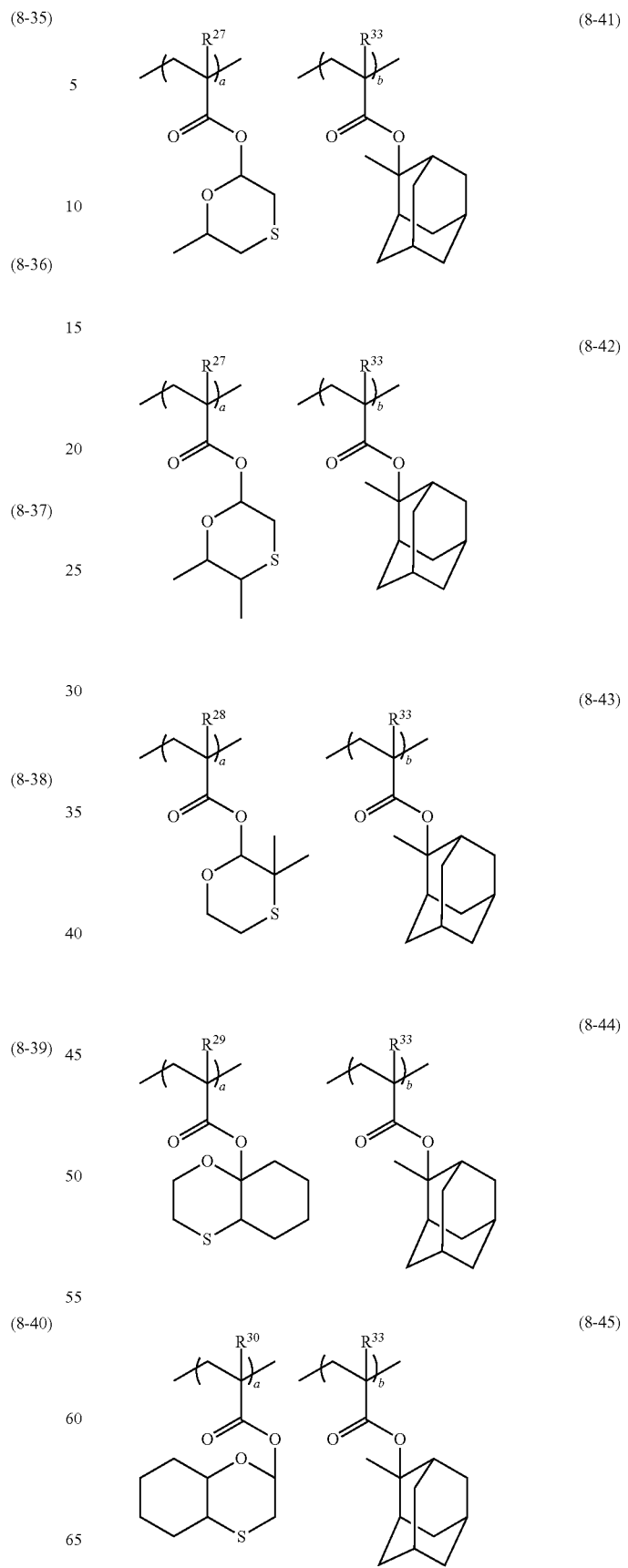

(8-46) 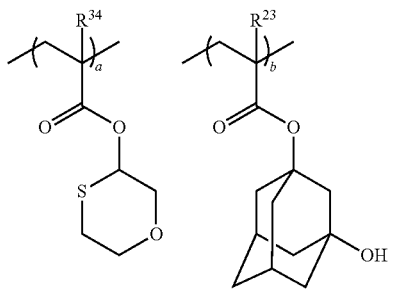
(8-47) 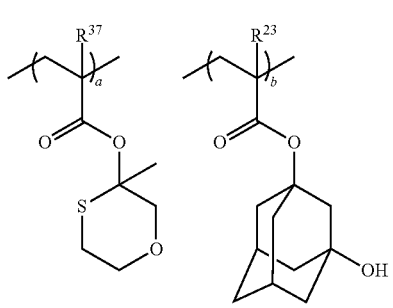
(8-48) 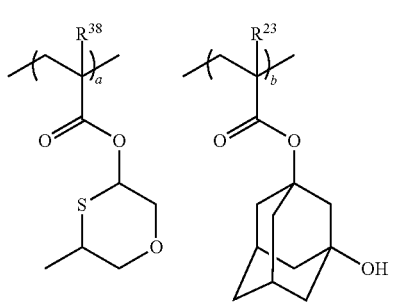
(8-49)
(8-50)
(8-51) 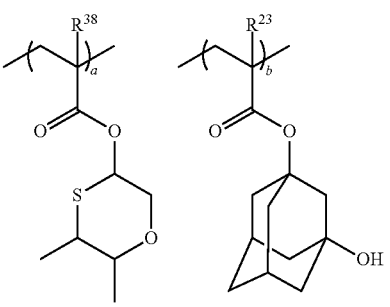
(8-52) 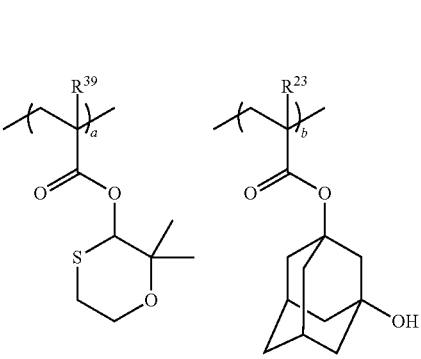
(8-53) 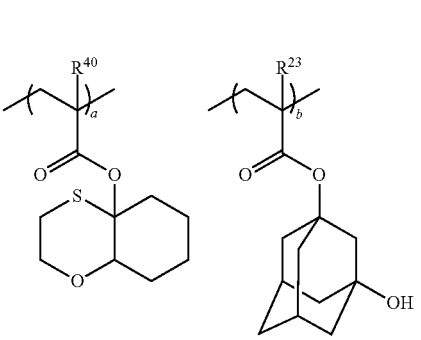
(8-54) 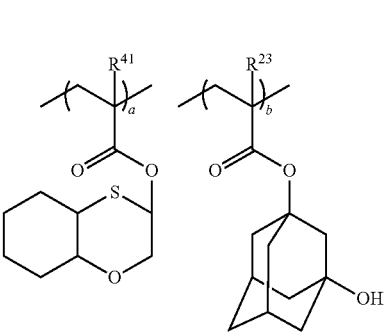
(8-55) 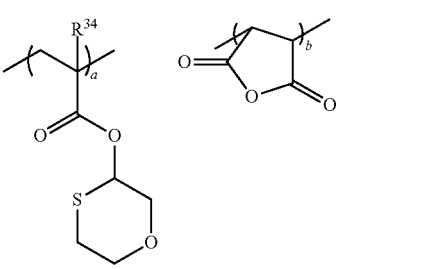

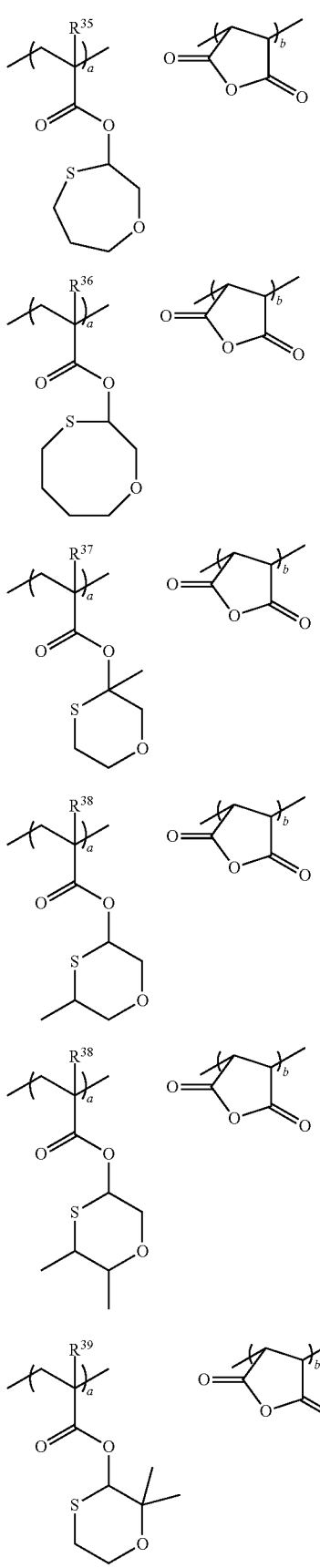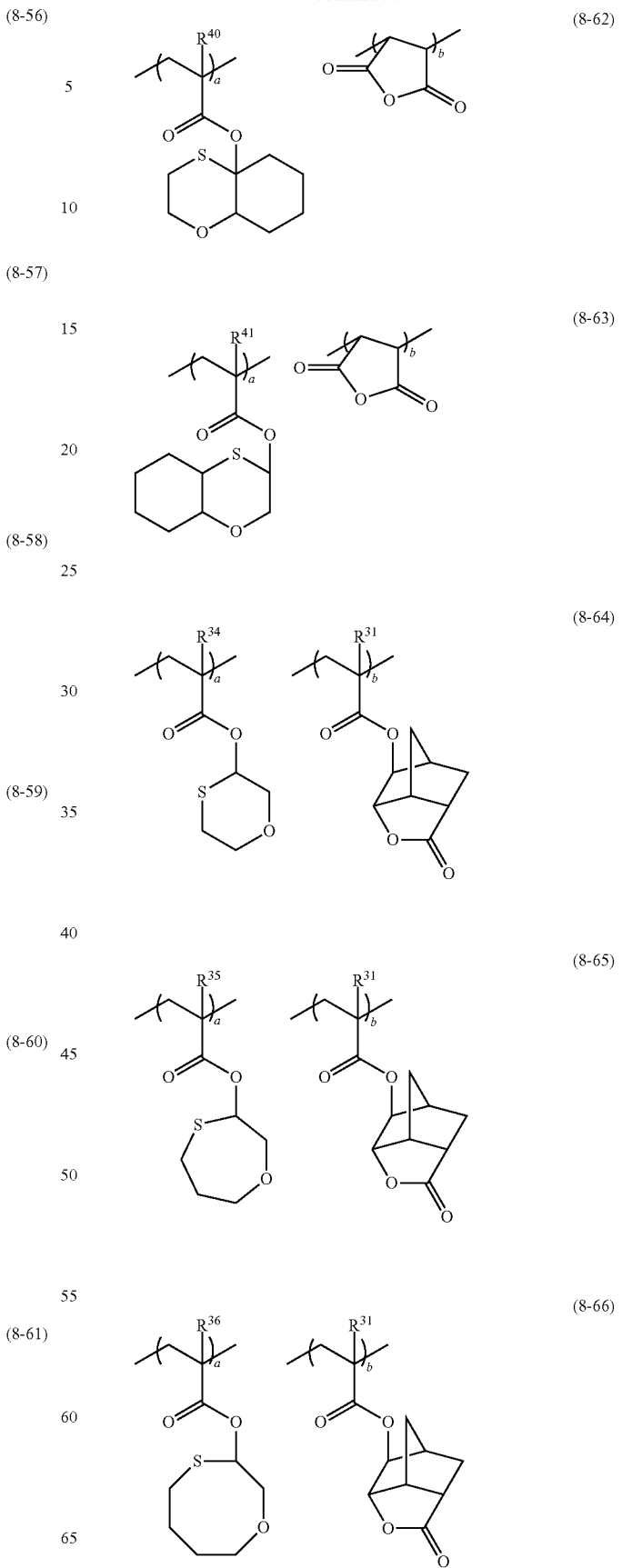

(8-67) 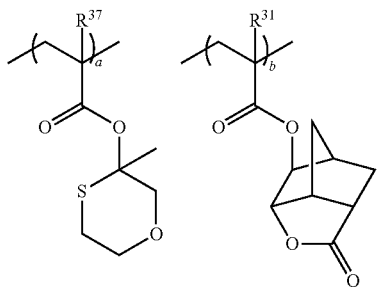
(8-68) 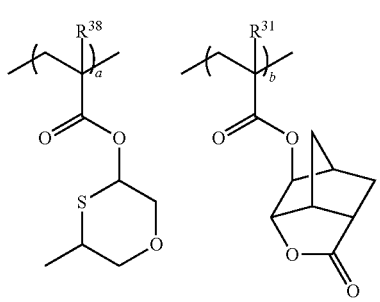
(8-69) 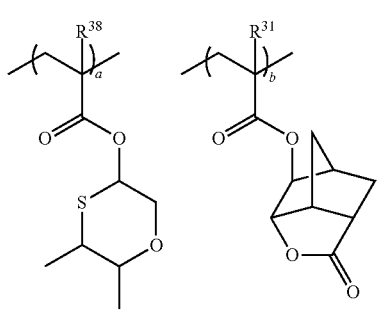
(8-70) 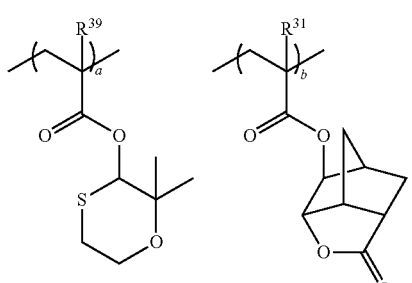
(8-71) 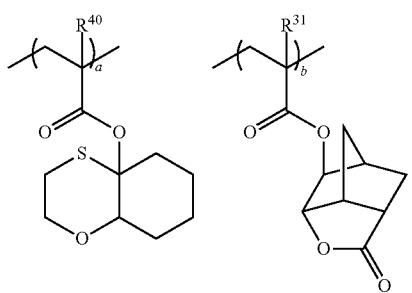
(8-72) 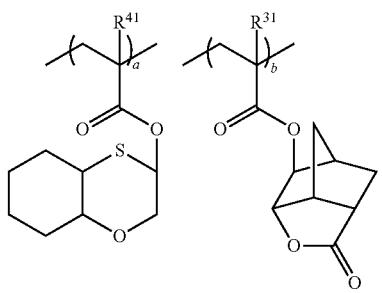
(8-73) 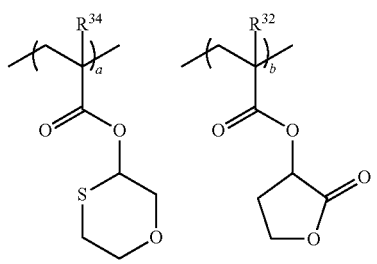
(8-74) 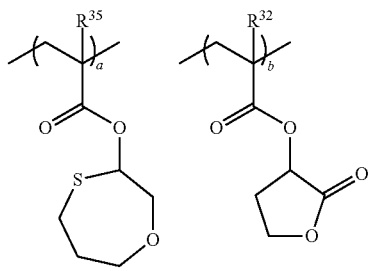
(8-75) 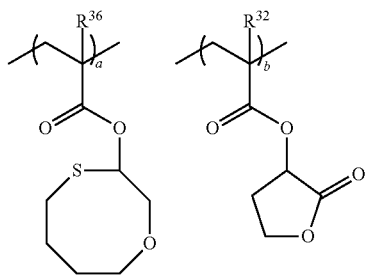
(8-76) 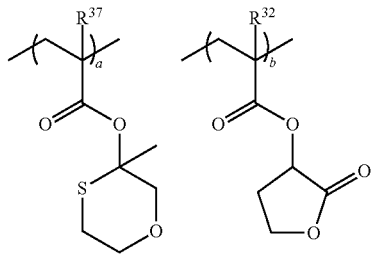
(8-77) 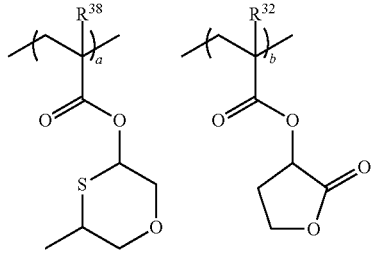

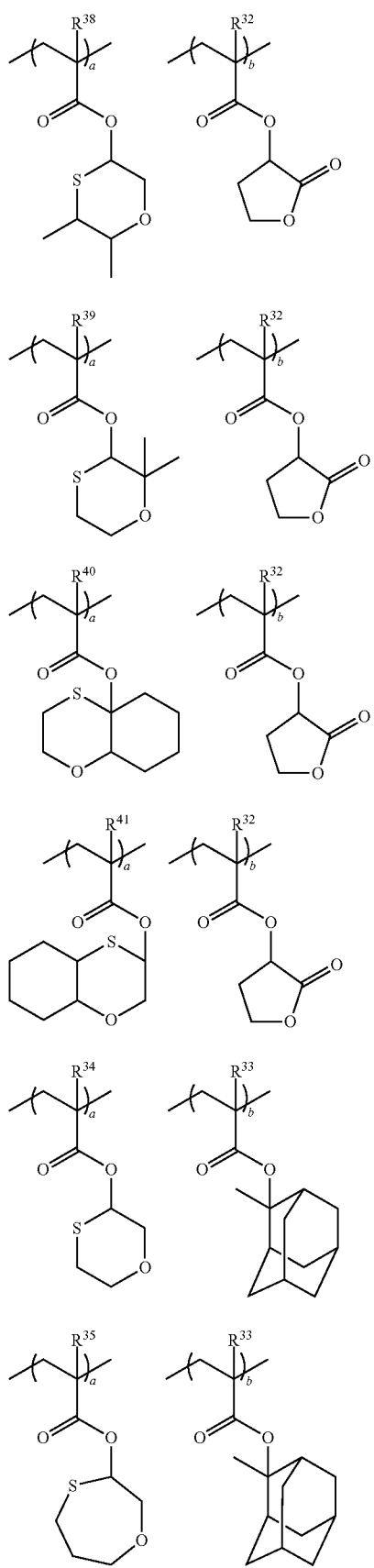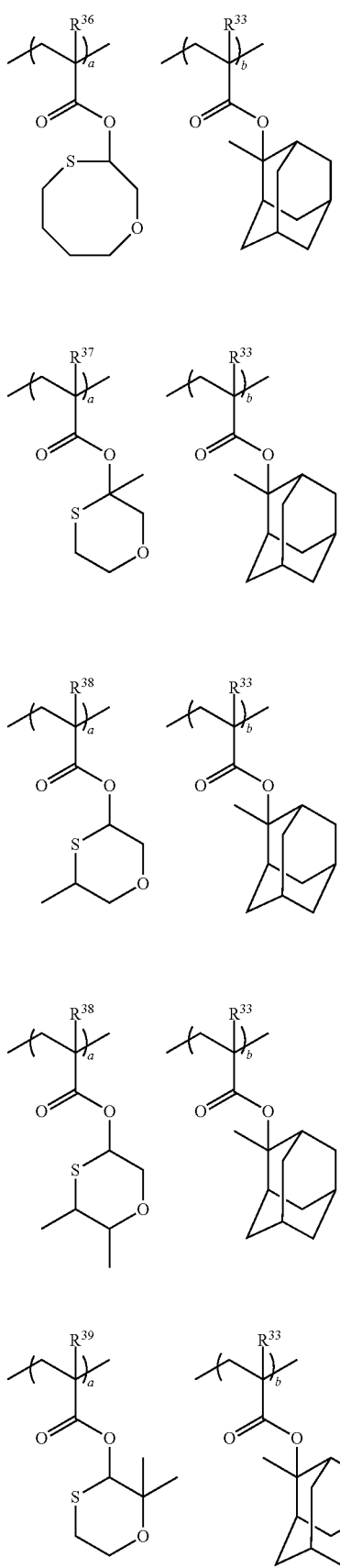

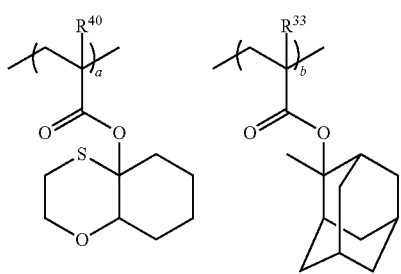 (8-89)
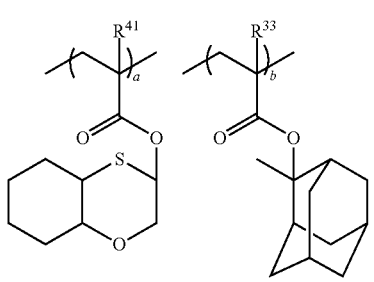 (8-90)
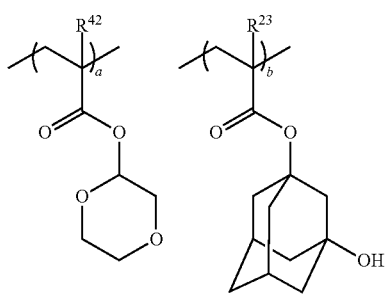 (8-91)
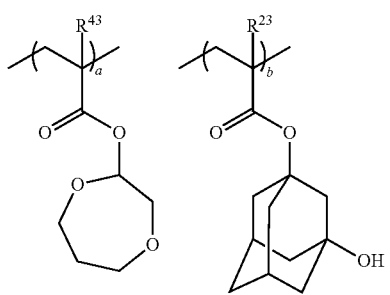 (8-92)
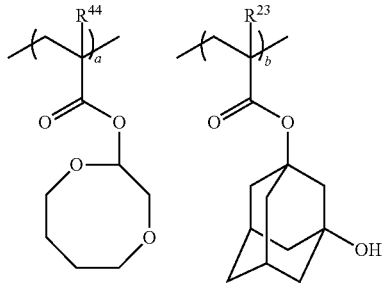 (8-93)
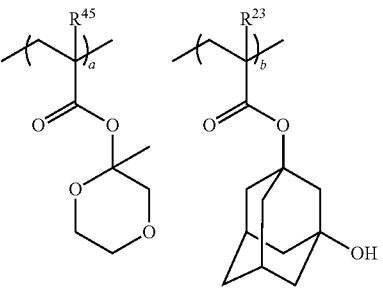 (8-94)
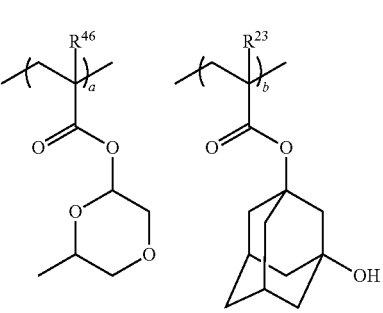 (8-95)
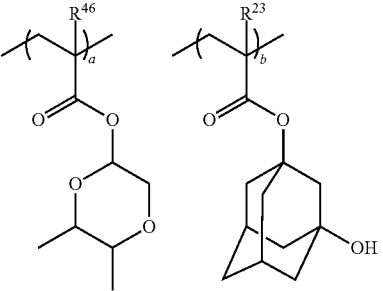 (8-96)
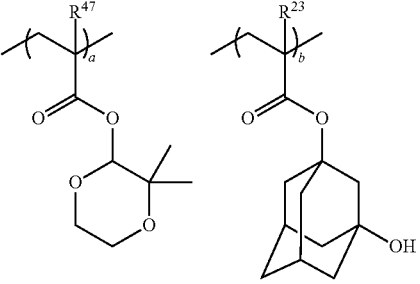 (8-97)
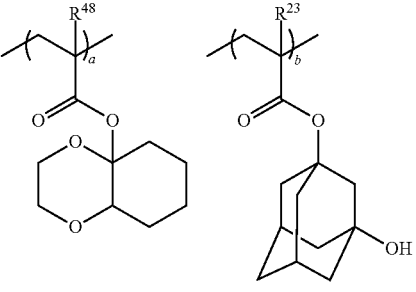 (8-98)

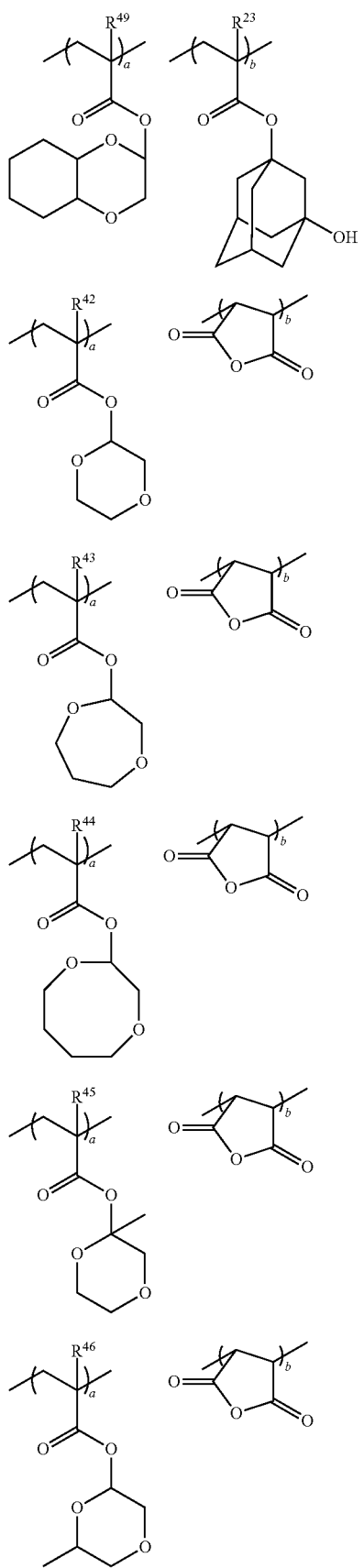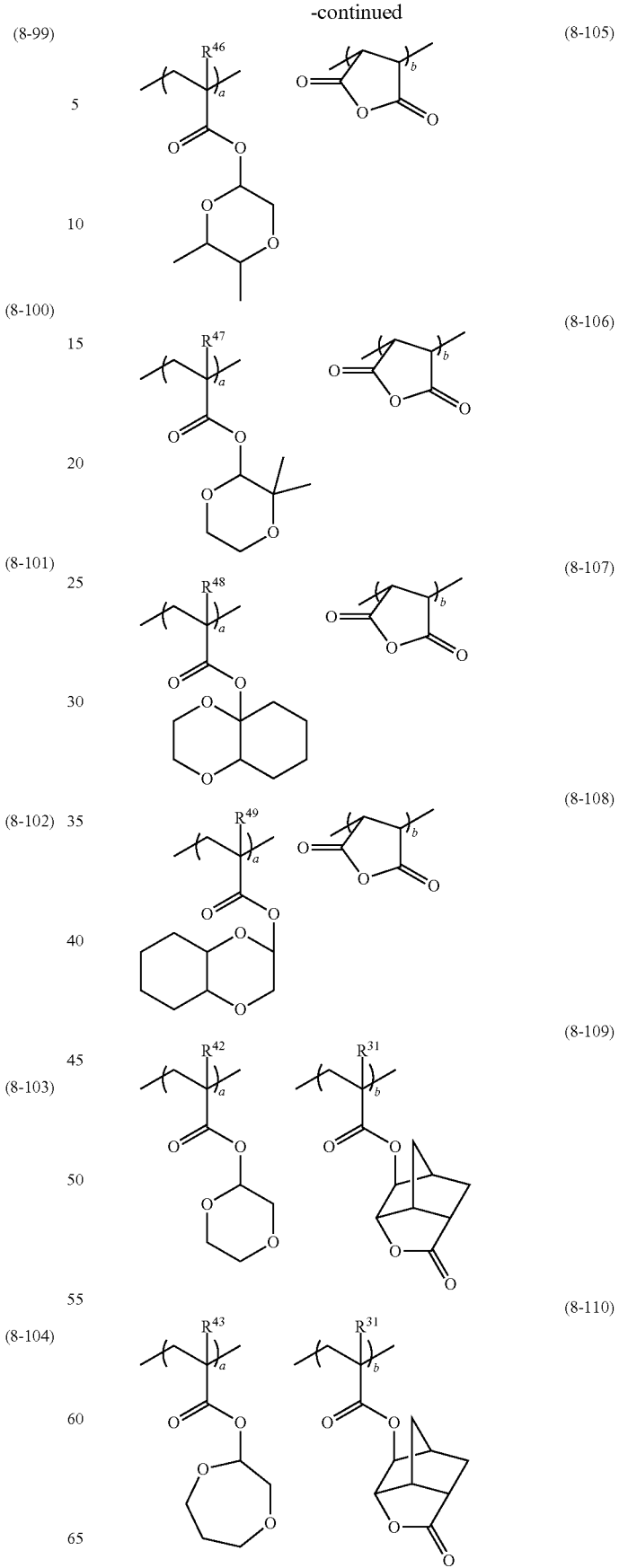

(8-111) 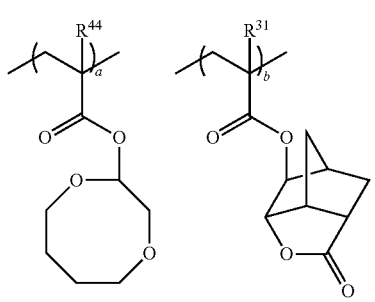
(8-112) 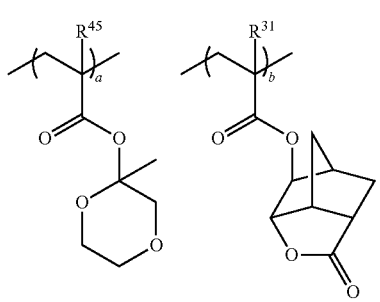
(8-113) 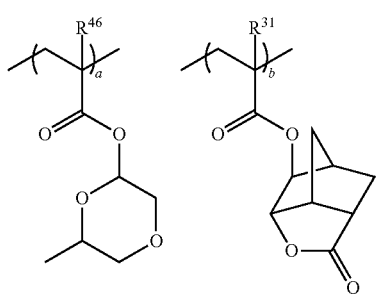
(8-114) 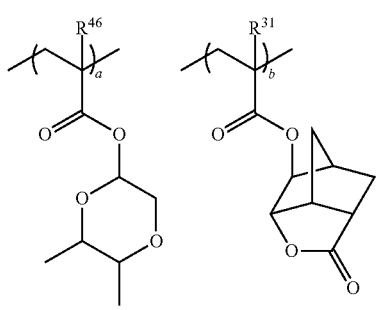
(8-115) 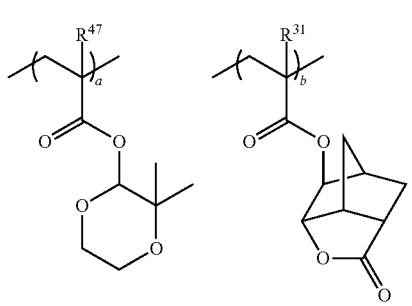
(8-116) 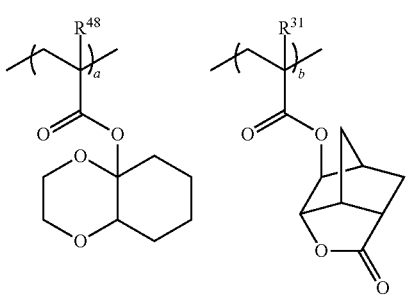
(8-117) 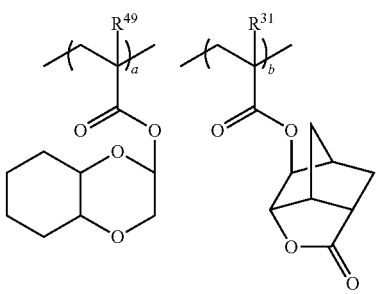
(8-118) 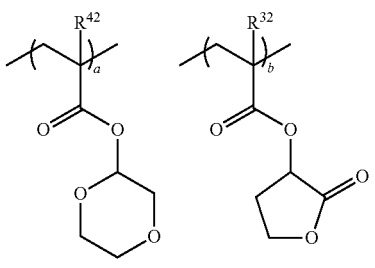
(8-119) 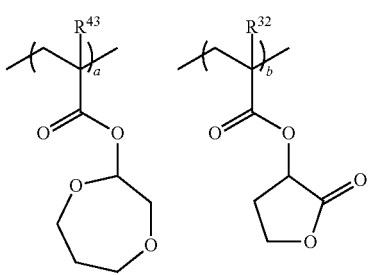
(8-120) 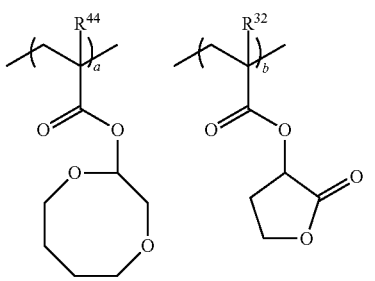

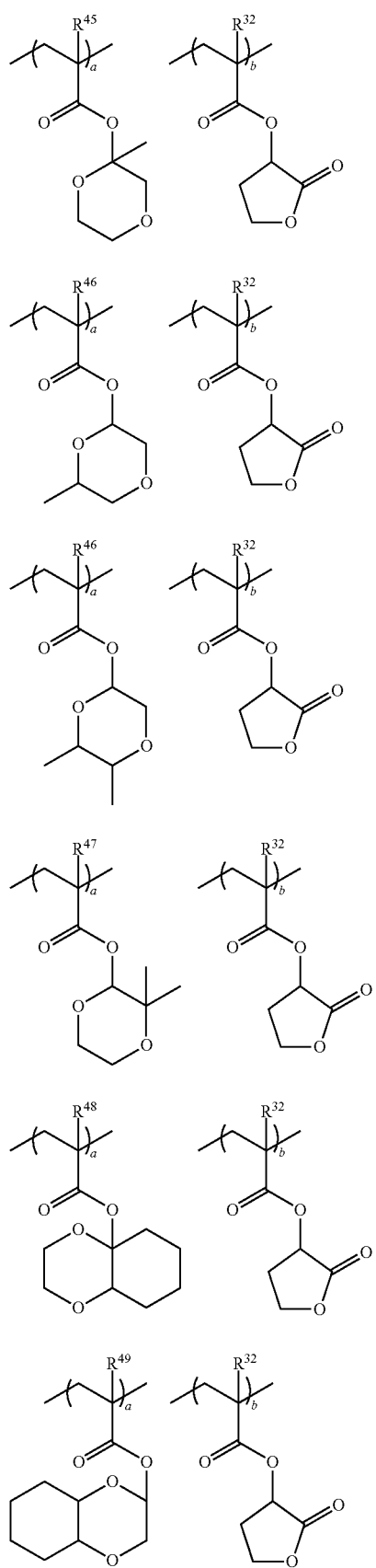

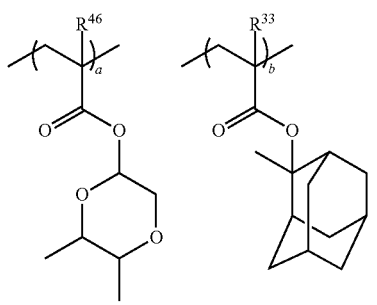
(8-132)
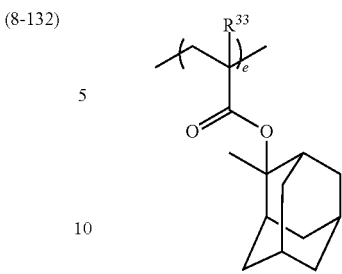
(8-133)
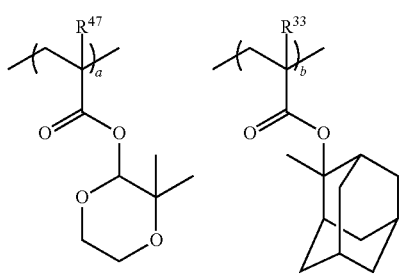
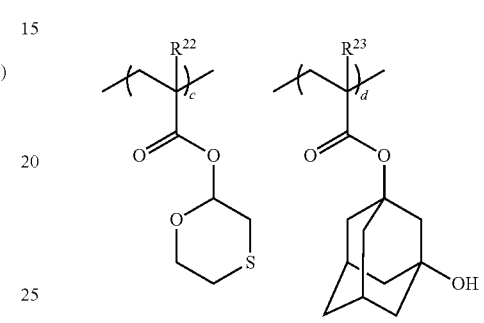
(9-2)
(8-134)
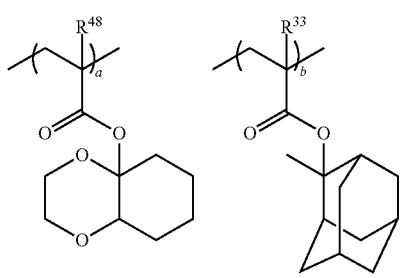
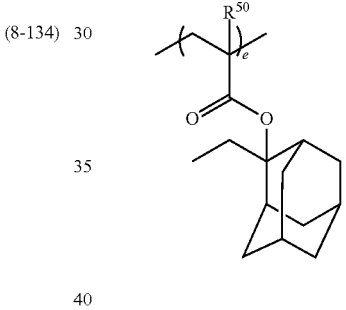
(8-135)
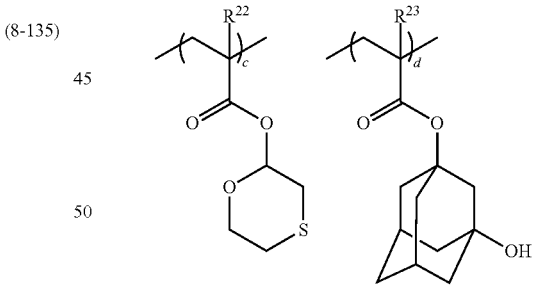
(9-3)
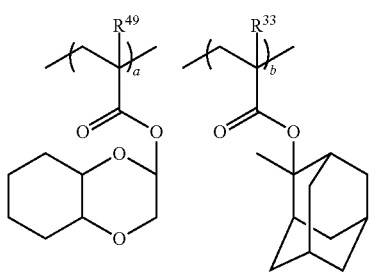
(9-1)
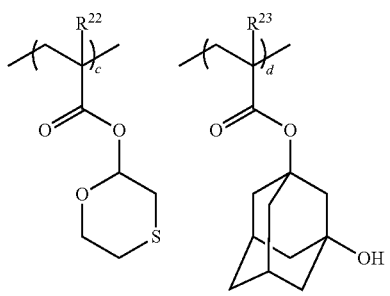
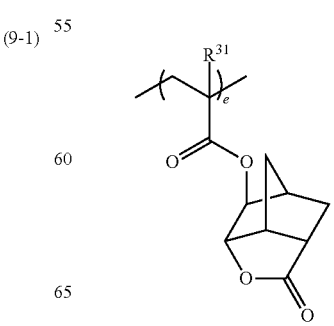

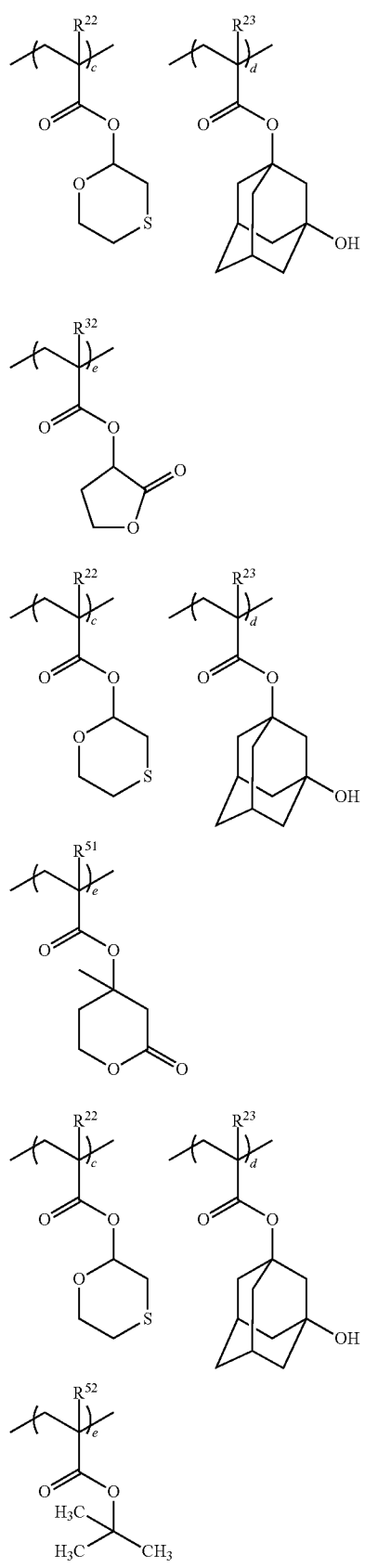
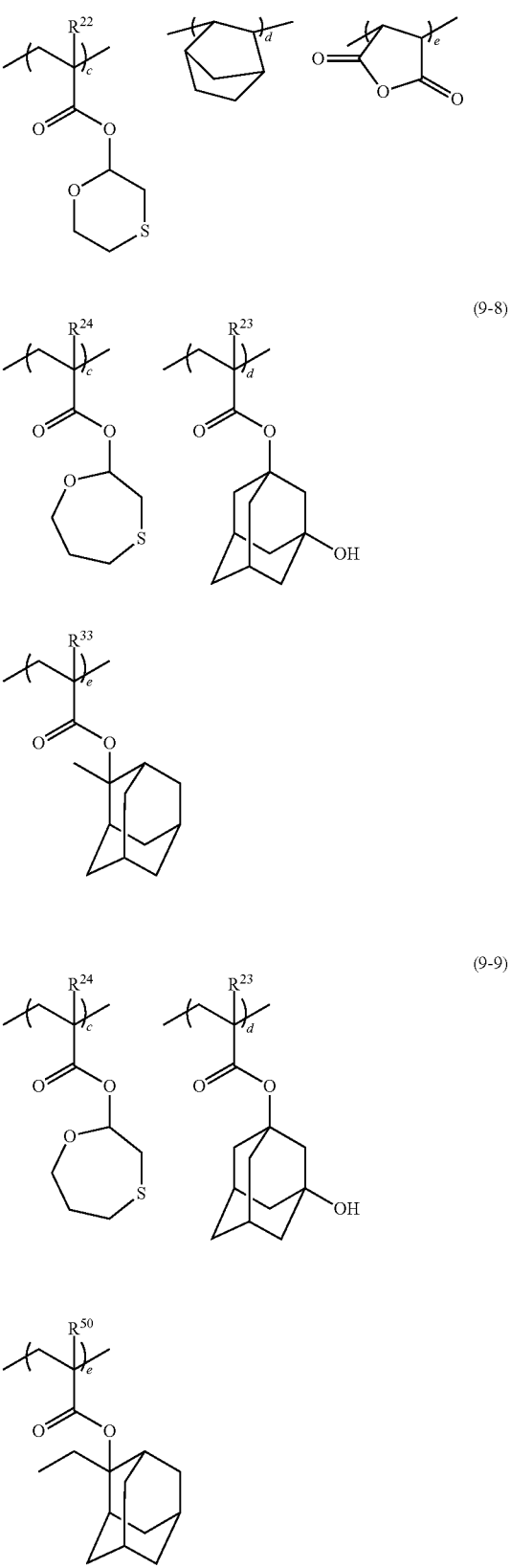

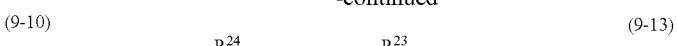
(9-10)
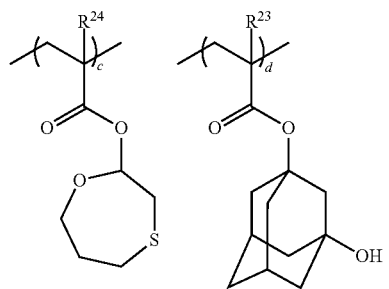
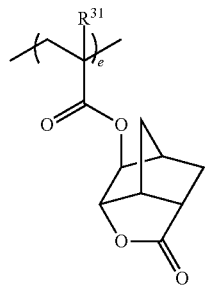
(9-11)
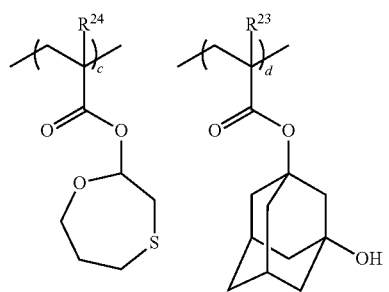
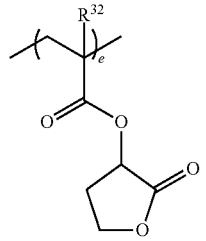
(9-12)
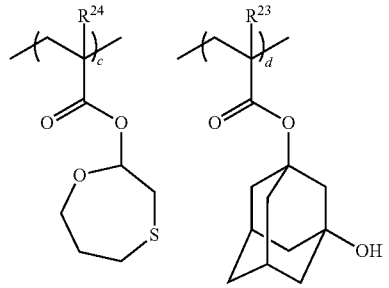
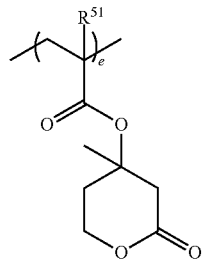
(9-13)
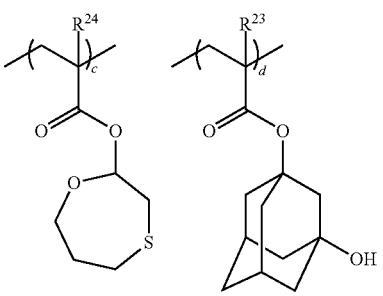
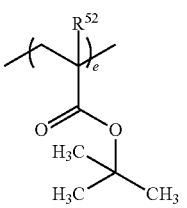
(9-14)
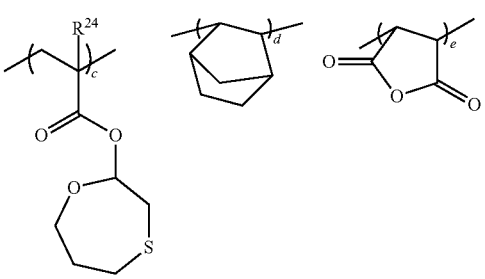
(9-15)
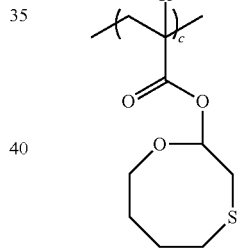
(9-16)
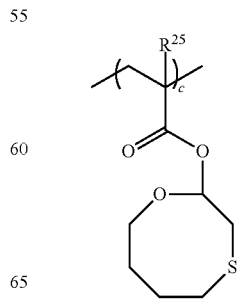

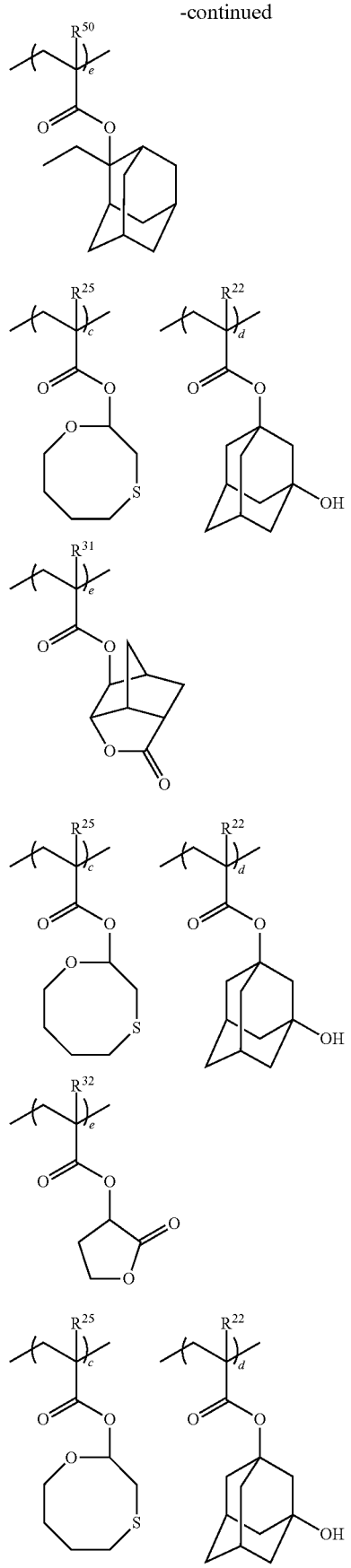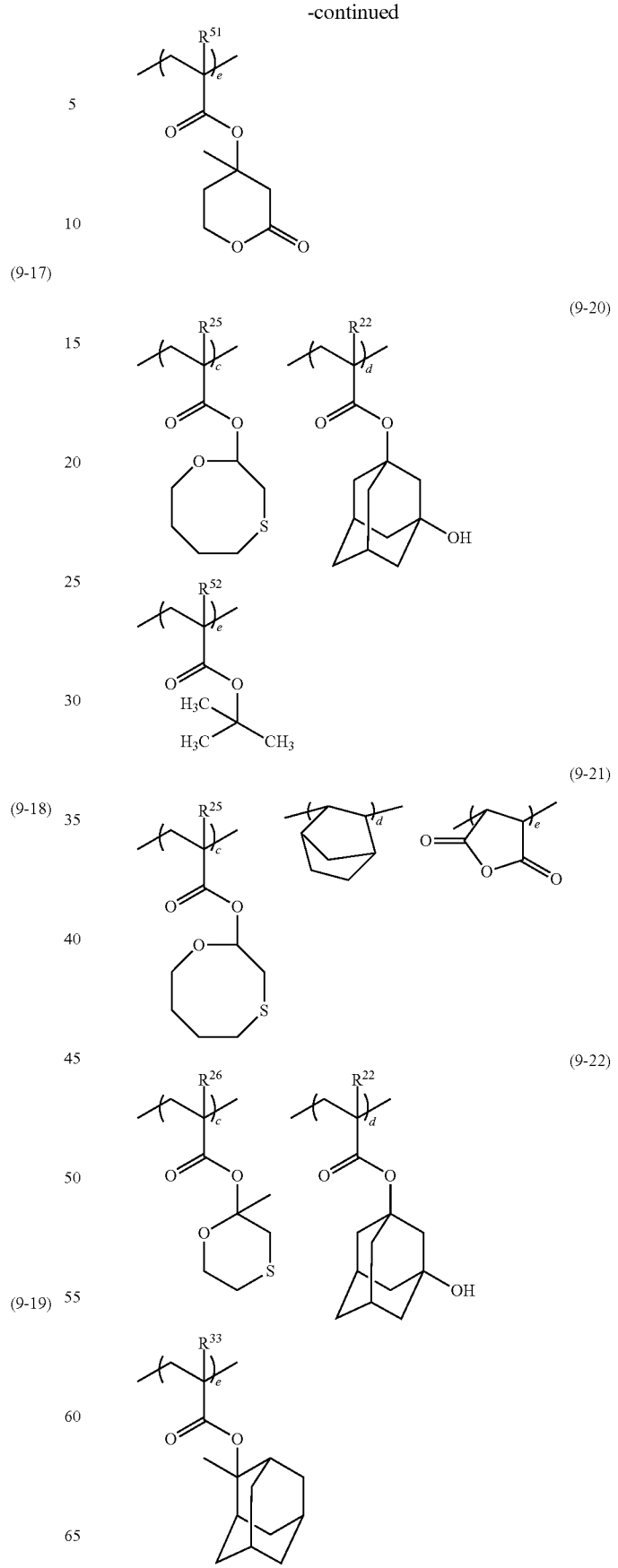

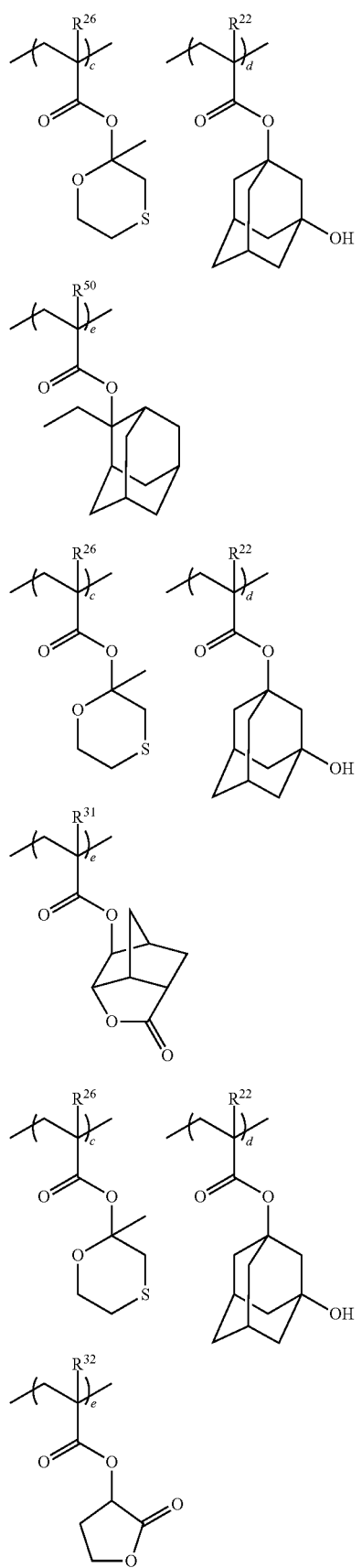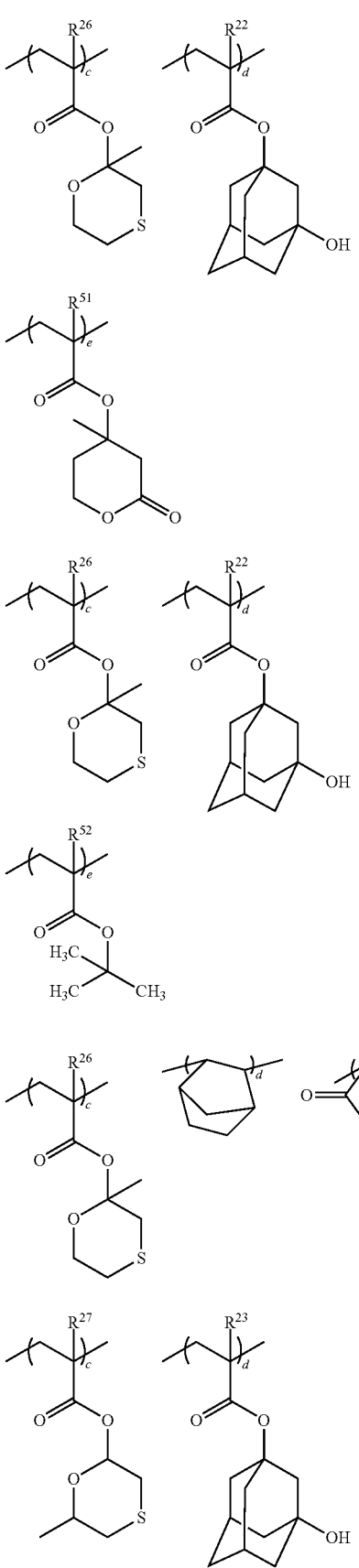

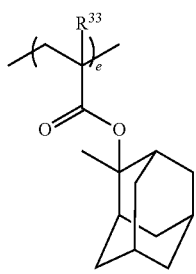
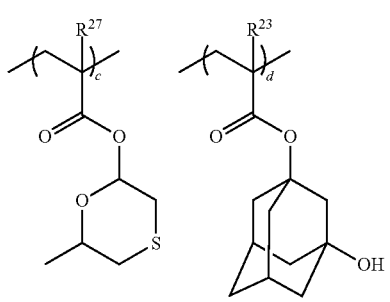
(9-30)
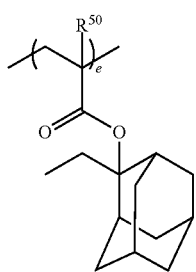
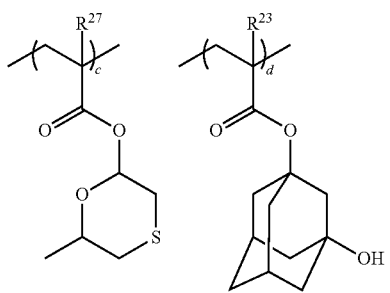
(9-31)
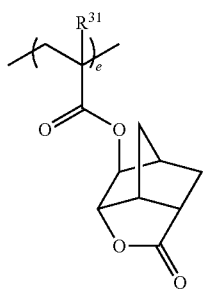
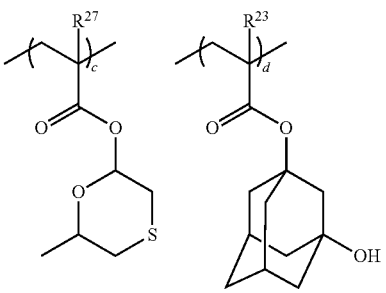
(9-32)
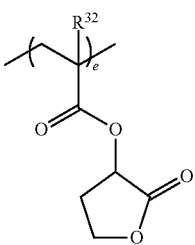
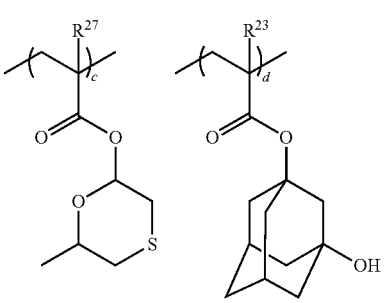
(9-33)
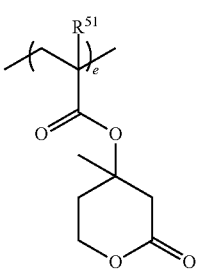
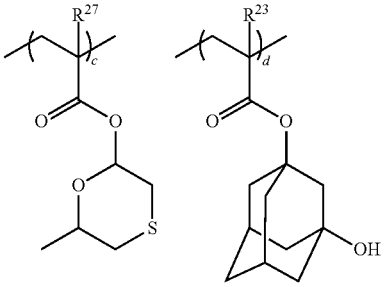
(9-34)
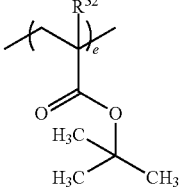

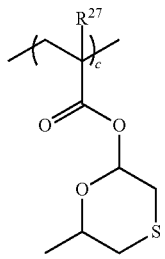
(9-35)
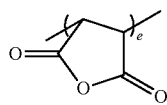
(9-36)
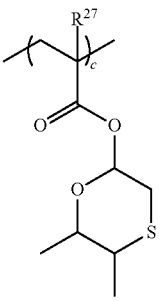 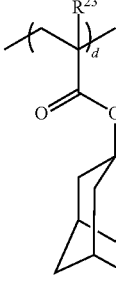
(9-38)
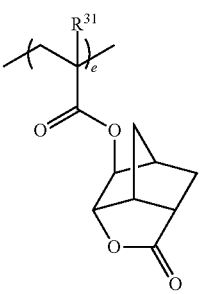
(9-39)
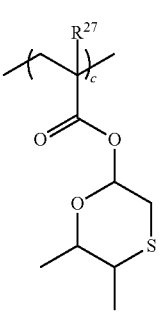 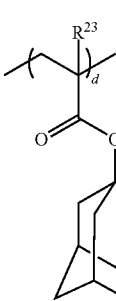
(9-37)
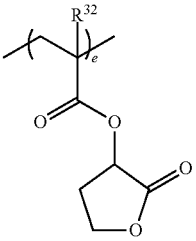
(9-40)
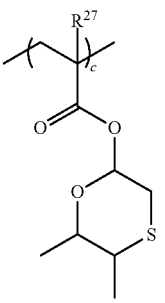 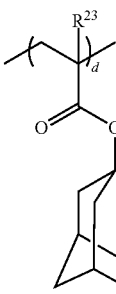

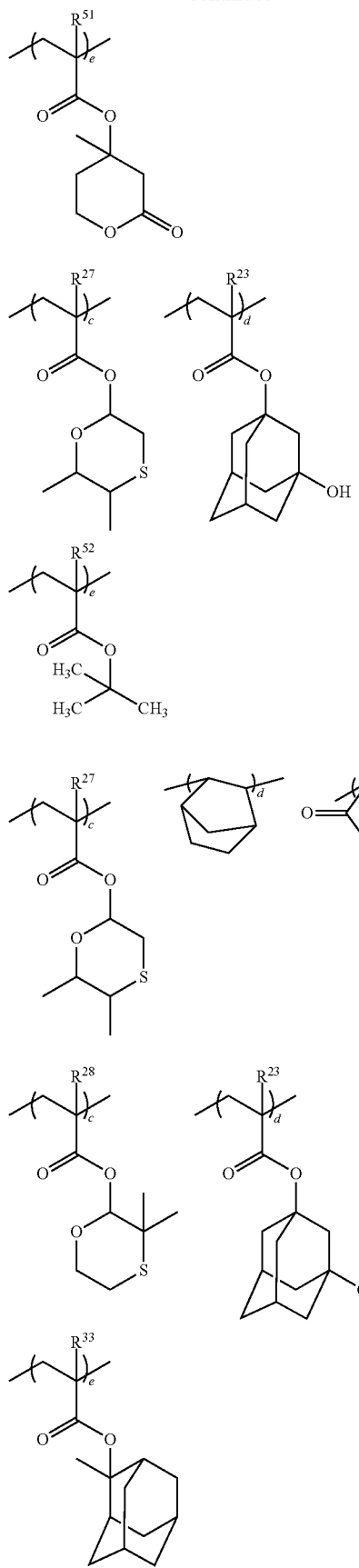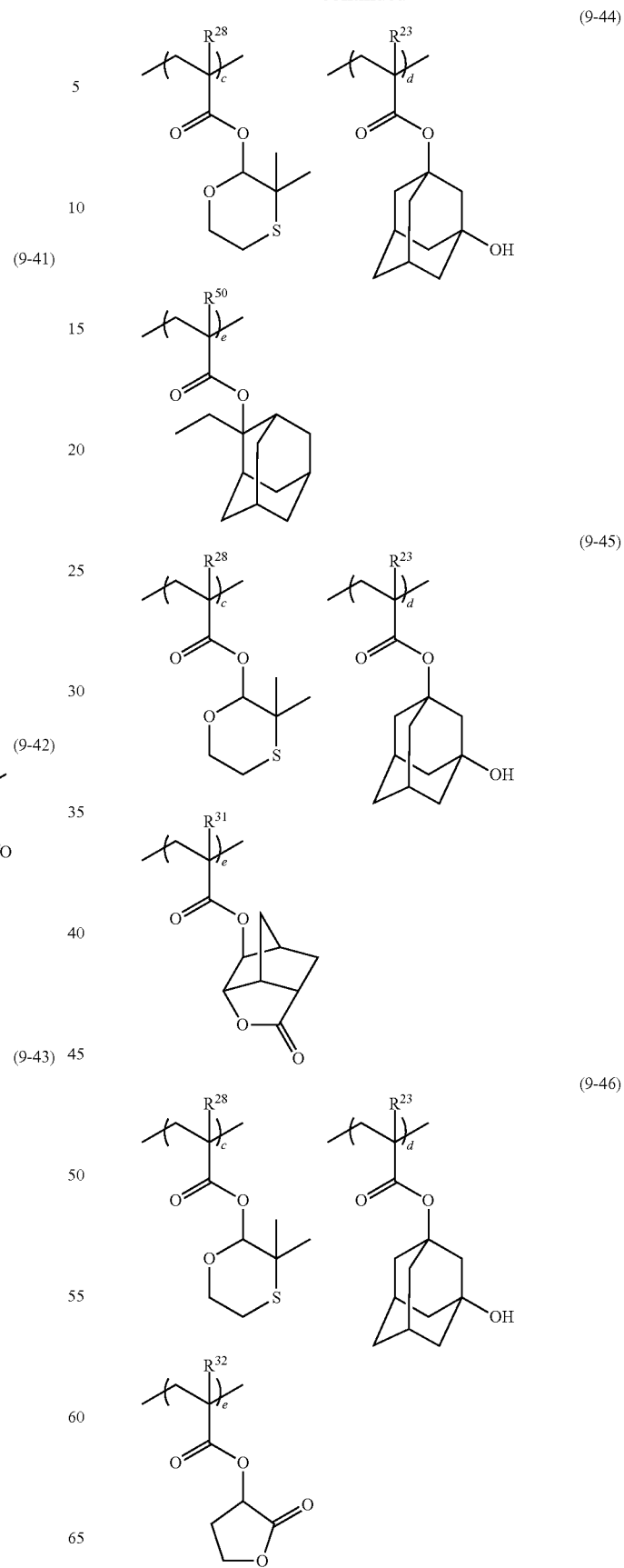

-continued
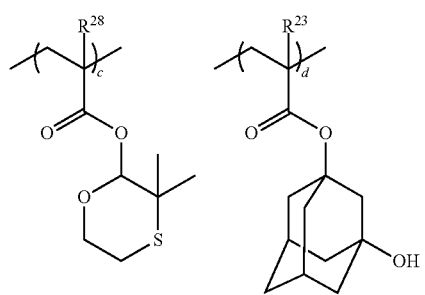
(9-47)
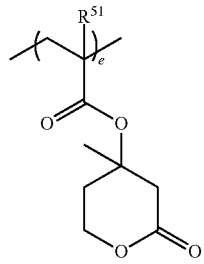
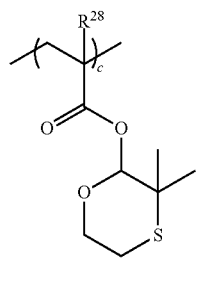
(9-48)
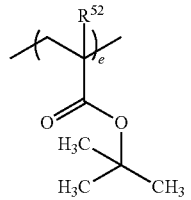
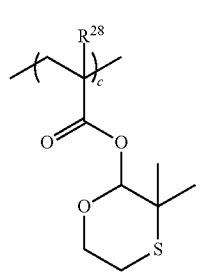
(9-49)
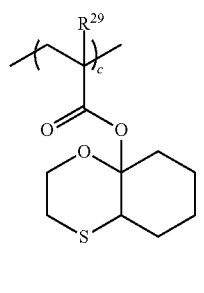
(9-50)
-continued
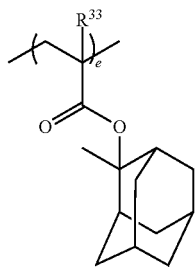
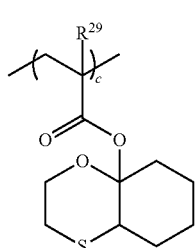
(9-51)
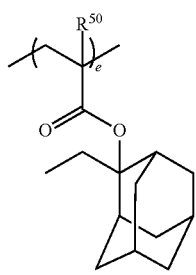
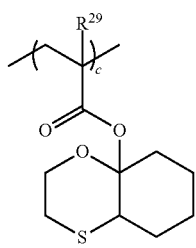
(9-52)
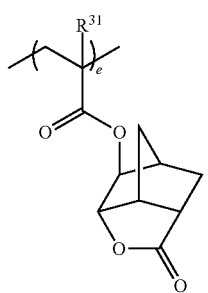

(9-53)
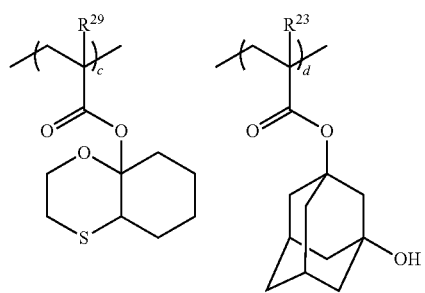
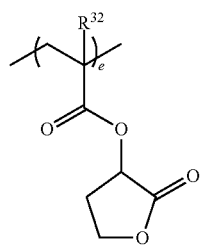
(9-54)
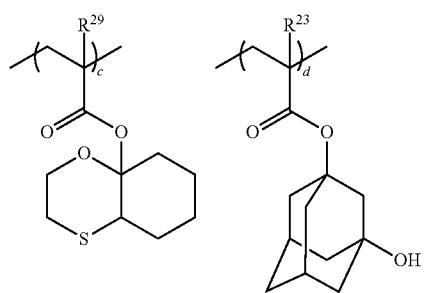
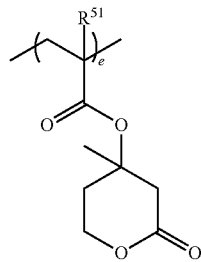
(9-55)
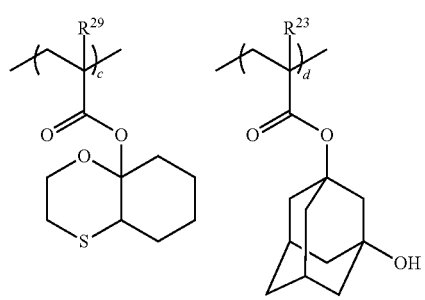
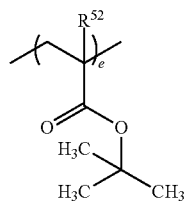
(9-56)
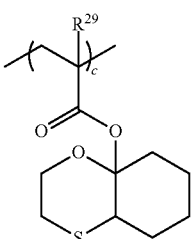 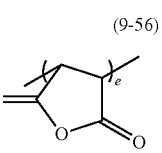 
(9-57)
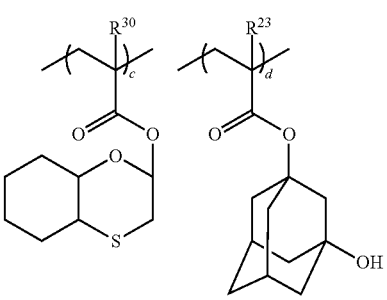
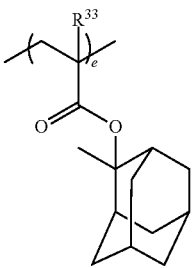
(9-58)
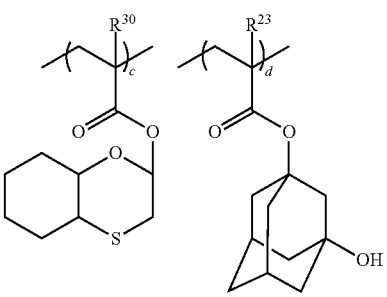
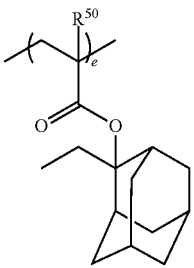

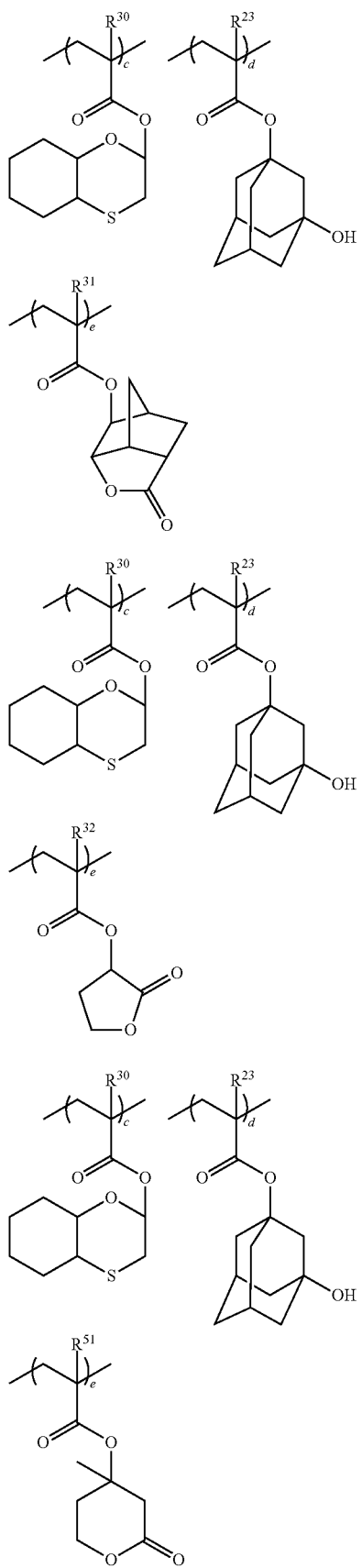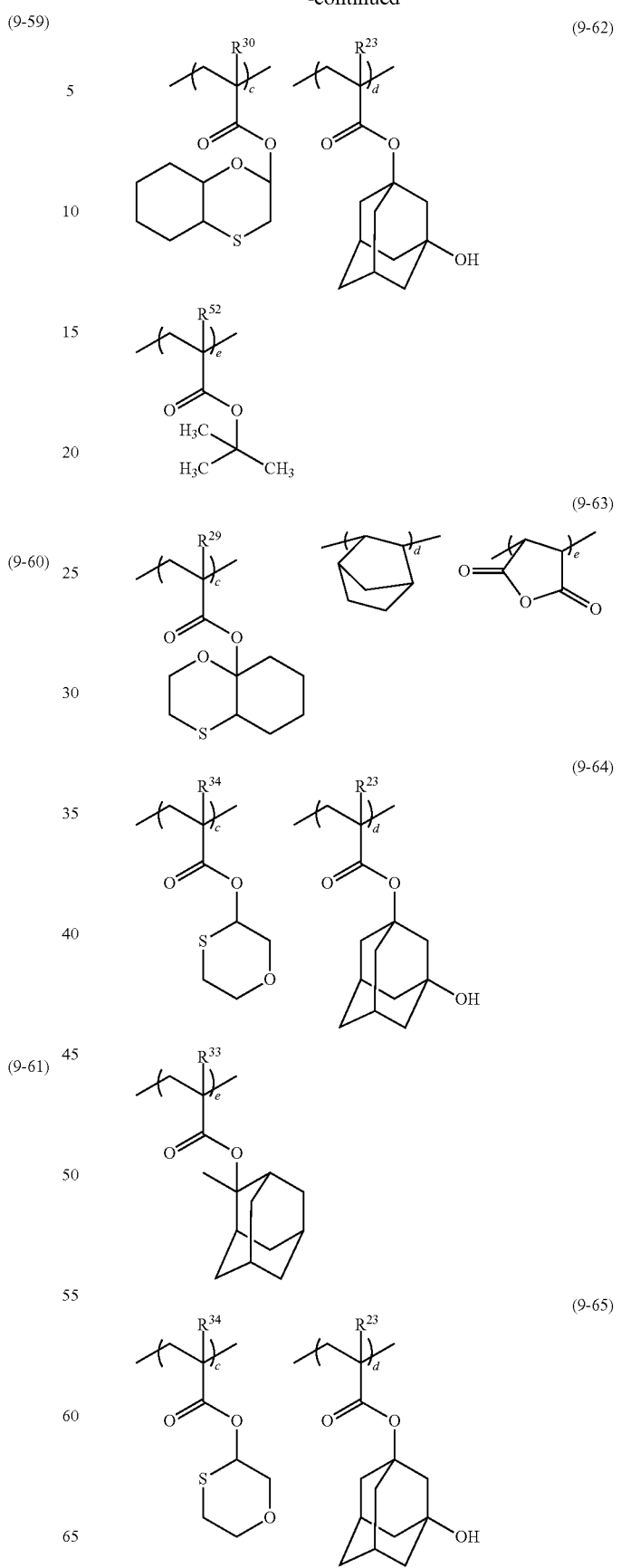

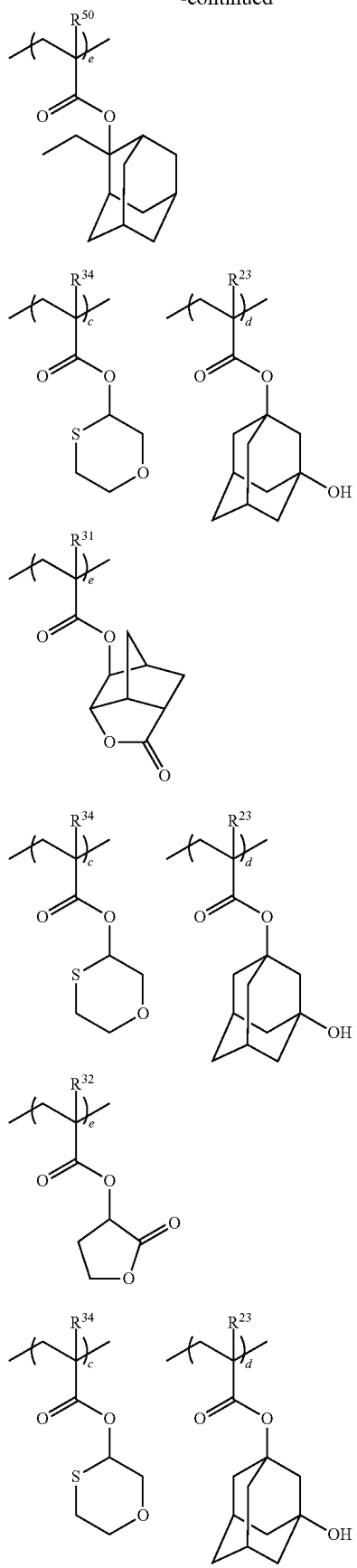
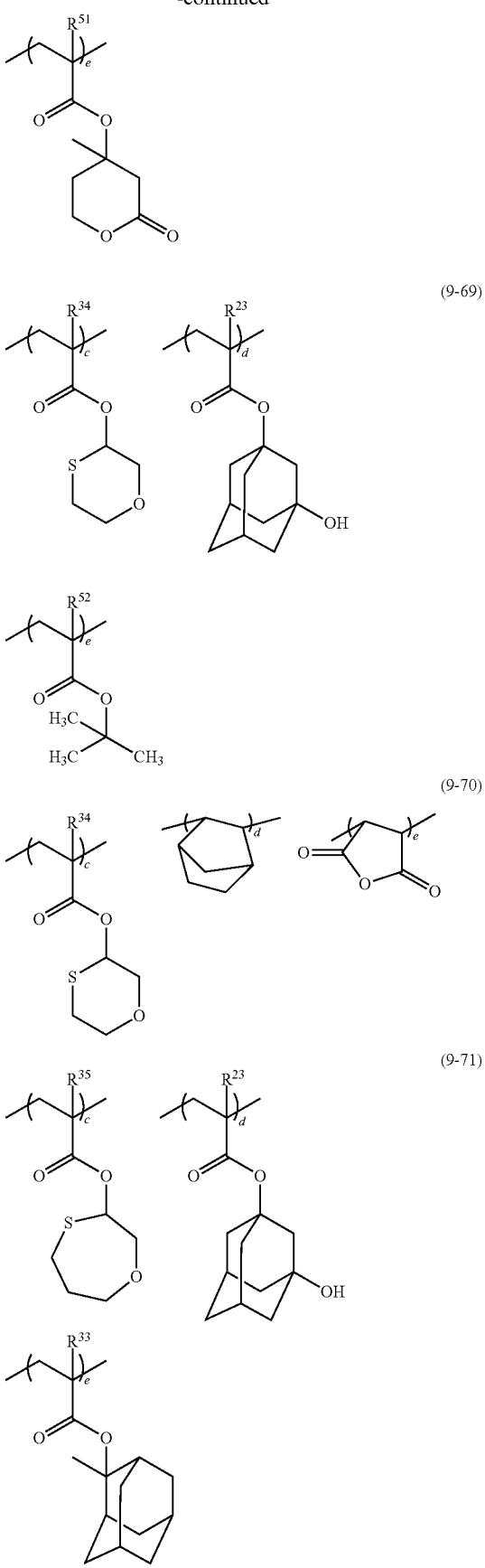

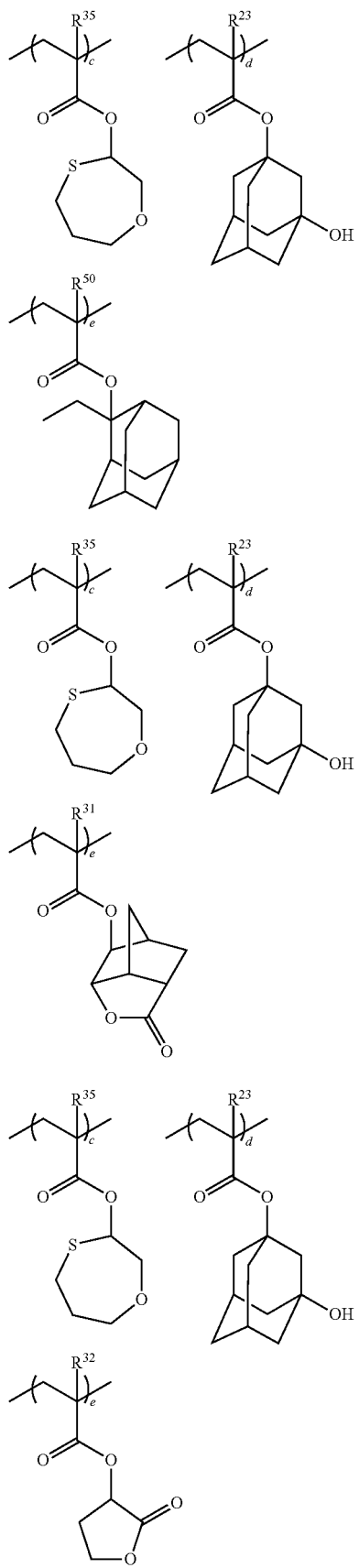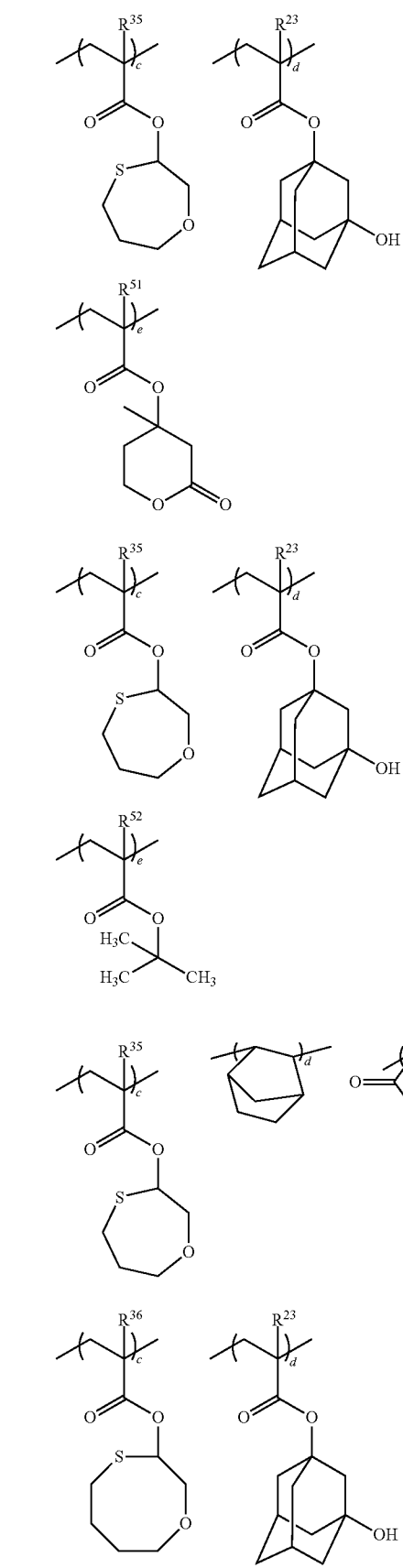

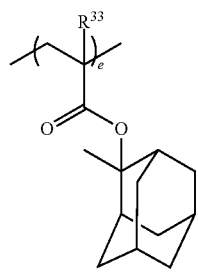
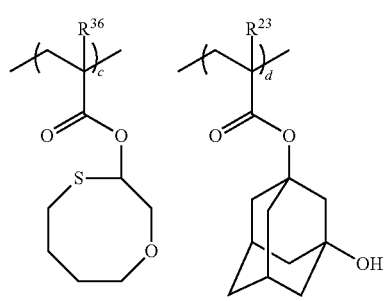
(9-79)
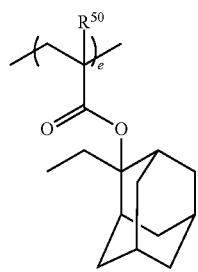
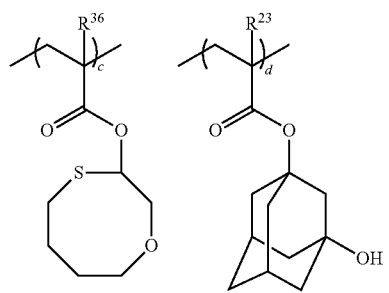
(9-80)
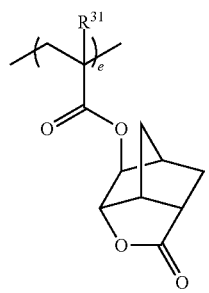
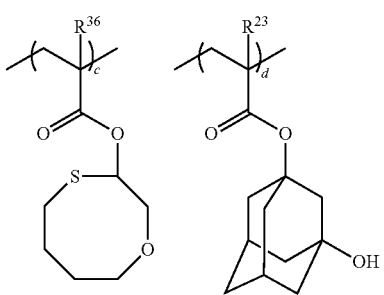
(9-81)
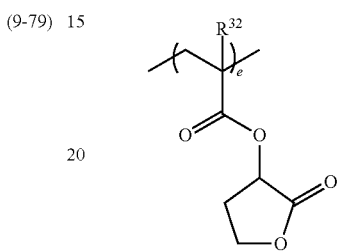
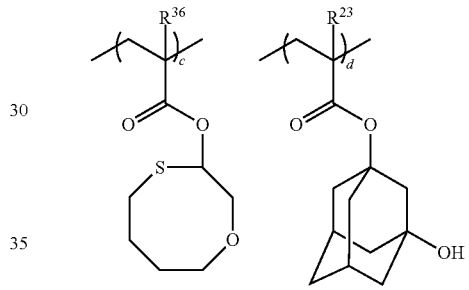
(9-82)
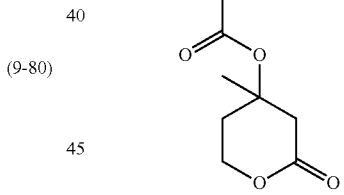
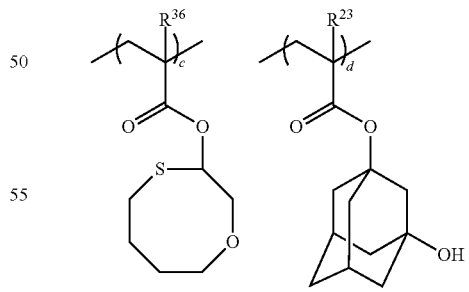
(9-83)
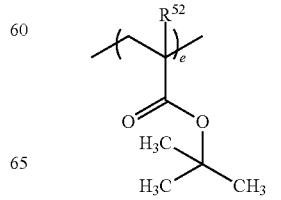

(9-84)
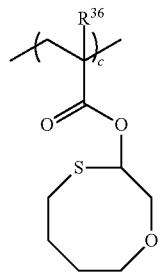  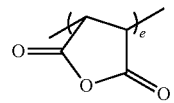
(9-85)
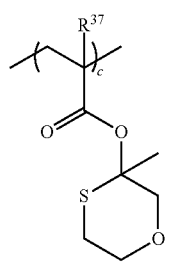 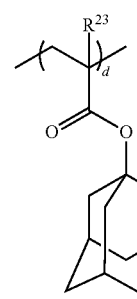
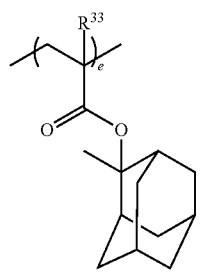
(9-86)
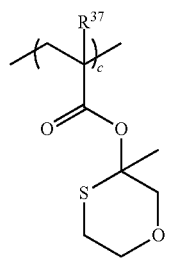 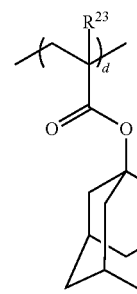
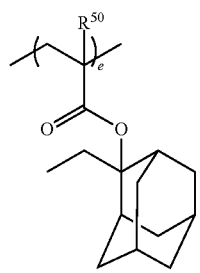
(9-87)
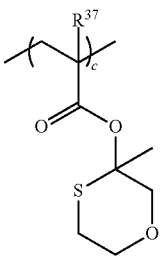 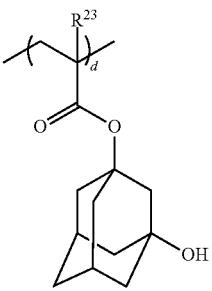
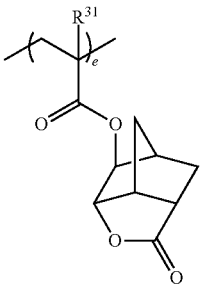
(9-88)
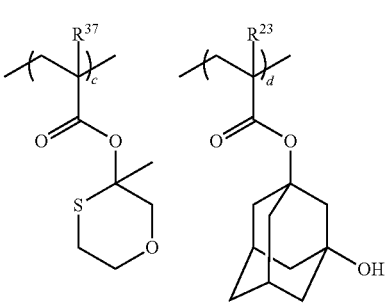
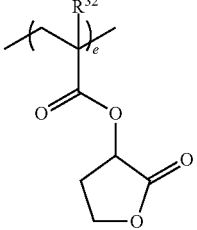
(9-89)
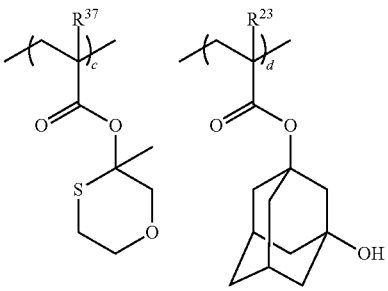
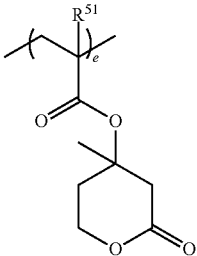

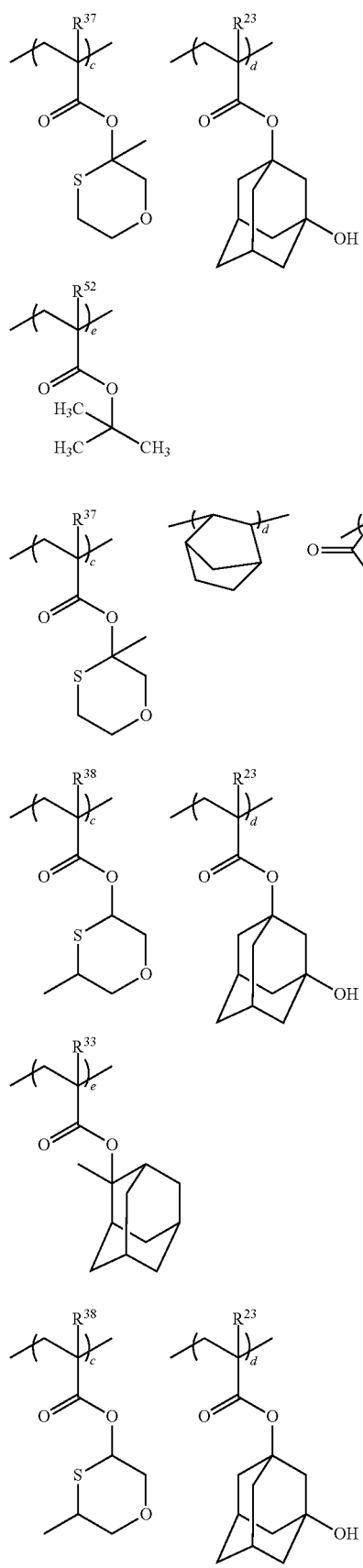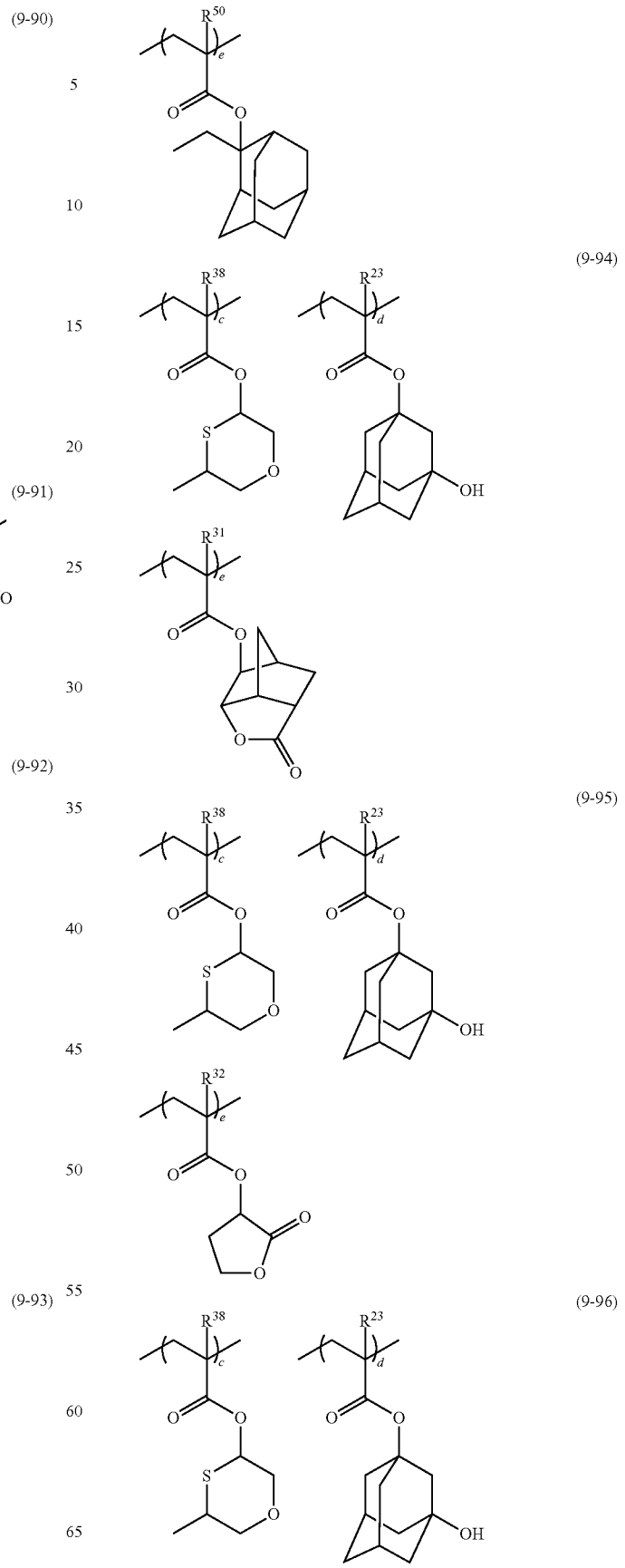

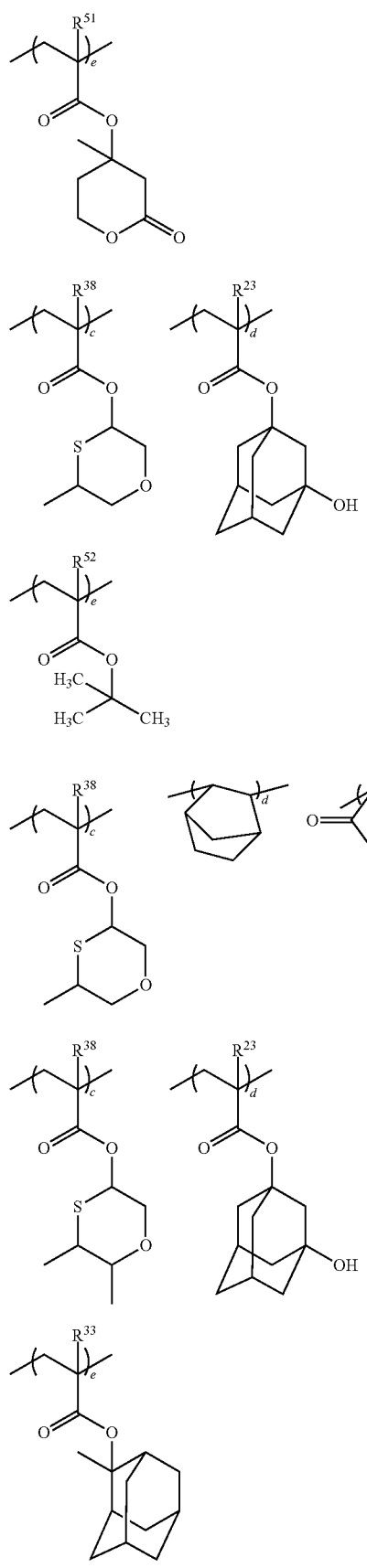
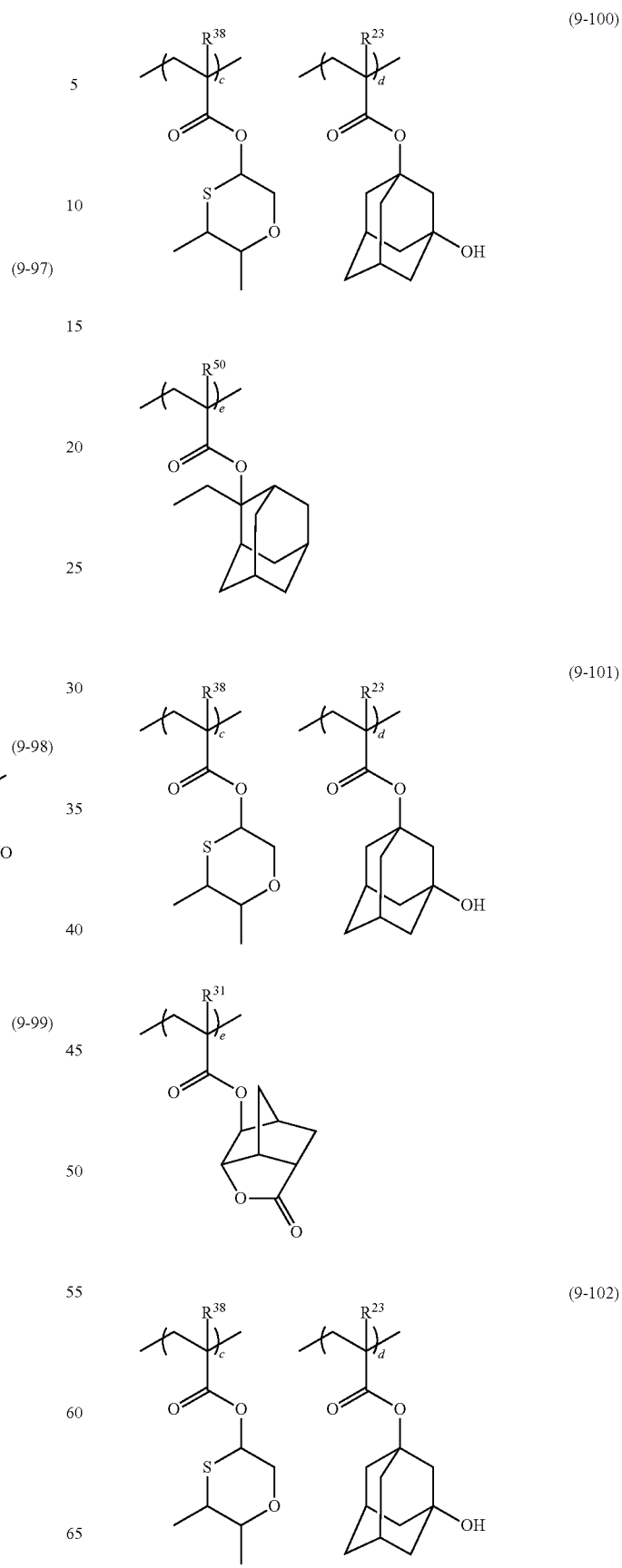

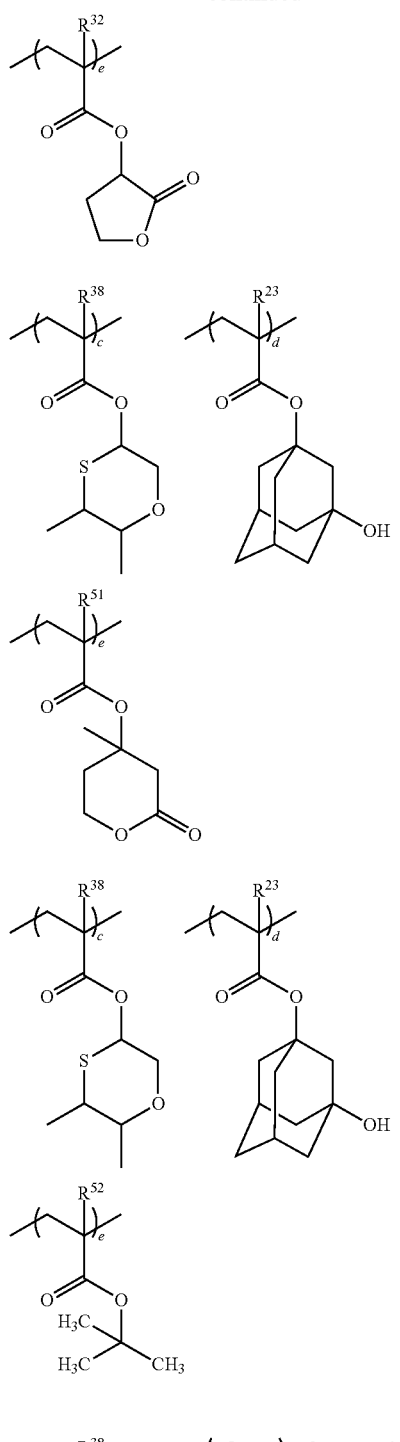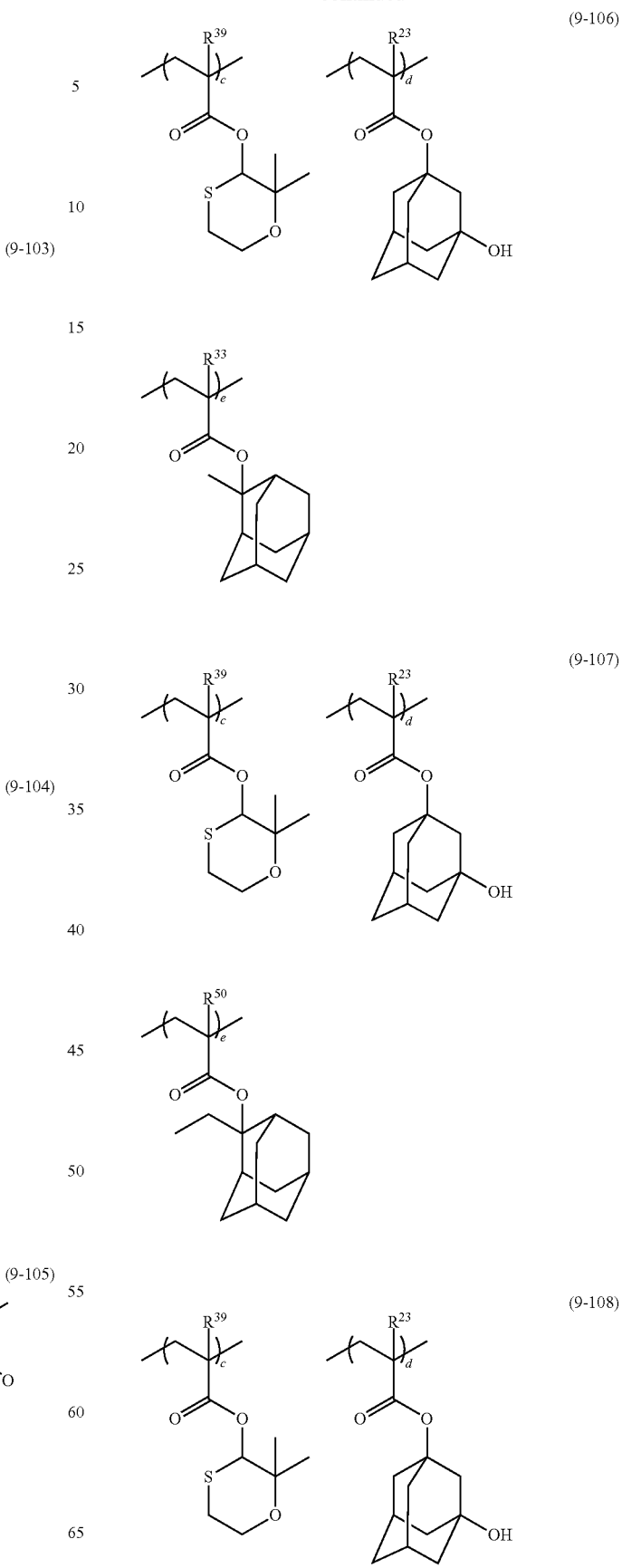

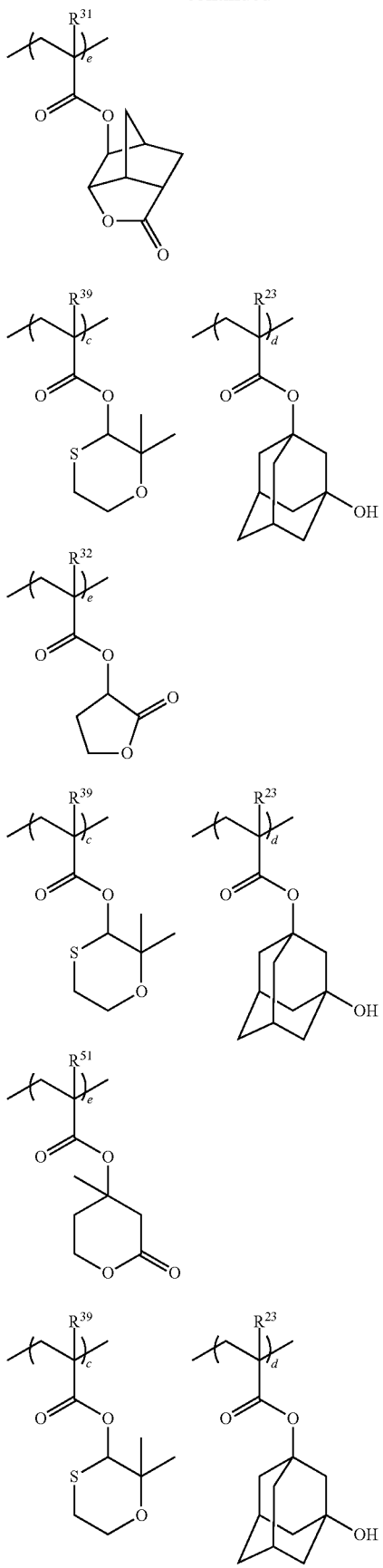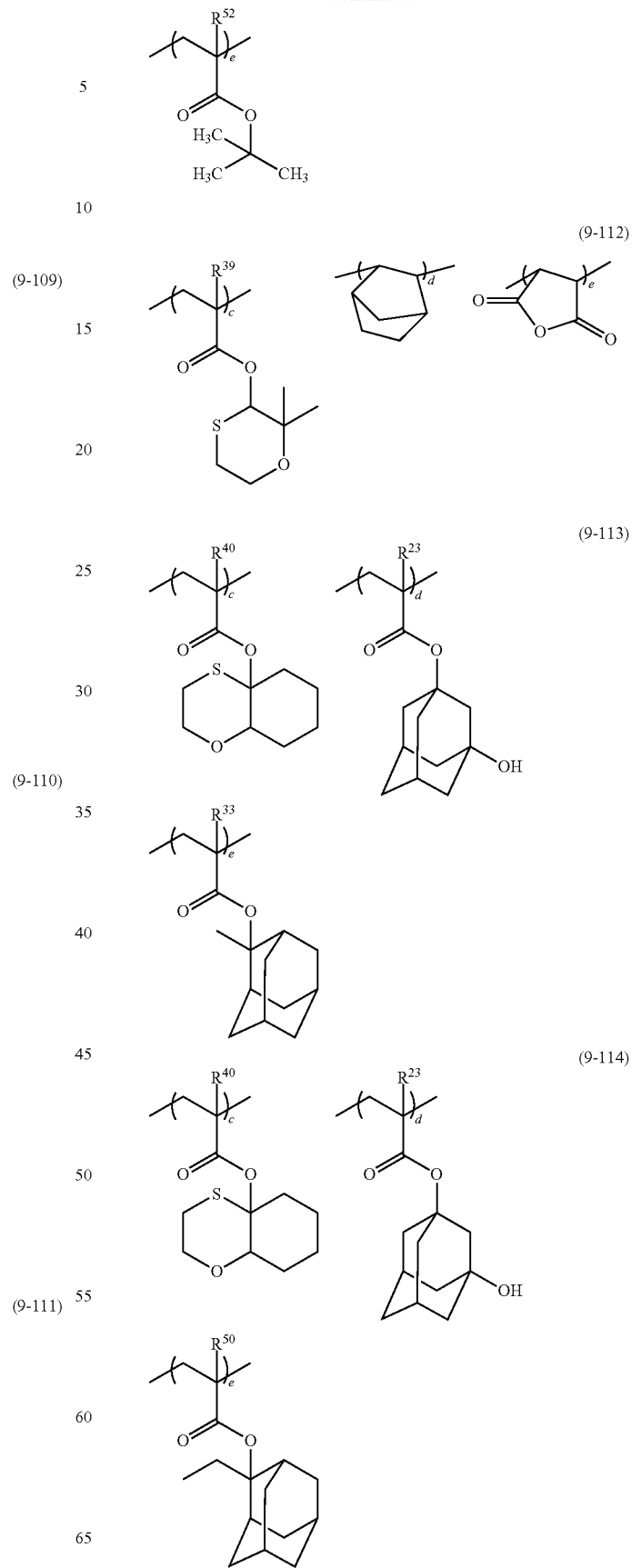

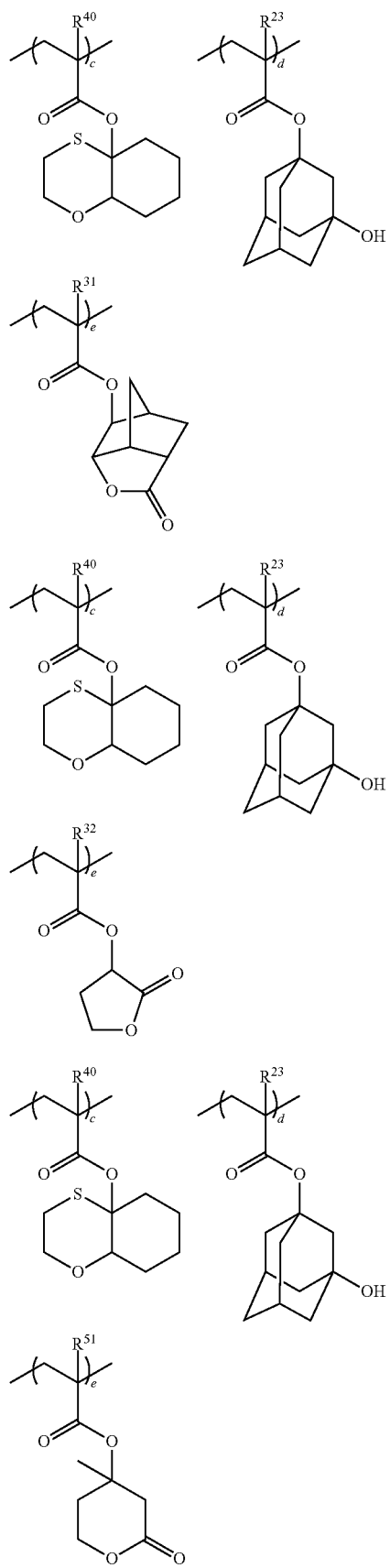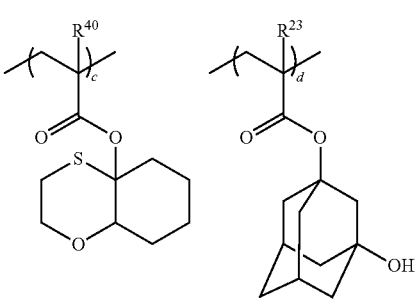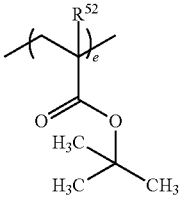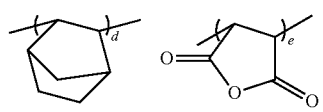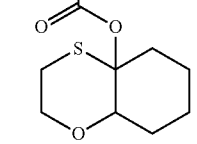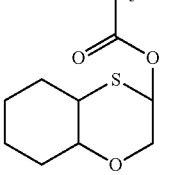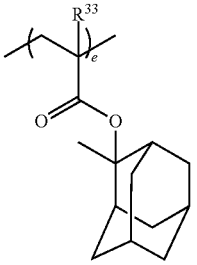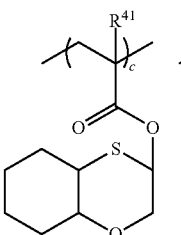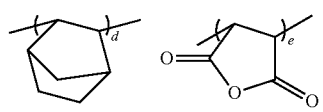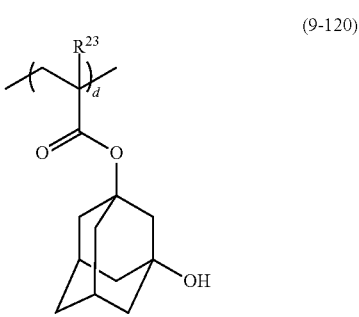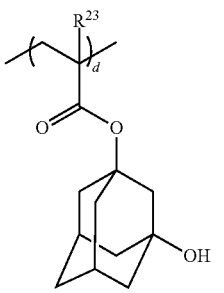

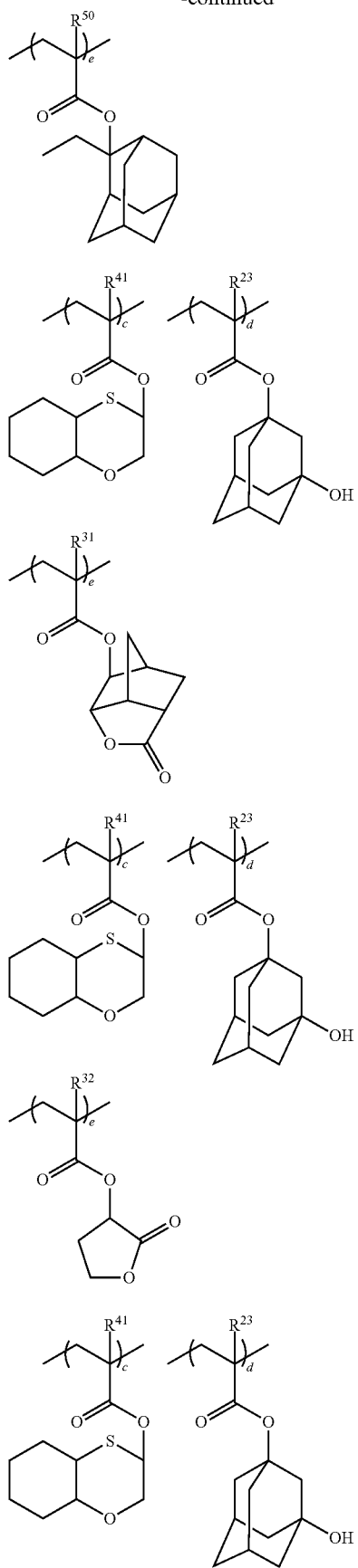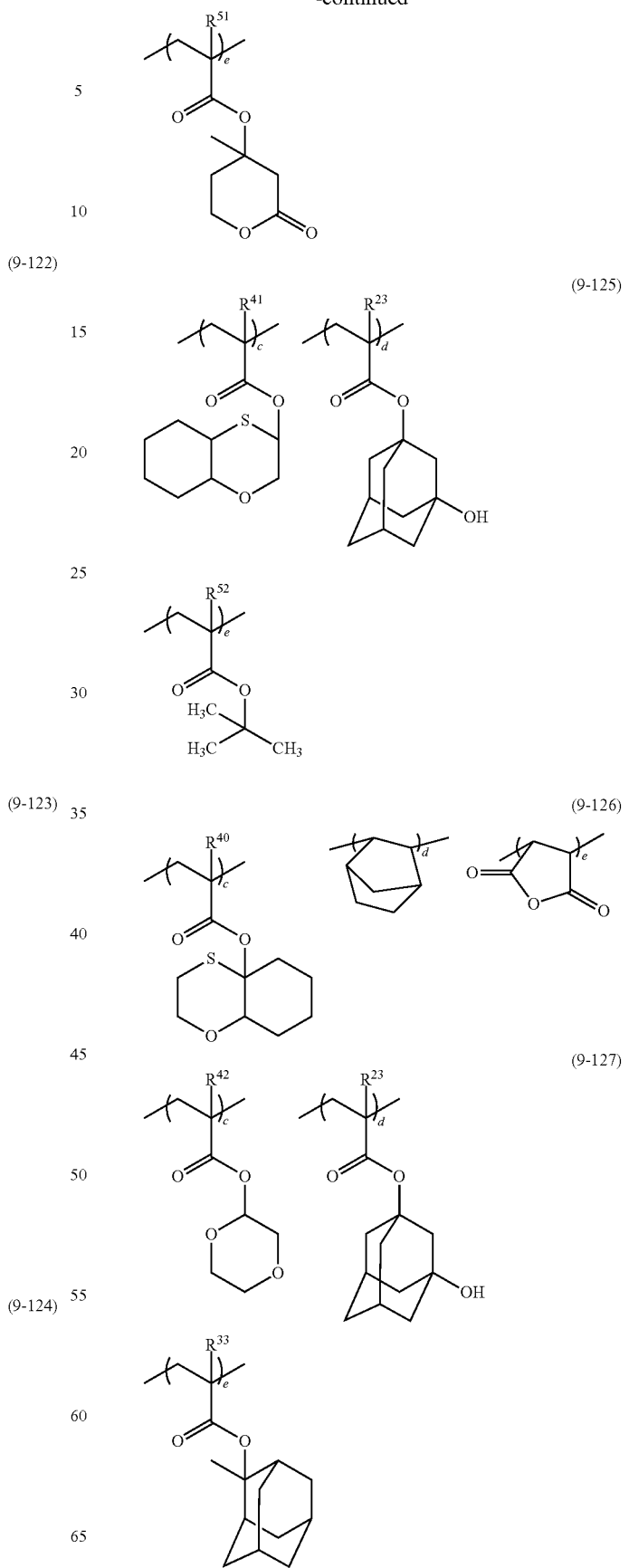

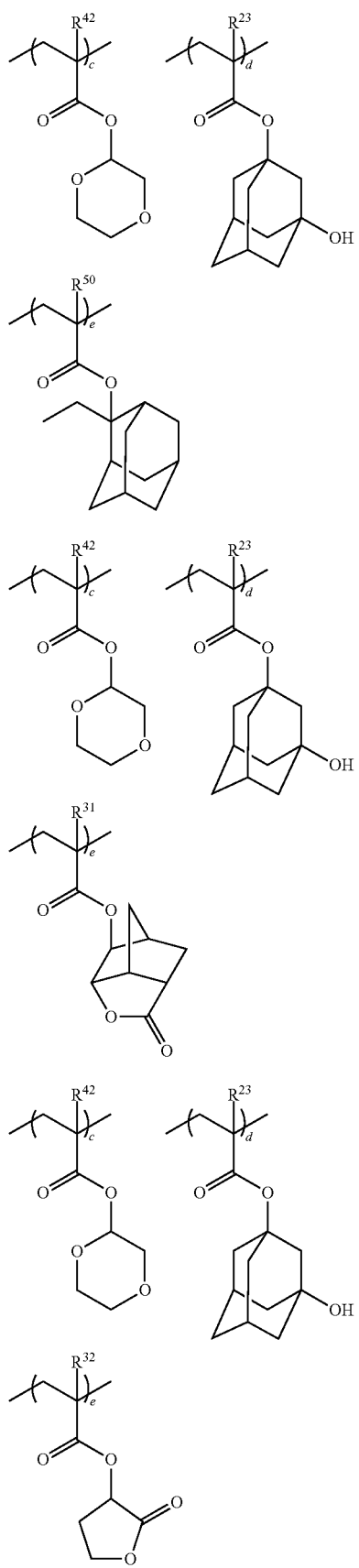
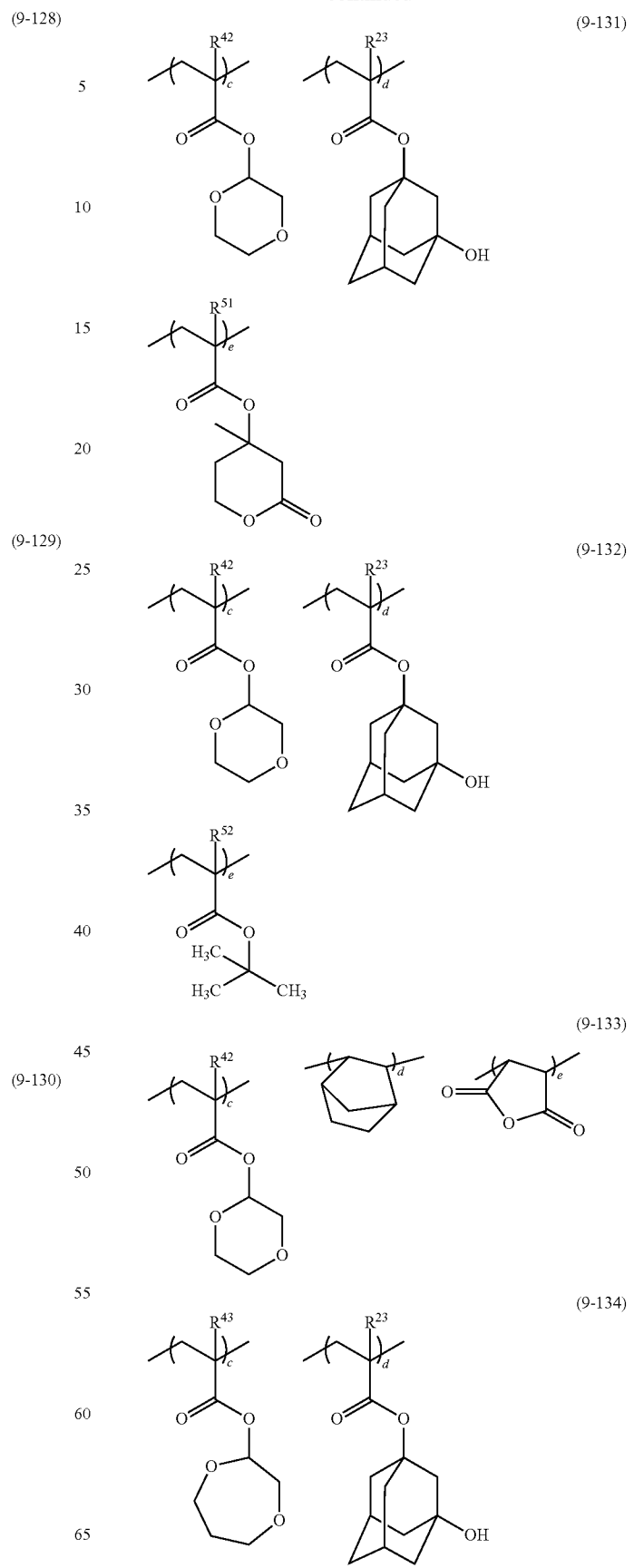

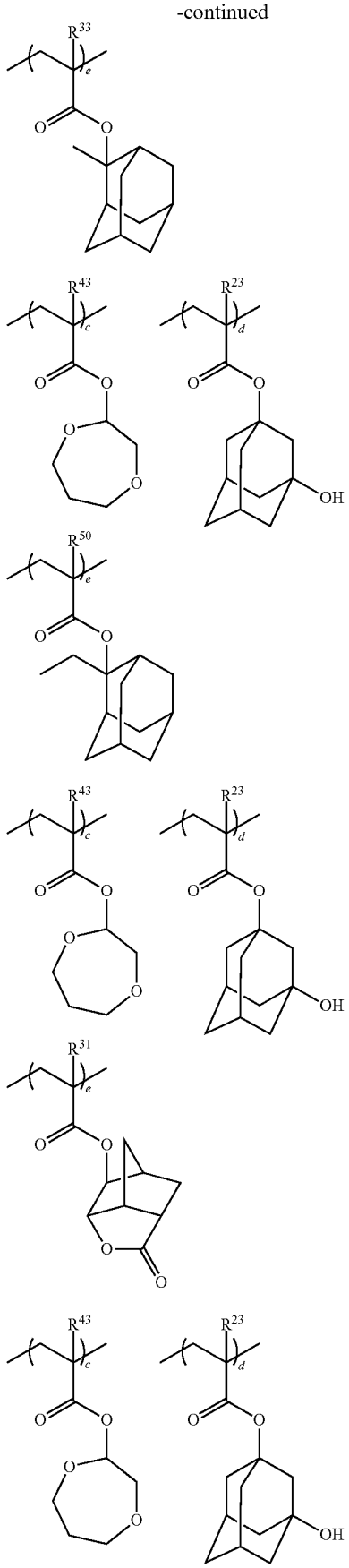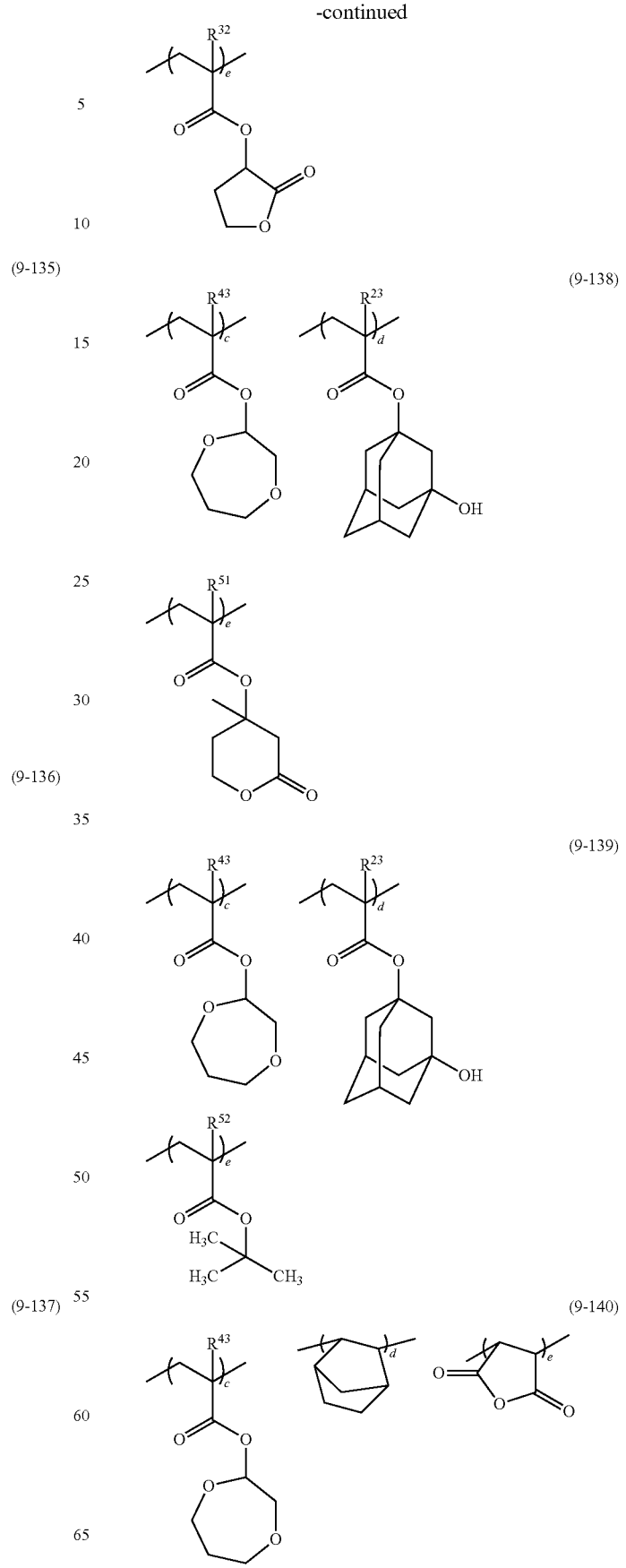

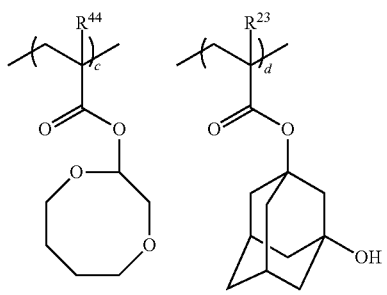
(9-141)
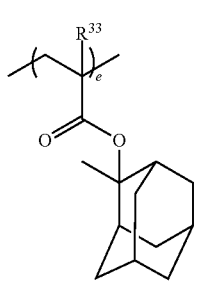
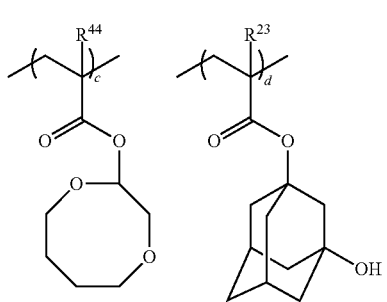
(9-142)
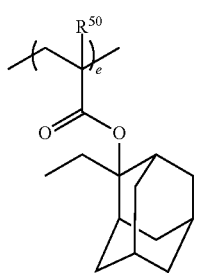
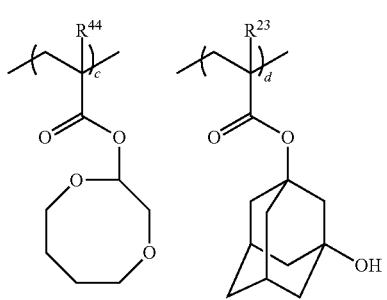
(9-143)
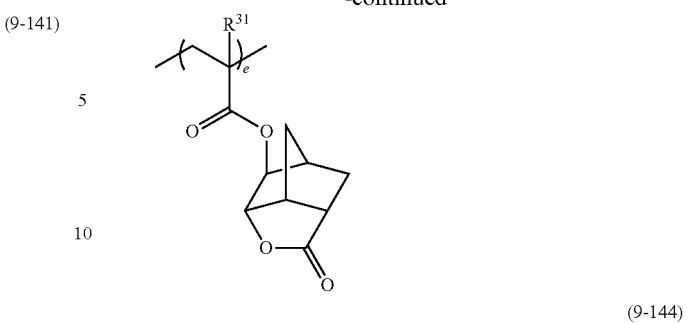
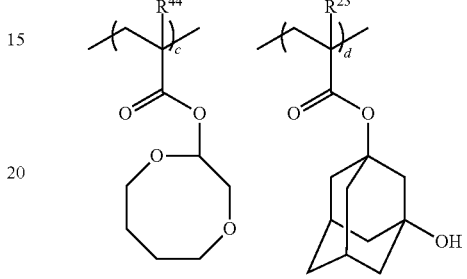
(9-144)
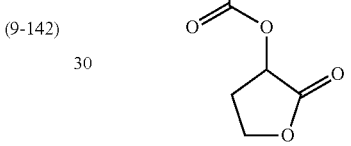
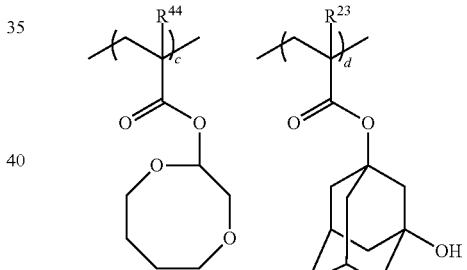
(9-145)
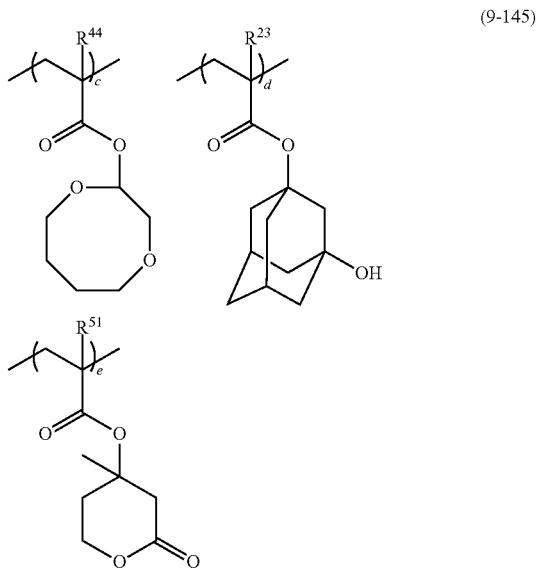
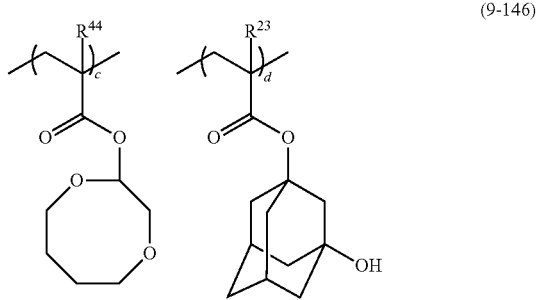
(9-146)

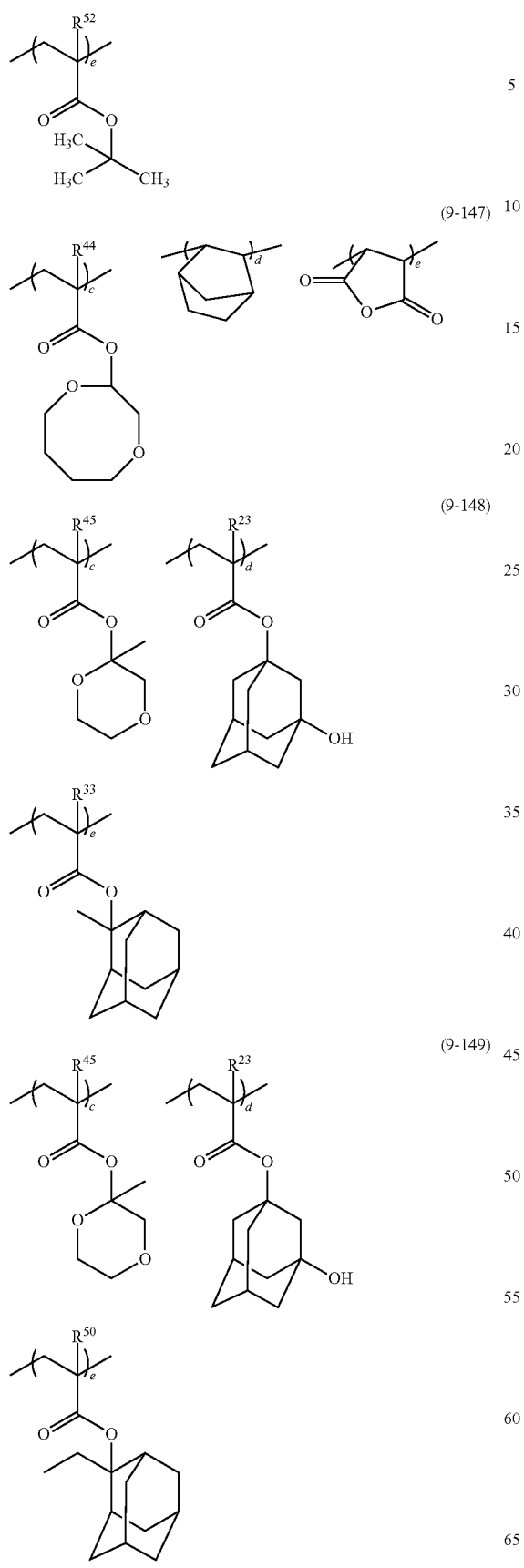
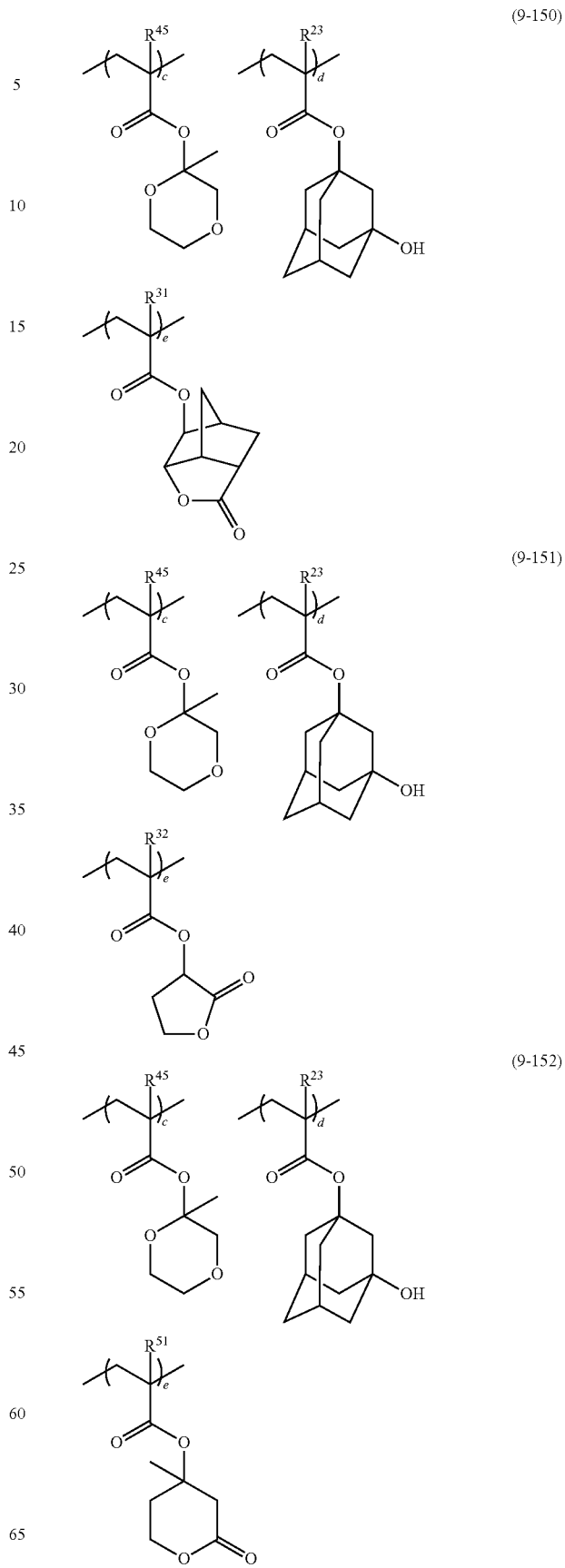

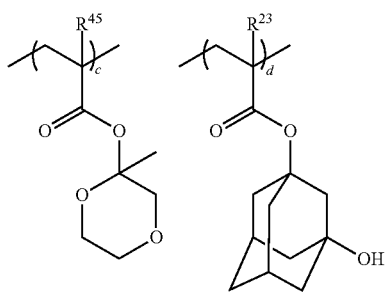
(9-153)
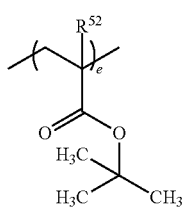
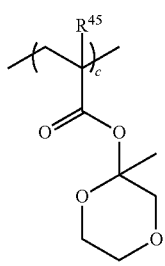
(9-154)
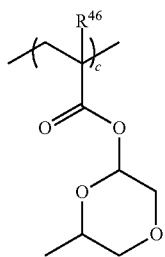
(9-155)
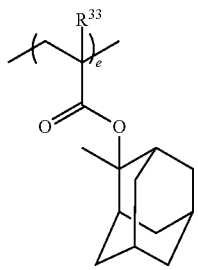
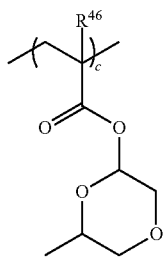
(9-156)
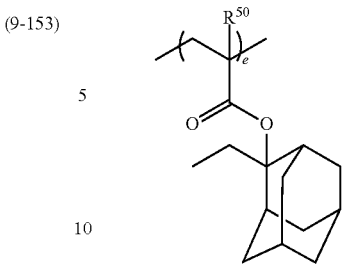
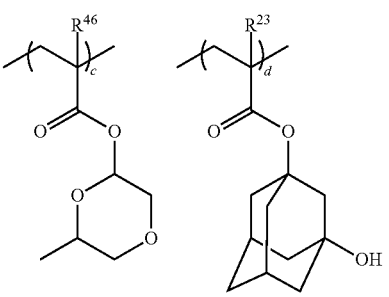
(9-157)
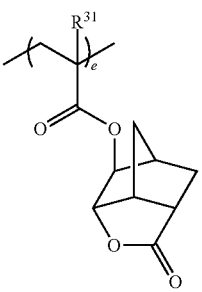
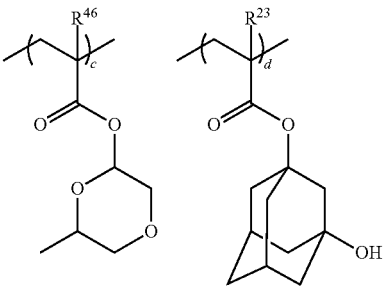
(9-158)
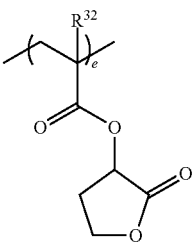
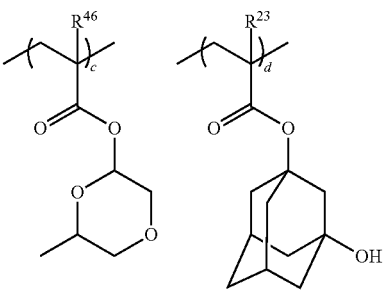
(9-159)

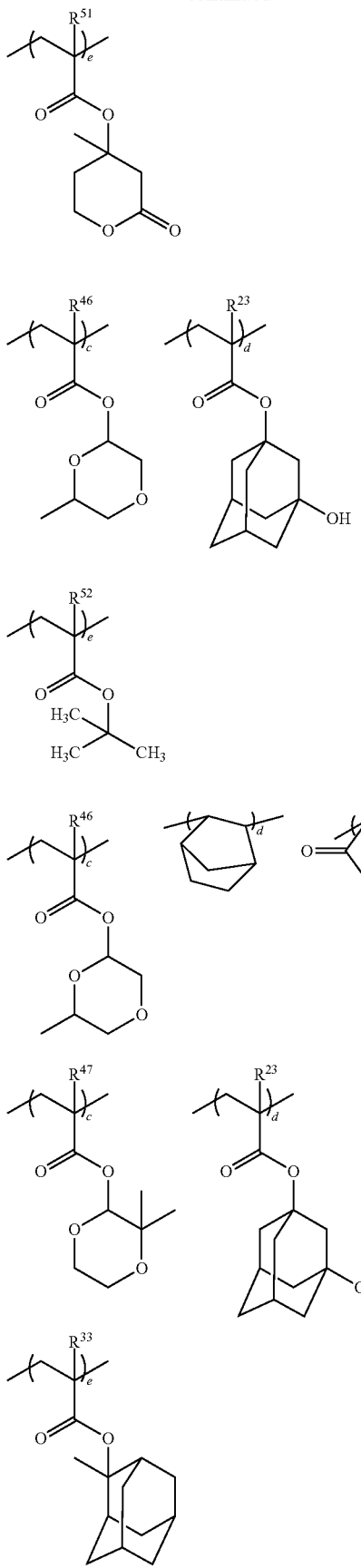

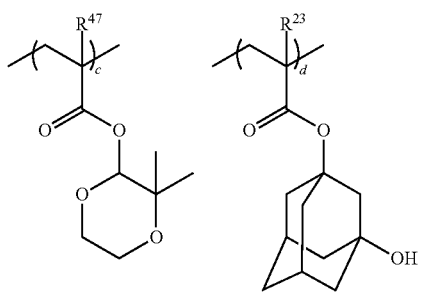
(9-166)
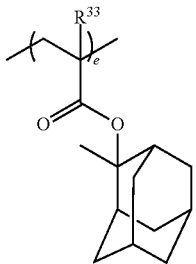
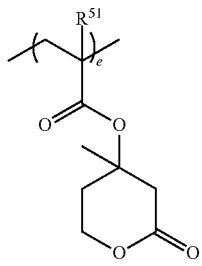
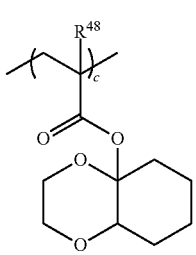
(9-170)
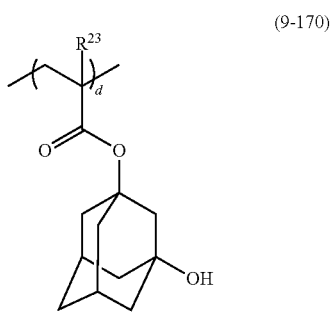
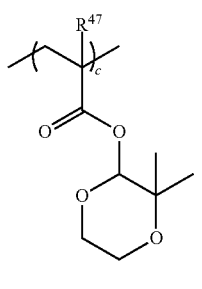
(9-167)
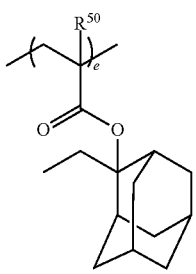
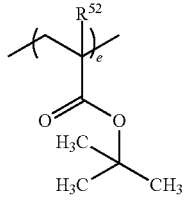
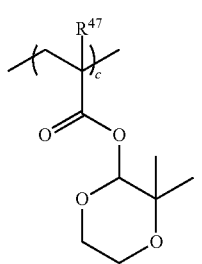
(9-168)
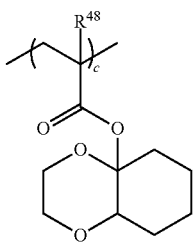
(9-171)
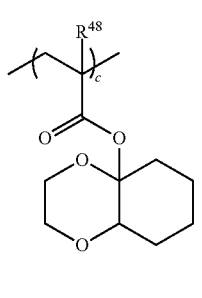
(9-169)
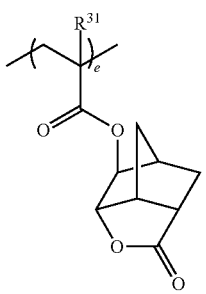

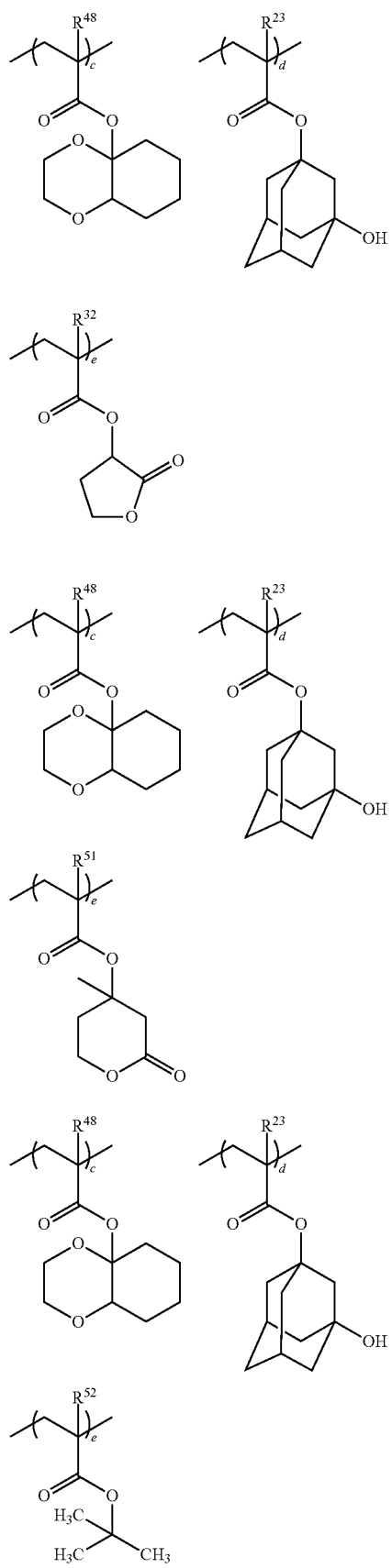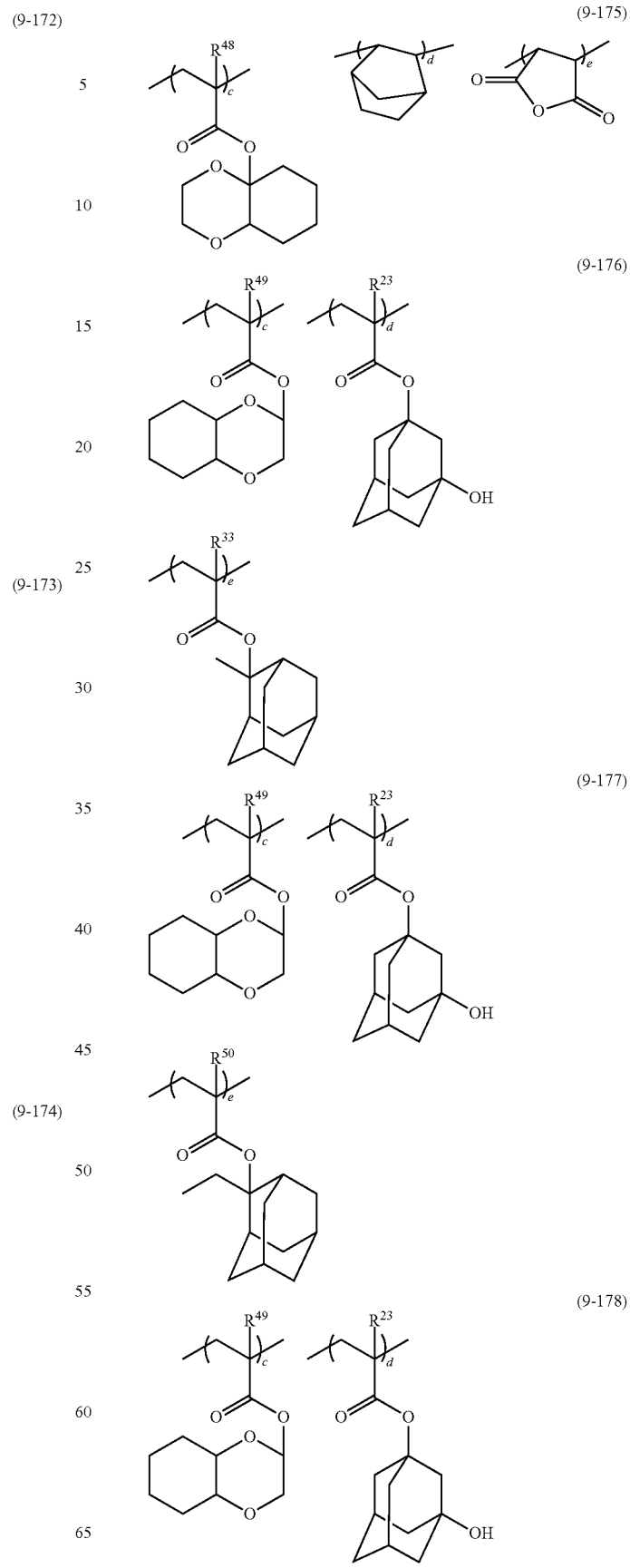

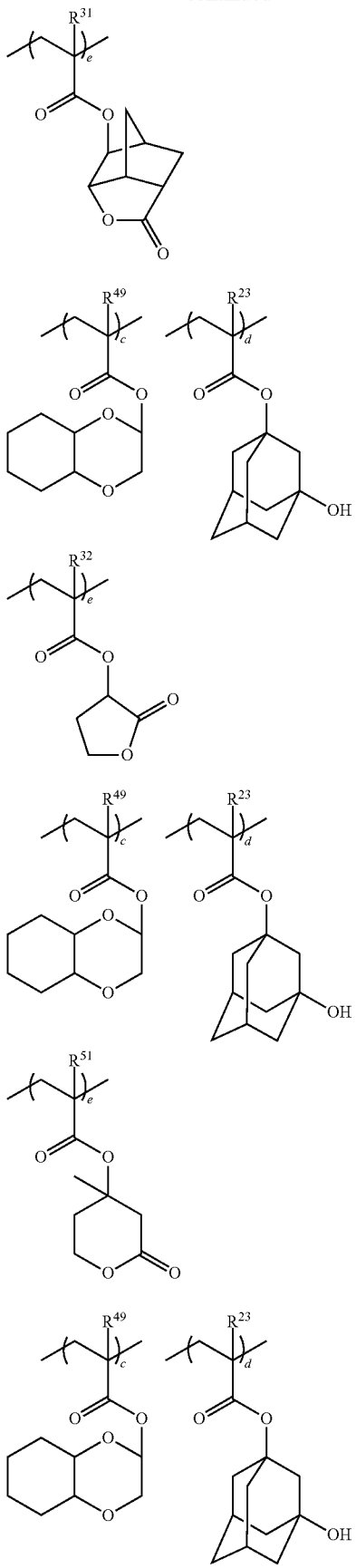

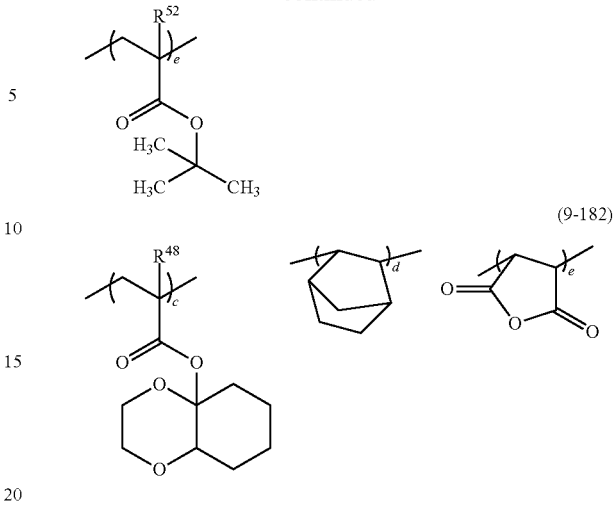

A weight average molecular weight (Mw) of the polymer (VIII) shall not specifically be restricted, and if it falls in a range of preferably 500 to 50000, more preferably 1000 to 30000, a usefulness thereof as a component for a photoresist composition described later is high. Above Mw is measured in the manner described in the example.

Photoresist Composition:

A photoresist composition can be prepared by blending the polymer (VIII) with a solvent, a photoacid generator and, if necessary, a basic compound, a surfactant and other additives each described later.

The photoresist composition blended with the polymer (VIII) shall be explained below.

Solvent:

The solvent blended with the photoresist composition includes, for example, glycol ethers such as propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether and the like; esters such as ethyl lactate, methyl 3-methoxypropionate, methyl acetate, ethyl acetate, propyl acetate and the like; ketones such as acetone, methyl ethyl ketone, methyl isopropyl ketone, methyl isobutyl ketone, methyl amyl ketone, cyclopentanone, cyclohexanone and the like; and ethers such as diethyl ether, diisopropyl ether, dibutyl ether, tetrahydrofuran, 1,4-dioxane and the like. They may be used alone or in a mixture of two or more kinds thereof.

A blending amount of the solvent falls in a range of usually 1 to 50 parts by mass, preferably 2 to 25 parts by mass based on 1 part by mass of the polymer (VIII).

Photoacid Generator:

The photoacid generator shall not specifically be restricted, and photoacid generators which have so far usually been used for chemically amplified photoresists can be used. The above photoacid generator includes, for example, nitrobenzyl derivatives such as 2-nitrobenzyl p-toluenesulfonate, 2,6-dinitrobenzyl p-toluenesulfonate, 2,4-dinitrobenzyl p-toluenesulfonate and the like; sulfonic esters such as 1,2,3-tris(methanesulfonyloxy)benzene, 1,2,3-tris(trifluoromethanesulfonyloxy)benzene, 1,2,3-tris(p-toluenesulfonyloxy)benzene and the like; diazomethane derivatives such as bis(benzenesulfonyl)diazomethane, bis(p-toluenesulfonyl)diazomethane, bis(2,4-dimethylphenylsulfonyl)diazomethane, bis(1,1-dimethylethylsulfonyl)diazomethane, bis(cyclohexylsulfonyl)diazomethane, bis(n-butylsulfonyl)diazomethane and the like; onium salts such as triphenylsulfonium nonafluoro-n-butanesulfonate, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, 1,2'-naphthylcarbonylmethyltetrahydrothiophenium triflate and the like; glyoxime derivatives such as bis-O-(p-toluenesulfonyl)-α-dimethyl glyoxime, bis-O-(n-butanesulfonyl)-α-dimethyl glyoxime and the like; sulfonic ester derivatives of N-hydroxyimide compounds such as N-hydroxysuccinimidemethanesulfonic esters, N-hydroxysuccinimidetrifluoromethanesulfonic esters, N-hydroxysuccinimide-1-propanesulfonic esters, N-hydroxyimide-p-toluenesulfonic esters, N-hydroxynaphthalimidemethanesulfonic esters, N-hydroxynaphthalimidebenzenesulfonic esters and the like; and halogen-containing triazines such as 2-(4-methoxyphenyl)-4,6-bis(trichloromethyl)-1,3,5-triazine, 2-(4-methoxynaphthyl)-4,6-bis(trichloromethyl)-1,3,5-triazine, 2-[2-(2-furyl)ethenyl]-4,6-bis(trichloromethyl)-1,3,5-triazine, 2-[2-(5-methyl-2-furyl)ethenyl]-4,6-bis(trichloromethyl)-1,3,5-triazine, 2-[2-(3,5-dimethoxyphenyl)ethenyl]-4,6-bis(trichloromethyl)-1,3,5-triazine and the like. They may be used alone or in a mixture of two or more kinds thereof.

A blending amount of the photoacid generator falls usually in a range of preferably 0.1 to 30 parts by mass, more preferably 0.5 to 10 parts by mass based on 100 parts by mass of the polymer (VIII) described above from the viewpoint of securing a sensitivity and a development of the photoresist composition.

The photoresist composition can be blended, if necessary, with a basic compound in an amount of a range in which the characteristics of the photoresist composition of the present invention are not inhibited in order to inhibit a diffusion rate of acid in the photoresist film to enhance a resolution thereof. The above basic compound includes, for example, amides such as formamide, N-methylformamide, N,N-dimethylformamide, acetamide, N-methylacetamide, N,N-dimethylacetamide, N-(1-adamantyl)acetamide, benzamide, N-acetylethanolamine, 1-acetyl-3-methylpiperidine, pyrrolidone, N-methylpyrrolidone, ε-caprolactam, δ-valerolactam, 2-pyrrolidinone, acrylamide, methacrylamide, t-butylacrylamide, methylenebisacrylamide, methylenebismethacrylamide, N-methylolacrylamide, N-methoxyacrylamide, diacetoneacrylamide and the like; and amines such as pyridine, 2-methylpyridine, 4-methylpyridine, nicotine, quinoline, acridine, imidazole, 4-methylimidazole, benzimidazole, pyrazine, pyrazole, pyrrolidine, N-t-butoxycarbonylpyrrolidine, piperidine, tetrazole, morpholine, 4-methylmorpholine, piperazine, 1,4-diazabicyclo[2.2.2]octane, tributylamine, tripentylamine, trihexylamine, triheptylamine, trioctylamine, triethanolamine and the like. They may be used alone or in a mixture of two or more kinds thereof.

When the basic compound is blended, a blending amount thereof is varied depending on the kind of the basic compound used and falls usually in a range of preferably 0.01 to 10 mole, more preferably 0.05 to 1 mole based on 1 mole of the photoacid generator.

Surfactant:

The photoresist composition can be further blended, if desired, with a surfactant in an amount of a range in which the characteristics of the photoresist composition are not inhibited in order to enhance the coating property.

The above surfactant includes, for example, polyoxyethylene lauryl ether, polyoxyethylene stearyl ether, polyoxyethylene oleyl ether, polyoxyethylene n-octylphenyl ether and the like. They may be used alone or in a mixture of two or more kinds thereof.

When the surfactant is blended, a blending amount thereof is usually 2 parts by mass or less based on 100 parts by mass of the polymer (VIII).

Other Additives:

Further, the photoresist composition can be blended with a sensitizer, a halation inhibitor, a form-improving agent, a storage stabilizer, a defoaming agent and the like as other additives in an amount of a range in which the characteristics of the photoresist composition are not inhibited.

Formation of Photoresist Pattern:

The photoresist composition is coated on a substrate and pre-baked usually at 70 to 160° C. for 1 to 10 minutes, and it is irradiated (exposed) with a radiation via a prescribed mask and then subjected to post exposure baking at 70 to 160° C. for 1 to 5 minutes to form a latent image pattern. Then, it is developed in a developer, whereby a prescribed resist pattern can be formed.

Radiations having various wavelengths, for example, a UV ray, an X ray and the like can be used for the exposure, and usually a g beam, an i beam and excimer lasers of XeCl, KrF, KrCl, ArF, ArCl and the like are used for a semiconductor resist. Among them, an ArF excimer laser is preferably used from the viewpoint of fine processing.

An exposure dose thereof falls in a range of preferably 0.1 to 1000 mJ/cm$^2$, more preferably 1 to 500 mJ/cm$^2$.

The developer includes, for example, inorganic bases such as sodium hydroxide, potassium hydroxide, sodium carbonate, aqueous ammonia and the like; alkylamines such as ethylamine, diethylamine, triethylamine and the like; alcoholamines such as dimethylethanolamine, triethanolamine and the like; and alkaline aqueous solutions prepared by dissolving quaternary ammonium salts such as tetramethylammonium hydroxide, tetraethylammonium hydroxide and the like. Among them, preferably used are the alkaline aqueous solutions prepared by dissolving quaternary ammonium salts such as tetramethylammonium hydroxide, tetraethylammonium hydroxide and the like.

A concentration of the developer falls usually in a range of preferably 0.1 to 20% by mass, more preferably 0.1 to 10% by mass.

Liquid Immersion Lithography:

The photoresist composition can be applied as well to liquid immersion lithography. The liquid immersion lithography is an exposing technique in which a liquid having a higher refractive index of light than that of the air is injected between a projector lens of an exposing equipment and a resist film to thereby enhance a resolution. In an ArF liquid immersion lithography, purified water is used as the above liquid. To be specific, when exposed with an ArF excimer laser having a wavelength of 193 nm, purified water is injected between a resist film after pre-baked and a projector lens to carry out the exposure, whereby a radiation passing through the resist film is shifted to a shorter wavelength of 135 nm, and therefore the high resolution can be obtained.

EXAMPLES

The present invention shall be explained in further details with reference to examples, but the present invention shall by no means be restricted by these examples. The respective measuring methods in the respective examples are shown below.

Measurement of Mw and Mn and Calculation of Dispersion Degree:

The weight average molecular weight (Mw) and the number average molecular weight (Mn) were measured on the following conditions by gel permeation chromatography (GPC) using tetrahydrofuran (THF) as an eluant by means of a differential refractometer used as a detector, and they were determined as values converted according to a calibration curve prepared using standard polystyrene. Further, the dispersion degree (Mw/Mn) was determined by dividing the weight average molecular weight (Mw) by the number average molecular weight (Mn).

GPC Measurement:

Used was a column obtained by connecting serially two columns of TSK-gel SUPER HZM-H (trade name, 4.6 mm×150 mm, manufactured by Tosoh Corp.) and one column of TSK-gel SUPER HZ2000 (trade name, 4.6 mm×150 mm, manufactured by Tosoh Corp.), and measurement was carried out on the conditions of a column temperature of 40° C., a differential refractometer temperature of 40° C. and a flow velocity of 0.35 mL/minute in the eluant.

Measurement of a Log Value (Log P) of an Octanol/Water Distribution Coefficient and a Solubility Parameter (SP):

Also, log P which is a log value of an octanol/water distribution coefficient and SP which is a solubility parameter were calculated by using Hamiltonian PM5 of a calculation soft "CAChe" (trade name, manufactured by Fujitsu Limited).

Example 1

Production of 1,4-oxathiane-2-ol

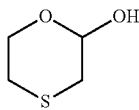

A four neck flask having a content volume of 2 L equipped with a thermometer, a reflux condenser and a stirring device was charged with 691 g of methanol. The flask was cooled on an ice bath, and 128.1 g (3.20 mol) of sodium hydroxide was added thereto little by little while stirring so that the temperature did not exceed 50° C. After finishing addition of sodium hydroxide, stirring was continued, and when the temperature was 2 to 5° C., 250.3 g (3.20 mol) of mercaptoethanol was slowly added thereto from a dropping funnel so that the temperature was controlled in a range of 5 to 10° C. After finishing dropwise adding, stirring was continued for one hour, and 295.6 g (2.37 mol) of chloroacetaldehyde=dimethyl=acetal was dropwise added from a dropping funnel so that the temperature was controlled in a range of 5 to 10° C. After finishing dropwise adding, heating was started, and the solution was stirred for 14 hours at a temperature falling in a range of 70 to 75° C. In this regard, the reaction solution was analyzed by gas chromatography to find that a conversion rate of chloroacetaldehyde=dimethyl=acetal was 95.5%.

After a temperature of the reaction solution was lowered down to room temperature, the reaction solution was filtrated to remove salts produced, and the filtrate was concentrated under reduced pressure and subjected to simple distillation. (2-Hydroxyethylthio)acetaldehyde=dimethyl=acetal 334.0 g (1.89 mol) showing the following physical properties was obtained in the form of a pale yellow transparent oil on the conditions of a pressure of 545 Pa, a vessel inside temperature of 146° C. and a distillation temperature of 122° C. (purity: 94.3%, yield: 80%).

$^1$H-NMR (300 MHz, CDCl$_3$, TMS, ppm) δ: 2.60 to 2.67 (1H, br), 2.71 (2H, d, J=5.4 Hz), 2.77 (2H, t, J=5.8 Hz), 3.37 (6H, s), 3.73 (2H, dt, J=5.7, 5.8 Hz), 4.48 (1H, t, J=5.4 Hz)

Next, a four neck flask having a content volume of 1 L equipped with a thermometer, a distilling head and a stirring device was charged with 672.3 g of water, 100 g (565 mmol) of (2-hydroxyethylthio)acetaldehyde=dimethyl=acetal and 1.67 g of a 5.0 mass % sulfuric acid aqueous solution. The mixture was stirred for 4 hours on the conditions of a pressure of 16.0 kPa and a vessel inside temperature of 70° C. while removing water and resulting methanol by distillation. In this regard, the reaction solution was analyzed by gas chromatography to find that a conversion rate of (2-hydroxyethylthio)acetaldehyde=dimethyl=acetal was 94.2%.

After the vessel inside temperature was lowered down to room temperature, the pH was adjusted to 8.0 by a 4.0 mass % sodium hydroxide aqueous solution, and the reaction solution was extracted three times with 400 g of ethyl acetate. The extracts of three extractions thus obtained were put together and concentrated under reduced pressure to obtain 63.3 g of the concentrate. The above concentrate was dissolved in 158 g of diisopropyl ether at 50° C., and the solution was slowly cooled down to 8° C., followed by separating a white crystal deposited by filtering, whereby 35.1 g (287 mmol) of 1,4-oxathiane-2-ol was obtained in the form of a white crystal (purity: 98.2%, yield: 51%).

Example 2

Production of 1,4-oxathiane-2-yl=methacrylate

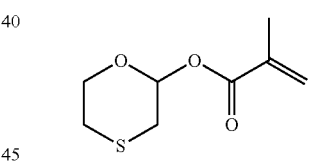

A four neck flask having a content volume of 2 L equipped with a thermometer, a dropping funnel and a stirring device was charged with 431 g of THF, 42.9 g (351 mmol) of 1,4-oxathiane-2-ol obtained in Example 1 and 0.61 g of phenothiazine, and an inside of the flask was substituted with nitrogen. Triethylamine 71.1 g (703 mmol) was dropwise added thereto from the dropping funnel while cooling the flask on an ice bath so that the temperature was controlled in a range of 2 to 5° C. Next, 51.3 g (486 mmol) of methacrylic chloride was dropwise added thereto so that the temperature was maintained in a range of 5 to 10° C. After finishing dropwise adding, stirring was continued at 3 to 6° C. for 1.5 hour. In this regard, the reaction solution was analyzed by gas chromatography to find that a conversion rate of 1,4-oxathiane-2-ol was 99.9%. Water 290 g was slowly dropwise added from the dropping funnel so that the temperature was maintained at lower than 20° C., and after finishing dropwise adding, the ice bath was removed to leave the inside temperature to 24° C. 4-Dimethylaminopyridine 3.0 g was added thereto, and the mixture was stirred at 24 to 26° C. for 3 hours. In this regard, the reaction solution was analyzed by gas chromatography to find that a ratio of methacrylic anhydride to 1,4-oxathiane-2-yl=methacrylate was methacrylic anhydride:1,4-oxathiane-2-yl=methacrylate=0.3:99.7 (area ratio). The above mixture was transferred into a separating funnel having a content volume of 2 L and extracted three times with 285 g of ethyl acetate. The extract of three extractions thus obtained was put into a separating funnel having a content volume of 2 L and washed in order with three times 285 g of a 1% hydrochloric acid aqueous solution and 285 g of water. p-Methoxyphenol 0.017 g and phenothiazine 0.017 g were added thereto, and the solvent was removed by distillation under reduced pressure to obtain 82.4 g of a crude for distillation. A molecular distillation equipment "MS-300" (manufactured by SHIBATA SCIENTIFIC TECHNOLOGY LTD.) was used for the distillation. The above crude was allowed to flow therethrough at a pressure of 13.3 to 26.6 Pa and a temperature of 30 to 35° C. to obtain a high boiling fraction, and the above high boiling fraction was allowed to flow therethrough at a pressure of 9.3 to 13.3 Pa and a temperature of 40 to 45° C. to obtain 54.4 g (285 mmol) of 1,4-oxathiane-2-yl=methacrylate showing the following physical properties as a low boiling fraction in the form of a colorless and transparent oil (purity: 98.7%, yield: 81%).

$^1$H-NMR (300 MHz, CDCl$_3$, TMS, ppm) δ: 1.97 (3H, s), 2.58 to 2.63 (2H, m), 2.73 (1H, dd, J=6.0, 13.4 Hz), 2.83 (1H, dd, J=2.4, 13.4 Hz), 3.97 (1H, m), 4.29 (1H, m), 5.66 (1H, m), 5.98 (1H, ddd=1.1, 2.4, 6.0 Hz), 6.23 (1H, s)

log P: 1.33
SP: 17.8 (J/mol)$^{0.5}$

Example 3

Production of 1,4-dioxane-2-ol

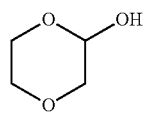

A four neck flask having a content volume of 1 L equipped with a thermometer, a reflux condenser and a stirring device was charged with 350.0 g (5.64 mol) of 1,2-ethanediol. The flask was cooled on an ice bath, and 237.0 g (4.23 mol) of potassium hydroxide was added thereto little by little while stirring so that the temperature did not exceed 50° C. After finishing addition of potassium hydroxide, 351.2 g (2.82 mol) of chloroacetaldehyde=dimethyl=acetal was dropwise added thereto so that the temperature was controlled in a range of 40 to 50° C. After finishing dropwise adding, heating was started, and stirring was continued for 22 hours at a temperature falling in a range of 110 to 112° C. In this regard, the reaction solution was analyzed by gas chromatography to find that a conversion rate of chloroacetaldehyde=dimethyl=acetal was 78.6%.

After a temperature of the reaction solution was lowered down to room temperature, the reaction solution was filtrated to remove salts produced, and the filtrate was subjected to simple distillation. A transparent oil 315.6 g was obtained on the conditions of a pressure of 533 to 933 Pa, a vessel inside temperature of 105 to 119° C. and a distillation temperature of 96 to 102° C. The above oil was analyzed by gas chromatography to find that a purity of 2-(2,2-dimethoxyethyloxy)ethanol was 50.0%. Next, the oil obtained was distilled by means of a distillation column filled with packing McMahon. 2-(2,2-Dimethoxyethyloxy)ethanol 101.8 g (0.66 mol) was obtained in the form of a colorless and transparent oil on the conditions of a pressure of 133 to 493 Pa, a vessel inside temperature of 113 to 137° C. and a distillation temperature of 82.5 to 87.0° C. (purity: 97.5%, yield: 23.5% based on chloroacetaldehyde=dimethyl=acetal).

Next, a four neck flask having a content volume of 200 mL equipped with a thermometer, a distilling head and a stirring device was charged with 137.4 g of water, 42.2 mg of sulfuric acid and 20.0 g (130 mmol) of 2-(2,2-dimethoxyethyloxy) ethanol. The mixture was stirred for 11 hours on the conditions of a pressure of 18.0 kPa and a vessel inside temperature of 60° C. while removing water and resulting methanol by distillation. In this regard, the reaction solution was analyzed by gas chromatography to find that a conversion rate of 2-(2,2-dimethoxyethyloxy)ethanol was 99.6%.

After the vessel inside temperature was lowered down to room temperature, the pH was adjusted to 8.3 by a 10.0 mass % sodium hydroxide aqueous solution, and the reaction solution was extracted three times with 300 g of ethyl acetate. The extracts of three extractions thus obtained were put together and concentrated under reduced pressure, and 17.41 g of the concentrate obtained was subjected to simple distillation. 1,4-Dioxane-2-ol 8.50 g (75.6 mmol) was obtained in the form of a colorless and transparent oil on the conditions of a pressure of 1.60 kPa, a vessel inside temperature of 97 to 115° C. and a distillation temperature of 92 to 96° C. (purity: 92.5%, yield: 58.1% based on 2-(2,2-dimethoxyethyloxy) ethanol).

Example 4

Production of 1,4-dioxane-2-yl=methacrylate

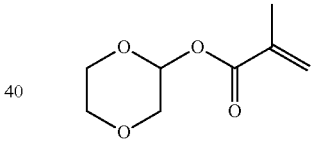

A four neck flask having a content volume of 50 mL equipped with a thermometer and a stirring device was substituted with nitrogen and then charged in order with 10.23 g of THF, 3.00 g (26.7 mmol) of 1,4-dioxane-2-ol obtained in Example 3, 53 mg of phenothiazine, 5.56 g (54.9 mmol) of triethylamine and 0.23 g (1.87 mmol) of 4-(dimethylamino) pyridine. Next, 4.01 g (38.4 mmol) of methacrylic chloride was dropwise added thereto so that the temperature was controlled in a range of 3 to 5° C. After finishing dropwise adding, stirring was continued at 4 to 10° C. for 4 hours. In this regard, the reaction solution was analyzed by gas chromatography to find that a conversion rate of 1,4-dioxane-2-ol was 99.9%. Water 20 g was slowly dropwise added thereto so that the temperature was maintained at lower than 10° C., and after dropwise adding, the ice bath was removed to leave the inside temperature to 22° C., followed by stirring the solution for one hour. In this regard, the reaction solution was analyzed by gas chromatography to find that a ratio of methacrylic anhydride to 1,4-dioxane-2-yl=methacrylate was methacrylic anhydride:1,4-dioxane-2-yl=methacrylate=0.1:99.9 (area ratio).

The above mixture was transferred into a separating funnel having a content volume of 100 mL and extracted three times with 20 g of ethyl acetate. The extract of three extractions thus obtained was put into a separating funnel having a content volume of 100 mL and washed in order every once with 20 g of a 2% hydrochloric acid aqueous solution, 20 g of a 1% sodium hydroxide aqueous solution, 20 g of a 5% sodium hydrogencarbonate aqueous solution and 10 g of a saturated brine. The concentrate obtained by removing the solvent by distillation was refined by silica gel chromatography (a developing solvent was n-hexane:ethyl acetate=8:1 (volume ratio)) to thereby obtain 4.10 g (23.6 mmol) of 1,4-dioxane-2-yl=methacrylate showing the following physical properties in the form of a colorless and transparent oil (purity: 99.1%, yield: 88.5%).

$^{1}$H-NMR (300 MHz, CDCl$_3$, TMS, ppm) δ: 1.98 (3H, s), 3.65 (1H, dt, J=11.7, 2.7 Hz), 3.74 to 3.87 (m, 4H), 4.07 to 4.21 (m, 1H), 5.65 to 5.68 (m, 1H), 5.91 (1H, t, J=2.0 Hz), 6.25 (s, 1H)

log P: 0.89
SP: 18.3 (J/mol)$^{0.5}$

Example 5

Production of 1,4-oxathiepane-2-ol

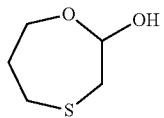

A four neck flask having a content volume of 500 mL equipped with a thermometer, a reflux condenser and a stirring device was charged with 138 g of methanol. The flask was cooled on an ice bath, and 20.6 g (515 mmol) of sodium hydroxide was added thereto little by little while stirring so that the temperature did not exceed 50° C. After finishing addition of sodium hydroxide, stirring was continued, and when the temperature was 2 to 5° C., 50.0 g (515 mmol) of 3-mercapto-1-propanol was slowly added thereto from a dropping funnel so that the temperature was controlled in a range of 5 to 10° C. After finishing dropwise adding, stirring was continued for one hour, and 47.5 g (381 mmol) of chloroacetaldehyde=dimethyl=acetal was dropwise added from a dropping funnel so that the temperature was controlled in a range of 5 to 10° C. After finishing dropwise adding, heating was started, and stirring was continued for 15 hours at a temperature falling in a range of 75 to 80° C. In this regard, the reaction solution was analyzed by gas chromatography to find that a conversion rate of chloroacetaldehyde=dimethyl=acetal was 92.0%.

After a temperature of the reaction solution was lowered down to room temperature, the reaction solution was filtrated to remove salts produced, and the filtrate was concentrated under reduced pressure and subjected to simple distillation to obtain 55.3 g (289 mmol) of 3-(2,2-dimethoxyethylthio)-1-propanol in the form of a pale yellow transparent oil (purity: 94.2%, yield: 75.9% based on chloroacetaldehyde=dimethyl=acetal).

Next, a four neck flask having a content volume of 200 mL equipped with a thermometer, a distilling head and a stirring device was charged with 137.4 g of water, 42.2 mg of sulfuric acid and 24.9 g (130 mmol) of 3-(2,2-dimethoxyethylthio)-1-propanol. The mixture was stirred for 11 hours on the conditions of a pressure of 18.0 kPa and a vessel inside temperature of 60° C. while removing water and resulting methanol by distillation. In this regard, the reaction solution was analyzed by gas chromatography to find that a conversion rate of 3-(2,2-dimethoxyethylthio)-1-propanol was 99.6%.

After the vessel inside temperature was lowered down to room temperature, the pH was adjusted to 8.0 by a 10.0 mass % sodium hydroxide aqueous solution, and the reaction solution was extracted three times with 300 g of ethyl acetate. The extracts of three extractions thus obtained were put together and concentrated under reduced pressure, and the concentrate obtained was refined by silica gel chromatography to obtain 5.90 g (43.3 mmol) of 1,4-oxathiepane-2-ol (purity: 98.5%, yield: 33.3% based on 3-(2,2-dimethoxyethylthio)-1-propanol).

Example 6

Production of 1,4-oxathiepane-2-yl=methacrylate

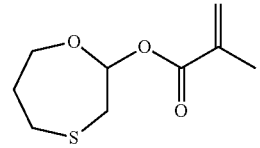

A four neck flask having a content volume of 50 mL equipped with a thermometer and a stirring device was substituted with nitrogen and then charged in order with 10.23 g of THF, 3.64 g (26.7 mmol) of 1,4-oxathiepane-2-ol obtained in Example 5, 53 mg of phenothiazine, 5.56 g (54.9 mmol) of triethylamine and 0.23 g (1.87 mmol) of 4-(dimethylamino)pyridine. Next, 4.01 g (38.4 mmol) of methacrylic chloride was dropwise added thereto so that the temperature was controlled in a range of 3 to 5° C. After finishing dropwise adding, stirring was continued at 4 to 10° C. for 5 hours. In this regard, the reaction solution was analyzed by gas chromatography to find that a conversion rate of 1,4-oxathiepane-2-ol was 99.9%. Water 20 g was slowly dropwise added thereto so that the temperature was maintained at lower than 10° C., and after dropwise adding, the ice bath was removed to leave the inside temperature to 23° C., followed by stirring the solution for one hour. In this regard, the reaction solution was analyzed by gas chromatography to find that a ratio of methacrylic anhydride to 1,4-oxathiepane-2-yl=methacrylate was methacrylic anhydride:1,4-oxathiepane-2-yl=methacrylate=0.2:99.8 (area ratio).

The above mixture was transferred into a separating funnel having a content volume of 100 mL and extracted three times with 20 g of ethyl acetate. The extract of three extractions thus obtained was put into a separating funnel having a content volume of 100 mL and washed in order every once with 20 g of a 2% hydrochloric acid aqueous solution, 20 g of a 1% sodium hydroxide aqueous solution, 20 g of a 5% sodium hydrogencarbonate aqueous solution and 10 g of a saturated brine. The concentrate obtained by removing the solvent by distillation was refined by silica gel chromatography to thereby obtain 4.67 g (22.7 mmol) of 1,4-oxathiepane-2-yl=methacrylate (purity: 98.2%, yield: 84.9%).

Example 7

Production of 1,4-dioxepane-2-ol

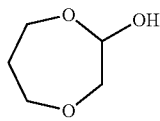

A four neck flask having a content volume of 2 L equipped with a thermometer, a reflux condenser and a stirring device was charged with 429.1 g (5.64 mol) of 1,3-propanediol. The flask was cooled on an ice bath, and 237.0 g (4.23 mol) of potassium hydroxide was added thereto little by little while stirring so that the temperature did not exceed 50° C. After finishing addition of potassium hydroxide, 351.2 g (2.82 mol) of chloroacetaldehyde=dimethyl=acetal was dropwise added at a temperature falling in a range of 40 to 50° C. After finishing dropwise adding, heating was started, and stirring was continued for 22 hours at a temperature falling in a range of 110 to 112° C. In this regard, the reaction solution was analyzed by gas chromatography to find that a conversion rate of chloroacetaldehyde=dimethyl=acetal was 69.2%.

After a temperature of the reaction solution was lowered down to room temperature, the reaction solution was filtrated to remove salts produced, and the filtrate was distilled to obtain 103.3 g (0.61 mol) of 3-(2,2-dimethoxyethyloxy)-1-propanol in the form of a colorless and transparent oil (purity: 97.0%, yield: 21.6% based on chloroacetaldehyde=dimethyl=acetal).

Next, a four neck flask having a content volume of 200 mL equipped with a thermometer, a distilling head and a stirring device was charged with 137.4 g of water, 42.2 mg of sulfuric acid and 22.0 g (130 mmol) of 3-(2,2-dimethoxyethyloxy)-1-propanol. The mixture was stirred for 11 hours on the conditions of a pressure of 18.0 kPa and a vessel inside temperature of 60° C. while removing water and resulting methanol by distillation. In this regard, the reaction solution was analyzed by gas chromatography to find that a conversion rate of 3-(2,2-dimethoxyethyloxy)-1-propanol was 99.6%.

After the vessel inside temperature was lowered down to room temperature, the pH was adjusted to 8.3 by a 10.0 mass % sodium hydroxide aqueous solution, and the reaction solution was extracted three times with 300 g of ethyl acetate. The extracts of three extractions thus obtained were put together and concentrated under reduced pressure, and the concentrate obtained was refined by silica gel chromatography to obtain 5.40 g (44.7 mmol) of 1,4-dioxepane-2-ol (purity: 97.9%, yield: 34.4% based on 3-(2,2-dimethoxyethyloxy)-1-propanol).

Example 8

Production of 1,4-dioxepane-2-yl=methacrylate

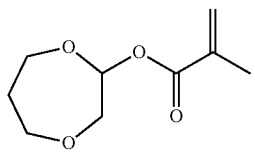

A four neck flask having a content volume of 50 mL equipped with a thermometer and a stirring device was substituted with nitrogen and then charged in order with 10.23 g of THF, 3.22 g (26.7 mmol) of 1,4-dioxepane-2-ol obtained in Example 7, 53 mg of phenothiazine, 5.56 g (54.9 mmol) of triethylamine and 0.23 g (1.87 mmol) of 4-(dimethylamino)pyridine. Next, 4.01 g (38.4 mmol) of methacrylic chloride was dropwise added thereto so that the temperature was controlled in a range of 3 to 5° C. After finishing dropwise adding, stirring was continued at 4 to 10° C. for 5 hours. In this regard, the reaction solution was analyzed by gas chromatography to find that a conversion rate of 1,4-dioxepane-2-ol was 99.9%. Water 20 g was slowly dropwise added thereto so that the temperature was maintained at lower than 10° C., and after dropwise adding, the ice bath was removed to leave the inside temperature to 23° C., followed by stirring the solution for one hour. In this regard, the reaction solution was analyzed by gas chromatography to find that a ratio of methacrylic anhydride to 1,4-dioxepane-2-yl=methacrylate was methacrylic anhydride:1,4-dioxepane-2-yl=methacrylate=0.1:99.9 (area ratio).

The above mixture was transferred into a separating funnel having a content volume of 100 mL and extracted three times with 20 g of ethyl acetate. The extract of three extractions thus obtained was put into a separating funnel having a content volume of 100 mL and washed in order every once with 20 g of a 2% hydrochloric acid aqueous solution, 20 g of a 1% sodium hydroxide aqueous solution, 20 g of a 5% sodium hydrogencarbonate aqueous solution and 10 g of a saturated brine. The concentrate obtained by removing the solvent by distillation was refined by silica gel chromatography to thereby obtain 4.08 g (21.7 mmol) of 1,4-dioxepane-2-yl=methacrylate (purity: 99.0%, yield: 81.2%).

Example 9

Production of 6-methyl-1,4-oxathiane-2-ol

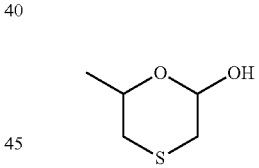

A four neck flask having a content volume of 500 mL equipped with a thermometer, a reflux condenser and a stirring device was charged with 138 g of methanol. The flask was cooled on an ice bath, and 20.6 g (515 mmol) of sodium hydroxide was added thereto little by little while stirring so that the temperature did not exceed 50° C. After finishing addition of sodium hydroxide, stirring was continued, and when the temperature was 2 to 5° C., 50.0 g (515 mmol) of 1-mercapto-2-propanol was slowly added thereto from a dropping funnel so that the temperature was controlled in a range of 5 to 10° C. After finishing dropwise adding, stirring was continued for one hour, and 47.5 g (381 mmol) of chloroacetaldehyde=dimethyl=acetal was dropwise added from a dropping funnel so that the temperature was controlled in a range of 5 to 10° C. After finishing dropwise adding, heating was started, and stirring was continued for 15 hours at a temperature falling in a range of 75 to 80° C. In this regard, the reaction solution was analyzed by gas chromatography to find that a conversion rate of chloroacetaldehyde=dimethyl=acetal was 90.9%.

After a temperature of the reaction solution was lowered down to room temperature, the reaction solution was filtrated to remove salts produced, and the filtrate was concentrated under reduced pressure and subjected to simple distillation to obtain 51.1 g (263 mmol) of 1-(2,2-dimethoxyethylthio)-2-propanol in the form of a pale yellow transparent oil (purity: 92.9%, yield: 69.1% based on chloroacetaldehyde=dimethyl=acetal).

Next, a four neck flask having a content volume of 200 mL equipped with a thermometer, a distilling head and a stirring device was charged with 137.4 g of water, 42.2 mg of sulfuric acid and 25.2 g (130 mmol) of 1-(2,2-dimethoxyethylthio)-2-propanol. The mixture was stirred for 11 hours on the conditions of a pressure of 18.0 kPa and a vessel inside temperature of 60° C. while removing water and resulting methanol by distillation. In this regard, the reaction solution was analyzed by gas chromatography to find that a conversion rate of 1-(2,2-dimethoxyethylthio)-2-propanol was 99.6%.

After the vessel inside temperature was lowered down to room temperature, the pH was adjusted to 8.1 by a 10.0 mass % sodium hydroxide aqueous solution, and the reaction solution was extracted three times with 300 g of ethyl acetate. The extracts of three extractions thus obtained were put together and concentrated under reduced pressure, and the concentrate obtained was refined by silica gel chromatography to obtain 11.2 g (82.6 mmol) of 6-methyl-1,4-oxathiane-2-ol (purity: 99.0%, yield: 63.6% based on 1-(2,2-dimethoxyethylthio)-2-propanol).

Example 10

Production of 6-methyl-1,4-oxathiane-2-yl=methacrylate

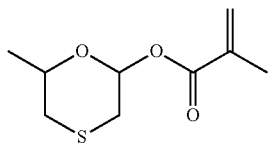

A four neck flask having a content volume of 50 mL equipped with a thermometer and a stirring device was substituted with nitrogen and then charged in order with 10.23 g of THF, 3.62 g (26.7 mmol) of 6-methyl-1,4-oxathiane-2-ol obtained in Example 9, 53 mg of phenothiazine, 5.56 g (54.9 mmol) of triethylamine and 0.23 g (1.87 mmol) of 4-(dimethylamino)pyridine. Next, 4.01 g (38.4 mmol) of methacrylic chloride was dropwise added thereto so that the temperature was controlled in a range of 3 to 5° C. After finishing dropwise adding, stirring was continued at 4 to 10° C. for 5 hours. In this regard, the reaction solution was analyzed by gas chromatography to find that a conversion rate of 6-methyl-1,4-oxathiane-2-ol was 99.9%. Water 20 g was slowly dropwise added thereto so that the temperature was maintained at lower than 10° C., and after dropwise adding, the ice bath was removed to leave the inside temperature cooled down to 23° C., followed by stirring the solution for one hour. In this regard, the reaction solution was analyzed by gas chromatography to find that a ratio of methacrylic anhydride to 6-methyl-1,4-oxathiane-2-yl=methacrylate was methacrylic anhydride:6-methyl-1,4-oxathiane-2-yl=methacrylate=0.1:99.9 (area ratio).

The above mixture was transferred into a separating funnel having a content volume of 100 mL and extracted three times with 20 g of ethyl acetate. The extract of three extractions thus obtained was put into a separating funnel having a content volume of 100 mL and washed in order every once with 20 g of a 2% hydrochloric acid aqueous solution, 20 g of a 1% sodium hydroxide aqueous solution, 20 g of a 5% sodium hydrogencarbonate aqueous solution and 10 g of a saturated brine. The concentrate obtained by removing the solvent by distillation was refined by silica gel chromatography to thereby obtain 5.06 g (24.5 mmol) of 6-methyl-1,4-oxathiane-2-yl=methacrylate (purity: 97.9%, yield: 91.8%).

Example 11

Production of 5,6-dimethyl-1,4-dioxane-2-ol

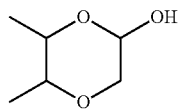

A four neck flask having a content volume of 2 L equipped with a thermometer, a reflux condenser and a stirring device was charged with 518.6 g (5.64 mol) of 2,3-butanediol. The flask was cooled on an ice bath, and 237.0 g (4.23 mol) of potassium hydroxide was added thereto little by little while stirring so that the temperature did not exceed 50° C. After finishing addition of potassium hydroxide, 351.2 g (2.82 mol) of chloroacetaldehyde=dimethyl=acetal was dropwise added at a temperature falling in a range of 40 to 50° C. After finishing dropwise adding, heating was started, and stirring was continued for 22 hours at a temperature falling in a range of 110 to 112° C. In this regard, the reaction solution was analyzed by gas chromatography to find that a conversion rate of chloroacetaldehyde=dimethyl=acetal was 57.9%.

After a temperature of the reaction solution was lowered down to room temperature, the reaction solution was filtrated to remove salts produced, and the filtrate was distilled to obtain 94.4 g (0.51 mol) of 3-(2,2-dimethoxyethyloxy)-2-butanol in the form of a colorless and transparent oil (purity: 95.9%, yield: 18.0% based on chloroacetaldehyde=dimethyl=acetal).

Next, a four neck flask having a content volume of 200 mL equipped with a thermometer, a distilling head and a stirring device was charged with 137.4 g of water, 42.2 mg of sulfuric acid and 24.2 g (130 mmol) of 3-(2,2-dimethoxyethyloxy)-2-butanol. The mixture was stirred for 11 hours on the conditions of a pressure of 18.0 kPa and a vessel inside temperature of 60° C. while removing water and resulting methanol by distillation. In this regard, the reaction solution was analyzed by gas chromatography to find that a conversion rate of 3-(2,2-dimethoxyethyloxy)-2-butanol was 99.6%. After the vessel inside temperature was lowered down to room temperature, the pH was adjusted to 8.0 by a 10.0 mass % sodium hydroxide aqueous solution, and the reaction solution was extracted three times with 300 g of ethyl acetate. The extracts of three extractions thus obtained were put together and concentrated under reduced pressure, and the concentrate obtained was refined by silica gel chromatography to obtain 9.66 g (72.2 mmol) of 5,6-dimethyl-1,4-dioxane-2-ol in the form of a colorless and transparent oil (purity: 98.8%, yield: 55.5% based on 3-(2,2-dimethoxyethyloxy)-2-butanol).

Example 12

Production of 5,6-dimethyl-1,4-dioxane-2-yl=methacrylate

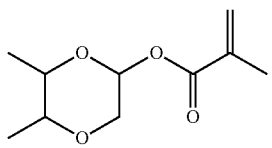

A four neck flask having a content volume of 50 mL equipped with a thermometer and a stirring device was substituted with nitrogen and then charged in order with 10.23 g of THF, 3.57 g (26.7 mmol) of 5,6-dimethyl-1,4-dioxane-2-ol obtained in Example 11, 53 mg of phenothiazine, 5.56 g (54.9 mmol) of triethylamine and 0.23 g (1.87 mmol) of 4-(dimethylamino)pyridine. Next, 4.01 g (38.4 mmol) of methacrylic chloride was dropwise added thereto so that the temperature was controlled in a range of 3 to 5° C. After finishing dropwise adding, stirring was continued at 4 to 10° C. for 5 hours. In this regard, the reaction solution was analyzed by gas chromatography to find that a conversion rate of 5,6-dimethyl-1,4-dioxane-2-ol was 99.7%. Water 20 g was slowly dropwise added thereto so that the temperature was maintained at lower than 10° C., and after dropwise adding, the ice bath was removed to leave the inside temperature to 23° C., followed by stirring the solution for one hour. In this regard, the reaction solution was analyzed by gas chromatography to find that a ratio of methacrylic anhydride to 5,6-dimethyl-1,4-dioxane-2-yl=methacrylate was methacrylic anhydride:5,6-dimethyl-1,4-dioxane-2-yl=methacrylate=0.3:99.7 (area ratio).

The above mixture was transferred into a separating funnel having a content volume of 100 mL and extracted three times with 20 g of ethyl acetate. The extract of three extractions thus obtained was put into a separating funnel having a content volume of 100 mL and washed in order every once with 20 g of a 2% hydrochloric acid aqueous solution, 20 g of a 1% sodium hydroxide aqueous solution, 20 g of a 5% sodium hydrogencarbonate aqueous solution and 10 g of a saturated brine. The concentrate obtained by removing the solvent by distillation was refined by silica gel chromatography to thereby obtain 4.67 g (22.8 mmol) of 5,6-dimethyl-1,4-dioxane-2-yl=methacrylate (purity: 97.8%, yield: 85.4%).

Example 13

Evaluation of a Reactivity of the Acrylic Ester Derivative (I) to Acid

An NMR tube was charged with $2.73 \times 10^{-4}$ mol of 1,4-oxathiane-2-yl=methacrylate obtained in Example 2, 0.69 mL of 1,1,2,2-tetrachloroethane-$d_2$ and $1.47 \times 10^{-6}$ mol of methanesulfonic acid, and it was provided with a cap and shaken up well. The above NMR tube was dipped in an oil bath of 120° C. for several seconds to several minutes, and then the NMR tube was taken out and put in an ice bath to cool the reaction solution. Then, $^1$H-NMR thereof was immediately measured by means of "NMR Gemini-300" (trade name, manufactured by Varian Technologies Limited). Unreacted methacrylic ester and acrylic acid produced by the reaction were observed in the NMR chart of methacrylic acid reacted, and a conversion rate in the dissociation reaction was determined from the respective vinyl protons. Thereafter, an operation in which the above NMR tube was dipped in the oil bath of 120° C. for several seconds to several minutes and cooled in the ice bath to measure the $^1$H-NMR was repeated several times to determine the conversion rates to the reaction time in several points. The conversion rates versus the reaction time determined above were plotted on an X axis of the time (s) and a Y axis of ln (1−X) according to the following primary reaction rate equation (equation 1)

(Equation 1):

$$-kt = \ln(1-X) \quad \text{(Equation 1)}$$

(wherein k represents a rate constant (s$^{-1}$); t represents time (s); and X represents a conversion rate), and a rate constant in deprotection reaction of methacrylic ester at 120° C. was determined from a gradient of the straight line.

2-Methacryloyloxy-2-methyladamantane which was usually used was selected as a comparative object to determine the rate constant at 120° C. by the same method as in 1,4-oxathiane-2-yl=methacrylate.

A relative activity of 1,4-oxathiane-2-yl=methacrylate to 2-methacryloyloxy-2-methyladamantane was determined by dividing a rate constant in deprotection reaction of 1,4-oxathiane-2-yl=methacrylate by a rate constant in deprotection reaction of 2-methacryloyloxy-2-methyladamantane, and it was set to an index of the reactivity (activity in deprotection reaction) to acid.

The operation and the analysis described above were carried out as well at 140° C. The results thereof are shown in Table 1.

Example 14

Evaluation of a Reactivity of the Acrylic Ester Derivative (I) to Acid

The experiment was carried out in the same manner as in Example 13, except that in Example 13, 1,4-dioxane-2-yl=methacrylate obtained in Example 4 was used in place of 1,4-oxathiane-2-yl=methacrylate, and the reactivity (activity in deprotection reaction) to acid was evaluated. The results thereof are shown in Table 1.

Example 15

Evaluation of a Reactivity of the Acrylic Ester Derivative (I) to Acid

The experiment was carried out in the same manner as in Example 13, except that in Example 13, 1,4-oxathiepane-2-yl=methacrylate obtained in Example 6 was used in place of 1,4-oxathiane-2-yl=methacrylate, and the reactivity (activity in deprotection reaction) to acid was evaluated. The results thereof are shown in Table 1.

Example 16

Evaluation of a Reactivity of the Acrylic Ester Derivative (I) to Acid

The experiment was carried out in the same manner as in Example 13, except that in Example 13, 1,4-dioxepane-2-yl=methacrylate obtained in Example 8 was used in place of 1,4-oxathiane-2-yl=methacrylate, and the reactivity (activity in deprotection reaction) to acid was evaluated. The results thereof are shown in Table 1.

Example 17

Evaluation of a Reactivity of the Acrylic Ester Derivative (I) to Acid

The experiment was carried out in the same manner as in Example 13, except that in Example 13, 6-methyl-1,4-oxathiane-2-yl=methacrylate obtained in Example 10 was used in place of 1,4-oxathiane-2-yl=methacrylate, and the reactivity (activity in deprotection reaction) to acid was evaluated. The results thereof are shown in Table 1.

Example 18

Evaluation of a Reactivity of the Acrylic Ester Derivative (I) to Acid

The experiment was carried out in the same manner as in Example 13, except that in Example 13, 5,6-dimethyl-1,4-dioxane-2-yl=methacrylate obtained in Example 12 was used in place of 1,4-oxathiane-2-yl=methacrylate, and the reactivity (activity in deprotection reaction) to acid was evaluated. The results thereof are shown in Table 1.

TABLE 1 relative activity in deprotection reaction in the presence of methanesulfonic acid

| | Acrylic ester derivative (I) | Relative activity (120° C.) | Relative activity (140° C.) |
|---|---|---|---|
| | 2-methacryloyloxy-2-methyladamantane | 1.00 | 1.00 |
| Example 13 | 1,4-oxathiane-2-yl = methacrylate | 14.25 | 7.47 |
| Example 14 | 1,4-dioxane-2-yl = methacrylate | 4.93 | 4.36 |
| Example 15 | 1,4-oxathiepane-2-yl = methacrylate | 12.36 | 6.98 |
| Example 16 | 1,4-dioxepane-2-yl = methacrylate | 14.37 | 9.21 |
| Example 17 | 6-methyl-1,4-oxathiane-2-yl = methacrylate | 14.02 | 7.98 |
| Example 18 | 5,6-dimethyl-1,4-dioxane-2-yl = methacrylate | 6.74 | 5.22 |

Examples 19 to 24

Activation Energy in Deprotection Reaction of the Acrylic Ester Derivative (I)

The rate constants in the deprotection reaction at 120° C. and 140° C. which were determined by analysis in Examples 13 to 18 were substituted for the following equation (Equation 2) to determine the activation energy (E) in the deprotection reaction of the respective acrylic ester derivatives (I). The results thereof are shown in Table 2.

$$\log \frac{k_2}{k_1} = \frac{E}{2.303R}\left(\frac{1}{T_1} - \frac{1}{T_2}\right) \quad \text{(Equation 2)}$$

(wherein $k_1$ represents a rate constant ($s^{-1}$) in the deprotection reaction at 120° C.; $k_2$ represents a rate constant ($s^{-1}$) in the deprotection reaction at 140° C.; E represents an activation energy (kcal/mol) in the deprotection reaction; R represents an air constant (1.987 cal·$K^{-1}$·$mol^{-1}$; $T_1$ represents an absolute temperature (K) of 120° C.; and $T_2$ represents an absolute temperature (K) of 140° C.).

TABLE 2 activation energy in deprotection reaction

| | Acrylic ester derivative (I) | Activation energy (kcal/mol) |
|---|---|---|
| | 2-methacryloyloxy-2-methyladamantane | 18.8 |
| Example 19 | 1,4-oxathiane-2-yl = methacrylate | 8.3 |
| Example 20 | 1,4-dioxane-2-yl = methacrylate | 16.8 |
| Example 21 | 1,4-oxathiepane-2-yl = methacrylate | 9.5 |
| Example 22 | 1,4-dioxepane-2-yl = methacrylate | 11.6 |
| Example 23 | 6-methyl-1,4-oxathiane-2-yl = methacrylate | 9.7 |
| Example 24 | 5,6-dimethyl-1,4-dioxane-2-yl = methacrylate | 14.6 |

It has been found from the results shown in Tables 1 and 2 that when compared with publicly known methacrylic ester, the acrylic ester derivatives (I) of the present invention have a high reactivity to acid (refer to Examples 13 to 18) and that they have a low activation energy (refer to Examples 19 to 24), and therefore they are useful as raw materials for chemically amplified resists.

Example 25

Production of Polymer (a)

A round-bottom flask having a content volume of 300 mL equipped with an electromagnetic stirring device, a reflux condenser and a thermometer was charged with 8.48 g (42.5 mmol) of 1,4-oxathiane-2-yl=methacrylate obtained in Example 2, 10.05 g (42.5 mmol) of 3-hydroxy-1-adamantyl=methacrylate, 150.2 g of 1,4-dioxane and 1.96 g (7.90 mmol) of 2,2'-azobis(2,4-dimethylvaleronitrile) under nitrogen atmosphere to carry out polymerization reaction at 60 to 62° C. for 6 hours.

A reaction mixture obtained was dropwise added to diisopropyl ether of about 20 times mass based on the reaction mixture at room temperature while stirring, and a precipitate produced was obtained by filtering. The above precipitate was dissolved in 150.0 g of THF, and the solution prepared was dropwise added to a diisopropyl ether/methanol mixed solution (mass ratio diisopropyl ether:methanol=4:1) of the same mass as described above while stirring. A precipitate produced was separated by filtering and then washed with the diisopropyl ether/methanol mixed solution (mass ratio diisopropyl ether:methanol=4:1) of the same mass as described above, whereby a white precipitate was obtained. The above precipitate was dried at 50° C. for 10 hours under reduced pressure (26.7 Pa) to obtain 11.3 g of a polymer (a) comprising a repetitive unit shown below. The polymer (a) thus obtained had Mw of 17700 and a dispersion degree of 1.95.

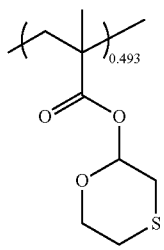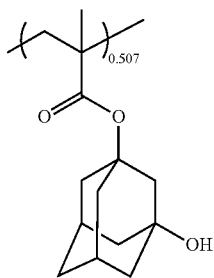

polymer (a)

Example 26

Production of Polymer (b)

A round-bottom flask having a content volume of 200 mL equipped with an electromagnetic stirring device, a reflux condenser and a thermometer was charged with 8.17 g (42.7 mmol) of 1,4-oxathiane-2-yl=methacrylate, 9.49 g (42.7 mmol) of 5-methacryloyloxy-2,6-norbornanecarbolactone, 140.0 g of 1,4-dioxane and 2.86 g (11.5 mmol) of 2,2'-azobis(2,4-dimethylvaleronitrile) under nitrogen atmosphere to carry out polymerization reaction at 60 to 63° C. for 4 hours.

A reaction mixture obtained was dropwise added to methanol of about 20 times mass based on the reaction mixture at room temperature while stirring, and a precipitate produced was separated by filtering. The above precipitate was dissolved in 80.0 g of 1,4-dioxane, and the solution prepared was dropwise added to a diisopropyl ether/methanol mixed solution (mass ratio diisopropyl ether:methanol=4:1) of the same mass as described above while stirring. A precipitate produced was separated by filtering and then washed with the diisopropyl ether/methanol mixed solution (mass ratio diisopropyl ether:methanol=4:1) of the same mass as described above, whereby a white precipitate was obtained. The above precipitate was dried at 50° C. for 10 hours under reduced pressure (26.7 Pa) to obtain 9.54 g of a polymer (b) comprising a repetitive unit shown below. The polymer (b) thus obtained had Mw of 14800 and a dispersion degree of 1.74.

polymer (b)

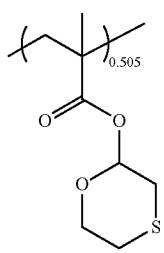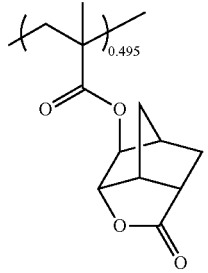

Example 27

Production of Polymer (c)

The polymerization reaction was carried out in the same charged amounts on the same conditions as in Example 26, except that in Example 26, 7.27 g (42.7 mmol) of α-methacryloyloxy-γ-butyrolactone was used in place of 9.49 g (42.7 mmol) of 5-methacryloyloxy-2,6-norbornanecarbolactone and that a use amount of 2,2'-azobis(2,4-dimethylvaleronitrile) was changed from 2.86 g (11.5 mmol) to 1.99 g (8.00 mmol).

A reaction mixture obtained was dropwise added to a diisopropyl ether/methanol mixed solution (mass ratio diisopropyl ether:methanol=4:1) of about 20 times mass based on the reaction mixture at room temperature while stirring, and a precipitate produced was separated by filtering. The above precipitate was dissolved in 80.0 g of 1,4-dioxane, and the solution prepared was dropwise added to the diisopropyl ether/methanol mixed solution (mass ratio diisopropyl ether:methanol=4:1) of the same mass as described above while stirring. A precipitate produced was separated by filtering and then washed with the diisopropyl ether/methanol mixed solution (mass ratio 4/1) of the same mass as described above, whereby a white precipitate was obtained. The above precipitate was dried at 50° C. for 10 hours under reduced pressure (26.7 Pa) to obtain 8.03 g of a polymer (c) comprising a repetitive unit shown below. The polymer (c) thus obtained had Mw of 11800 and a dispersion degree of 1.82.

polymer (c)

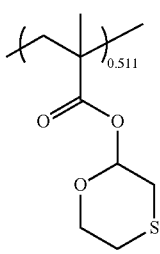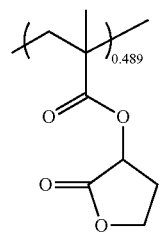

Example 28

Production of Polymer (d)

A round-bottom flask having a content volume of 100 mL equipped with an electromagnetic stirring device, a reflux condenser and a thermometer was charged with 3.58 g (18.7 mmol) of 1,4-oxathiane-2-yl=methacrylate, 2.95 g (12.5 mmol) of 3-hydroxy-1-adamantyl=methacrylate, 4.16 g (18.7 mmol) of 5-methacryloyloxy-2,6-norbornanecarbolactone, 100.0 g of 1,4-dioxane and 1.79 g (7.20 mmol) of 2,2'-azobis(2,4-dimethylvaleronitrile) under nitrogen atmosphere to carry out polymerization reaction at 60 to 63° C. for 4 hours.

A reaction mixture obtained was dropwise added to methanol of about 20 times mass based on the reaction mixture at room temperature while stirring, and a precipitate produced was separated by filtering. The above precipitate was dissolved in 80.0 g of 1,4-dioxane, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 6.31 g of a polymer (d) comprising a repetitive unit shown below. The polymer (d) thus obtained had Mw of 10500 and a dispersion degree of 1.50.

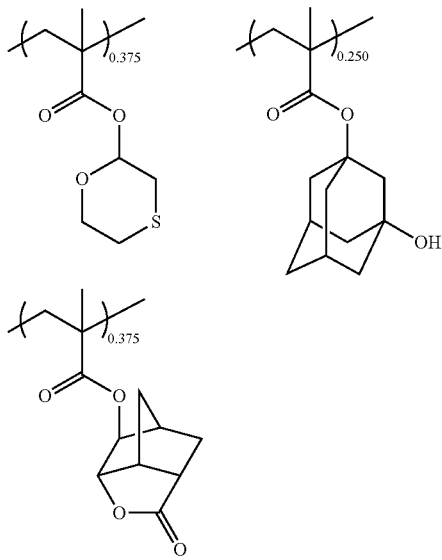

polymer (d)

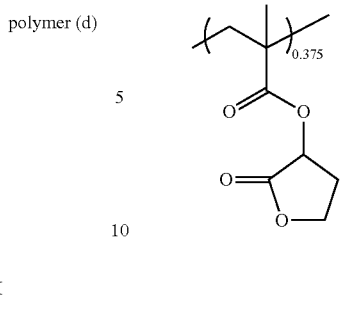

Example 30

Production of Polymer (f)

A round-bottom flask having a content volume of 100 mL equipped with an electromagnetic stirring device, a reflux condenser and a thermometer was charged with 1.70 g (9.78 mmol) of 1,4-dioxane-2-yl=methacrylate obtained in Example 4, 2.31 g (9.78 mmol) of 3-hydroxy-1-adamantyl=methacrylate, 42.0 g of 1,4-dioxane and 0.49 g (1.97 mmol) of 2,2'-azobis(2,4-dimethylvaleronitrile) under nitrogen atmosphere to carry out polymerization reaction at 60 to 65° C. for 6 hours.

A reaction mixture obtained was dropwise added to diisopropyl ether of about 20 times mass based on the reaction mixture at room temperature while stirring, and a precipitate produced was obtained by filtering. The above precipitate was dissolved in 35.0 g of THF, and the solution prepared was dropwise added to a diisopropyl ether/methanol mixed solution (mass ratio diisopropyl ether:methanol=4:1) of the same mass as described above while stirring. A precipitate produced was separated by filtering and then washed with the diisopropyl ether/methanol mixed solution (mass ratio diisopropyl ether:methanol=4:1) of the same mass as described above, whereby a white precipitate was obtained. The above precipitate was dried at 50° C. for 10 hours under reduced pressure (26.7 Pa) to obtain 2.38 g of a polymer (f) comprising a repetitive unit shown below. The polymer (f) thus obtained had Mw of 10400 and a dispersion degree of 1.90.

Example 29

Production of Polymer (e)

The polymerization reaction was carried out in the same charge amounts on the same conditions as in Example 28, except that in Example 28, 3.18 g (18.7 mmol) of α-methacryloyloxy-γ-butyrolactone was used in place of 4.16 g (18.7 mmol) of 5-methacryloyloxy-2,6-norbornanecarbolactone.

A reaction mixture obtained was dropwise added to methanol of about 20 times mass based on the reaction mixture at room temperature while stirring, and a precipitate produced was separated by filtering. The above precipitate was dissolved in 80.0 g of 1,4-dioxane, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 5.34 g of a polymer (e) comprising a repetitive unit shown below. The polymer (e) thus obtained had Mw of 12300 and a dispersion degree of 1.62.

polymer (f)

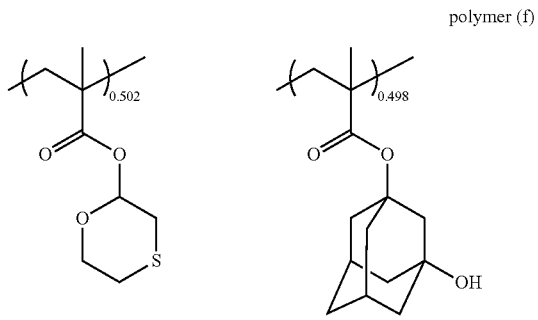

Example 31

Production of Polymer (g)

The polymerization reaction was carried out in the same charge amounts on the same conditions as in Example 30, except that in Example 30, 2.17 g (9.78 mmol) of 5-methacryloyloxy-2,6-norbornanecarbolactone was used in place of 2.31 g (9.78 mmol) of 3-hydroxy-1-adamantyl=methacrylate.

polymer (e)

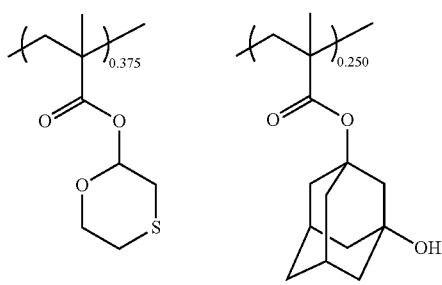

A reaction mixture obtained was dropwise added to diisopropyl ether of about 20 times mass based on the reaction mixture at room temperature while stirring, and a precipitate produced was separated by filtering. The above precipitate was dissolved in 35.0 g of 1,4-dioxane, and the solution prepared was dropwise added to a diisopropyl ether/methanol mixed solution (mass ratio diisopropyl ether:methanol=4:1) of the same mass as described above while stirring. A precipitate produced was separated by filtering and then washed with the diisopropyl ether/methanol mixed solution (mass ratio diisopropyl ether:methanol=4:1) of the same mass as described above, whereby a white precipitate was obtained. The above precipitate was dried at 50° C. for 10 hours under reduced pressure (26.7 Pa) to obtain 2.40 g of a polymer (g) comprising a repetitive unit shown below. The polymer (g) thus obtained had Mw of 16200 and a dispersion degree of 1.70.

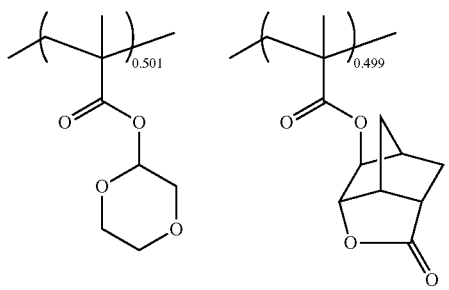

polymer (g)

Example 32

Production of Polymer (h)

The polymerization reaction was carried out in the same charge amounts on the same conditions as in Example 30, except that in Example 30, 1.66 g (9.78 mmol) of α-methacryloyloxy-γ-butyrolactone was used in place of 2.31 g (9.78 mmol) of 3-hydroxy-1-adamantyl=methacrylate.

A reaction mixture obtained was dropwise added to diisopropyl ether of about 20 times mass based on the reaction mixture at room temperature while stirring, and a precipitate produced was separated by filtering. The above precipitate was dissolved in 35.0 g of 1,4-dioxane, and the solution prepared was dropwise added to a diisopropyl ether/methanol mixed solution (mass ratio diisopropyl ether:methanol=4:1) of the same mass as described above while stirring. A precipitate produced was separated by filtering and then washed with the diisopropyl ether/methanol mixed solution (mass ratio diisopropyl ether:methanol=4:1) of the same mass as described above, whereby a white precipitate was obtained. The above precipitate was dried at 50° C. for 10 hours under reduced pressure (26.7 Pa) to obtain 2.02 g of a polymer (h) comprising a repetitive unit shown below. The polymer (h) thus obtained had Mw of 12000 and a dispersion degree of 1.59.

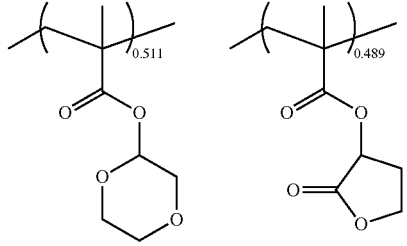

polymer (h)

Example 33

Production of Polymer (i)

A round-bottom flask having a content volume of 100 mL equipped with an electromagnetic stirring device, a reflux condenser and a thermometer was charged with 1.62 g (9.35 mmol) of 1,4-dioxane-2-yl=methacrylate, 1.48 g (6.25 mmol) of 3-hydroxy-1-adamantyl=methacrylate, 2.08 g (9.35 mmol) of 5-methacryloyloxy-2,6-norbornanecarbolactone, 50.0 g of 1,4-dioxane and 0.90 g (3.60 mmol) of 2,2'-azobis(2,4-dimethylvaleronitrile) under nitrogen atmosphere to carry out polymerization reaction at 60 to 63° C. for 6 hours.

A reaction mixture obtained was dropwise added to methanol of about 20 times mass based on the reaction mixture at room temperature while stirring, and a precipitate produced was separated by filtering. The above precipitate was dissolved in 40.0 g of 1,4-dioxane, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 3.22 g of a polymer (i) comprising a repetitive unit shown below. The polymer (i) thus obtained had Mw of 13800 and a dispersion degree of 1.61.

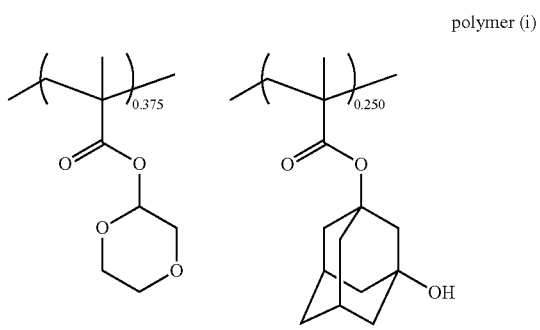

polymer (i)

-continued

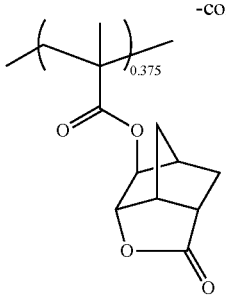

Example 34

Production of Polymer (j)

The polymerization reaction was carried out in the same charge amounts on the same conditions as in Example 33, except that in Example 33, 1.59 g (9.35 mmol) of α-methacryloyloxy-γ-butyrolactone was used in place of 2.08 g (9.35 mmol) of 5-methacryloyloxy-2,6-norbornanecarbolactone.

A reaction mixture obtained was dropwise added to methanol of about 20 times mass based on the reaction mixture at room temperature while stirring, and a precipitate produced was separated by filtering. The above precipitate was dissolved in 40.0 g of 1,4-dioxane, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 2.65 g of a polymer (j) comprising a repetitive unit shown below. The polymer (j) thus obtained had Mw of 15500 and a dispersion degree of 1.43.

polymer (j)

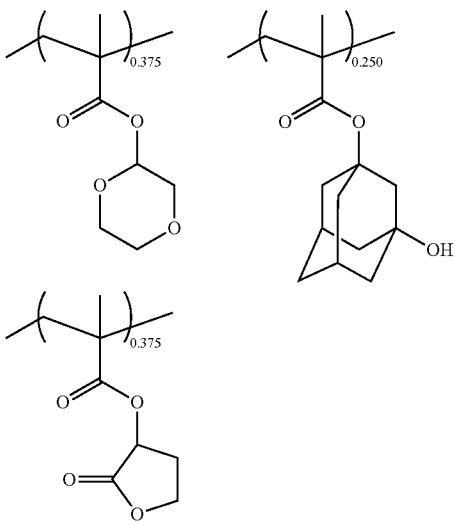

Example 35

Production of Polymer (k)

The polymerization reaction was carried out in the same charge amounts on the same conditions as in Example 30, except that in Example 30, 2.01 g (9.78 mmol) of 1,4-oxathiepane-2-yl=methacrylate obtained in Example 6 was used in place of 1.70 g (9.78 mmol) of 1,4-dioxane-2-yl=methacrylate.

A reaction mixture obtained was dropwise added to diisopropyl ether of about 20 times mass based on the reaction mixture at room temperature while stirring, and a precipitate produced was obtained by filtering. The above precipitate was dissolved in 35.0 g of THF, and the solution prepared was dropwise added to a diisopropyl ether/methanol mixed solution (mass ratio diisopropyl ether:methanol=4:1) of the same mass as described above while stirring. A precipitate produced was separated by filtering and then washed with the diisopropyl ether/methanol mixed solution (mass ratio diisopropyl ether:methanol=4:1) of the same mass as described above, whereby a white precipitate was obtained. The above precipitate was dried at 50° C. for 10 hours under reduced pressure (26.7 Pa) to obtain 2.38 g of a polymer (k) comprising a repetitive unit shown below. The polymer (k) thus obtained had Mw of 16800 and a dispersion degree of 1.68.

polymer (k)

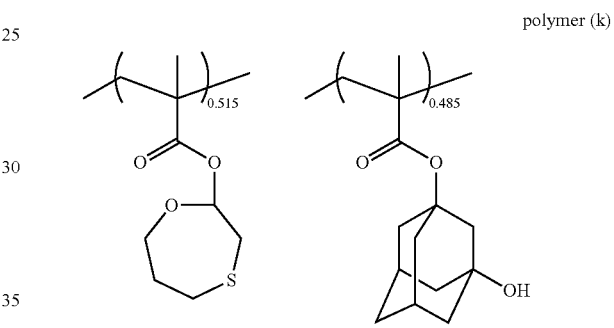

Example 36

Production of Polymer (l)

The polymerization reaction was carried out in the same charge amounts on the same conditions as in Example 33, except that in Example 33, 1.93 g (9.35 mmol) of 1,4-oxathiepane-2-yl=methacrylate obtained in Example 6 was used in place of 1.62 g (9.35 mmol) of 1,4-dioxane-2-yl=methacrylate and that 1.59 g (9.35 mmol) of α-methacryloyloxy-γ-butyrolactone was used in place of 2.08 g (9.35 mmol) of 5-methacryloyloxy-2,6-norbornanecarbolactone.

A reaction mixture obtained was dropwise added to methanol of about 20 times mass based on the reaction mixture at room temperature while stirring, and a precipitate produced was separated by filtering. The above precipitate was dissolved in 40.0 g of 1,4-dioxane, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 3.00 g of a polymer (l) comprising a repetitive unit shown below. The polymer (l) thus obtained had Mw of 16900 and a dispersion degree of 1.64.

polymer (l)

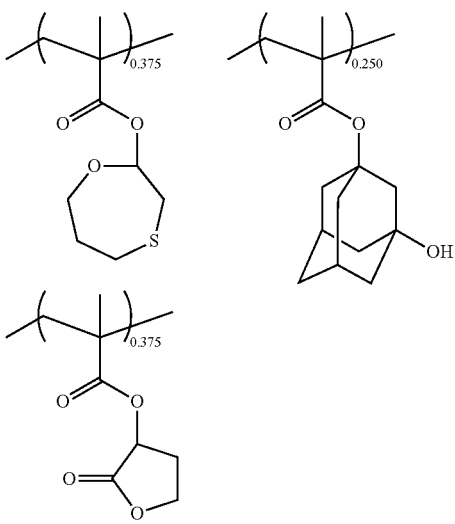

Example 37

Production of Polymer (m)

The polymerization reaction was carried out in the same charge amounts on the same conditions as in Example 30, except that in Example 30, 1.84 g (9.78 mmol) of 1,4-dioxepane-2-yl=methacrylate obtained in Example 8 was used in place of 1.70 g (9.78 mmol) of 1,4-dioxane-2-yl=methacrylate.

A reaction mixture obtained was dropwise added to diisopropyl ether of about 20 times mass based on the reaction mixture at room temperature while stirring, and a precipitate produced was obtained by filtering. The above precipitate was dissolved in 35.0 g of THF, and the solution prepared was dropwise added to a diisopropyl ether/methanol mixed solution (mass ratio diisopropyl ether:methanol=4:1) of the same mass as described above while stirring. A precipitate produced was separated by filtering and then washed with the diisopropyl ether/methanol mixed solution (mass ratio diisopropyl ether:methanol=4:1) of the same mass as described above, whereby a white precipitate was obtained. The above precipitate was dried at 50° C. for 10 hours under reduced pressure (26.7 Pa) to obtain 2.20 g of a polymer (m) comprising a repetitive unit shown below. The polymer (m) thus obtained had Mw of 18700 and a dispersion degree of 1.80.

polymer (m)

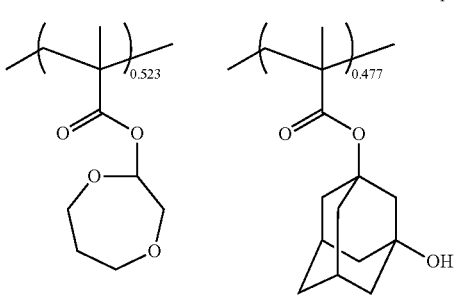

Example 38

Production of Polymer (n)

The polymerization reaction was carried out in the same charge amounts on the same conditions as in Example 33, except that in Example 33, 1.76 g (9.35 mmol) of 1,4-dioxepane-2-yl=methacrylate obtained in Example 8 was used in place of 1.62 g (9.35 mmol) of 1,4-dioxane-2-yl=methacrylate and that 1.59 g (9.35 mmol) of α-methacryloyloxy-γ-butyrolactone was used in place of 2.08 g (9.35 mmol) of 5-methacryloyloxy-2,6-norbornanecarbolactone.

A reaction mixture obtained was dropwise added to methanol of about 20 times mass based on the reaction mixture at room temperature while stirring, and a precipitate produced was separated by filtering. The above precipitate was dissolved in 40.0 g of 1,4-dioxane, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 2.89 g of a polymer (n) comprising a repetitive unit shown below. The polymer (n) thus obtained had Mw of 13800 and a dispersion degree of 1.55.

polymer (n)

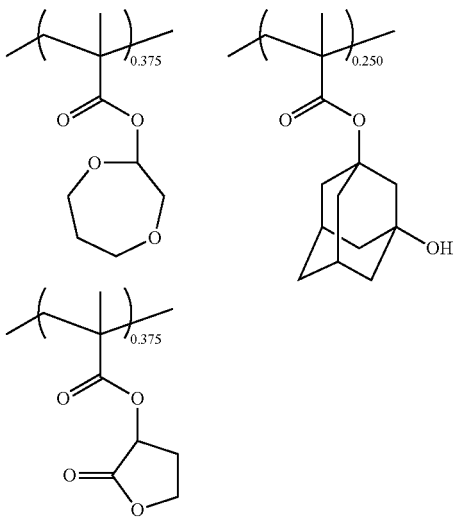

Example 39

Production of Polymer (o)

The polymerization reaction was carried out in the same charge amounts on the same conditions as in Example 30, except that in Example 30, 2.02 g (9.78 mmol) of 6-methyl-1,4-oxathiane-2-yl=methacrylate obtained in Example 10 was used in place of 1.70 g (9.78 mmol) of 1,4-dioxane-2-yl=methacrylate.

A reaction mixture obtained was dropwise added to diisopropyl ether of about 20 times mass based on the reaction mixture at room temperature while stirring, and a precipitate produced was obtained by filtering. The above precipitate was dissolved in 35.0 g of THF, and the solution prepared was dropwise added to a diisopropyl ether/methanol mixed solution (mass ratio diisopropyl ether:methanol=4:1) of the same mass as described above while stirring. A precipitate produced was separated by filtering and then washed with the diisopropyl ether/methanol mixed solution (mass ratio diisopropyl ether:methanol=4:1) of the same mass as described above, whereby a white precipitate was obtained. The above precipitate was dried at 50° C. for 10 hours under reduced pressure (26.7 Pa) to obtain 2.39 g of a polymer (o) comprising a repetitive unit shown below. The polymer (o) thus obtained had Mw of 17200 and a dispersion degree of 1.65.

polymer (o)

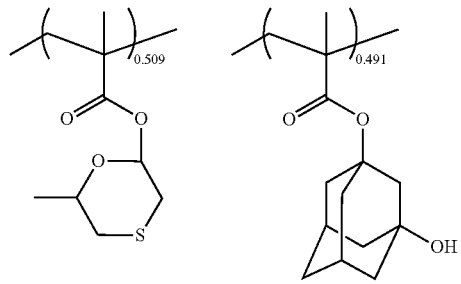

Example 40

Production of Polymer (p)

The polymerization reaction was carried out in the same charge amounts on the same conditions as in Example 33, except that in Example 33, 1.93 g (9.35 mmol) of 6-methyl-1,4-oxathiane-2-yl=methacrylate obtained in Example 10 was used in place of 1.62 g (9.35 mmol) of 1,4-dioxane-2-yl=methacrylate and that 1.59 g (9.35 mmol) of α-methacryloyloxy-γ-butyrolactone was used in place of 2.08 g (9.35 mmol) of 5-methacryloyloxy-2,6-norbornanecarbolactone.

A reaction mixture obtained was dropwise added to methanol of about 20 times mass based on the reaction mixture at room temperature while stirring, and a precipitate produced was separated by filtering. The above precipitate was dissolved in 40.0 g of 1,4-dioxane, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 3.11 g of a polymer (p) comprising a repetitive unit shown below. The polymer (p) thus obtained had Mw of 15800 and a dispersion degree of 1.71.

polymer (p)

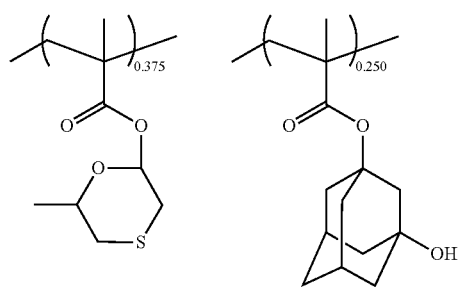

-continued

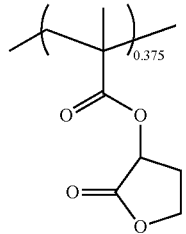

Example 41

Production of Polymer (q)

The polymerization reaction was carried out in the same charge amounts on the same conditions as in Example 30, except that in Example 30, 2.00 g (9.78 mmol) of 5,6-dimethyl-1,4-dioxane-2-yl=methacrylate obtained in Example 12 was used in place of 1.70 g (9.78 mmol) of 1,4-dioxane-2-yl=methacrylate.

A reaction mixture obtained was dropwise added to diisopropyl ether of about 20 times mass based on the reaction mixture at room temperature while stirring, and a precipitate produced was obtained by filtering. The above precipitate was dissolved in 35.0 g of THF, and the solution prepared was dropwise added to a diisopropyl ether/methanol mixed solution (mass ratio diisopropyl ether:methanol=4:1) of the same mass as described above while stirring. A precipitate produced was separated by filtering and then washed with the diisopropyl ether/methanol mixed solution (mass ratio diisopropyl ether:methanol=4:1) of the same mass as described above, whereby a white precipitate was obtained. The above precipitate was dried at 50° C. for 10 hours under reduced pressure (26.7 Pa) to obtain 2.63 g of a polymer (q) comprising a repetitive unit shown below. The polymer (q) thus obtained had Mw of 16900 and a dispersion degree of 1.54.

polymer (q)

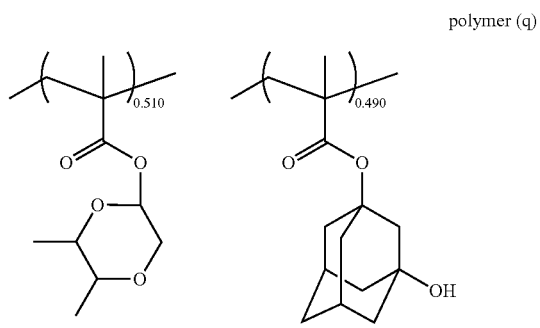

Example 42

Production of Polymer (r)

The polymerization reaction was carried out in the same charge amounts on the same conditions as in Example 33, except that in Example 33, 1.91 g (9.35 mmol) of 5,6-dimethyl-1,4-dioxane-2-yl=methacrylate obtained in Example 12 was used in place of 1.62 g (9.35 mmol) of 1,4-dioxane-2-yl=methacrylate and that 1.59 g (9.35 mmol) of α-methacryloyloxy-γ-butyrolactone was used in place of 2.08 g (9.35 mmol) of 5-methacryloyloxy-2,6-norbornanecarbolactone.

A reaction mixture obtained was dropwise added to methanol of about 20 times mass based on the reaction mixture at room temperature while stirring, and a precipitate produced was separated by filtering. The above precipitate was dissolved in 40.0 g of 1,4-dioxane, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 2.93 g of a polymer (r) comprising a repetitive unit shown below. The polymer (r) thus obtained had Mw of 14800 and a dispersion degree of 1.63.

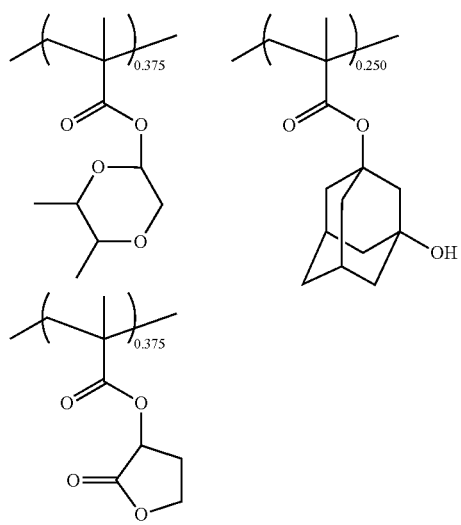

Comparative Synthetic Example 1

Production of Polymer (A)

A round-bottom flask having a content volume of 200 mL equipped with an electromagnetic stirring device, a reflux condenser and a thermometer was charged with 10.0 g (42.3 mmol) of 2-methyl-2-adamantyl=methacrylate, 10.0 g (42.7 mmol) of 3-hydroxy-1-adamantyl=methacrylate, 80.0 g of propylene glycol monomethyl ether and 1.40 g (8.53 mmol) of 2,2'-azobisisobutyronitrile under nitrogen atmosphere to carry out polymerization reaction at 81 to 87° C. for 2 hours.

A reaction mixture obtained was dropwise added to methanol of about 20 times mass based on the reaction mixture at room temperature while stirring, and a precipitate produced was separated by filtering. The above precipitate was dissolved in 100.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 13.2 g of a polymer (A) comprising a repetitive unit shown below. The polymer (A) thus obtained had Mw of 16100 and a dispersion degree of 1.68.

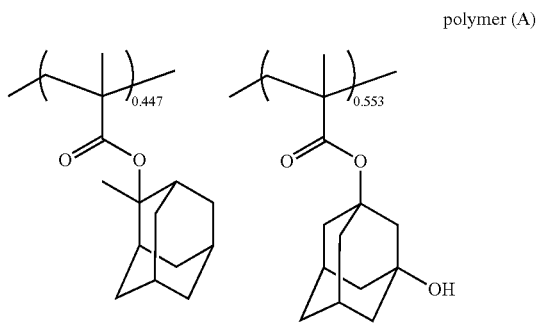

Comparative Synthetic Example 2

Production of Polymer (B)

The polymerization reaction was carried out in the same charge amounts on the same conditions as in Comparative Synthetic Example 1, except that in Comparative Synthetic Example 1, 7.39 g (42.7 mmol) of tetrahydropyran-2-yl=methacrylate was used in place of 10.0 g (42.3 mmol) of 2-methyl-2-adamantyl=methacrylate.

A reaction mixture obtained was dropwise added to methanol of about 20 times mass based on the reaction mixture at room temperature while stirring, and a precipitate produced was separated by filtering. The above precipitate was dissolved in 100.0 g of THF, and the solution prepared was dropwise added to methanol of the same mass as described above while stirring. A precipitate produced was separated by filtering and then washed with methanol of the same mass as described above, whereby a white precipitate was obtained. The above precipitate was dried at 50° C. for 10 hours under reduced pressure (26.7 Pa) to obtain 9.96 g of a polymer (B) comprising a repetitive unit shown below. The polymer (B) thus obtained had Mw of 13200 and a dispersion degree of 1.71.

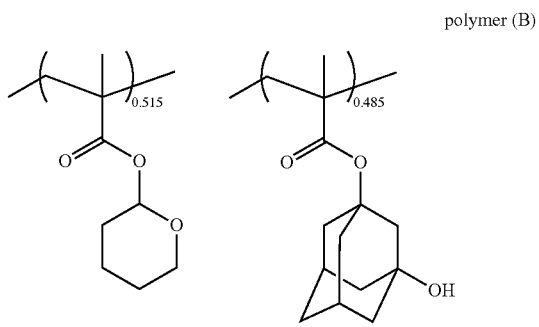

Comparative Synthetic Example 3

Production of Polymer (C)

A round-bottom flask having a content volume of 200 mL equipped with an electromagnetic stirring device, a reflux condenser and a thermometer was charged with 9.14 g (50.2 mmol) of 1-methyl-1-cyclohexyl=methacrylate, 11.82 g (50.0 mmol) of 3-hydroxy-1-adamantyl=methacrylate, 101.4 g of 1,4-dioxane and 1.24 g (7.55 mmol) of 2,2'-azobisisobutyronitrile under nitrogen atmosphere to carry out polymerization reaction at 80 to 82° C. for 5 hours.

A reaction mixture obtained was dropwise added to a water-methanol mixed solution (mass ratio water:methanol=1:3) of about 20 times mass based on the reaction mixture at room temperature while stirring, and a precipitate produced was separated by filtering. The above precipitate was dissolved in 140.0 g of THF, and the solution prepared was dropwise added to the water-methanol mixed solution (mass ratio water:methanol=1:3) of the same mass as described above while stirring. A precipitate produced was separated by filtering and then washed with the water-methanol mixed solution (mass ratio water:methanol=1:3) of the same mass as described above, whereby a white precipitate was obtained. The above precipitate was dried at 50° C. for 10 hours under reduced pressure (26.7 Pa) to obtain 11.8 g of a polymer (C) comprising a repetitive unit shown below. The polymer (C) thus obtained had Mw of 12600 and a dispersion degree of 1.83.

polymer (C)

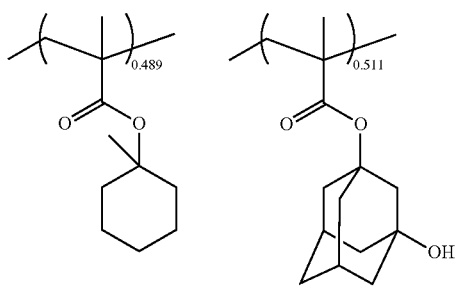

Comparative Synthetic Example 4

Production of Polymer (D)

A round-bottom flask having a content volume of 100 mL equipped with an electromagnetic stirring device, a reflux condenser and a thermometer was charged with 4.39 g (18.7 mmol) of 2-methacryloyloxy-2-methyladamantane, 2.95 g (12.5 mmol) of 3-hydroxy-1-adamantyl=methacrylate, 3.18 g (18.7 mmol) of α-methacryloyloxy-γ-butyrolactone, 35.4 g of methyl ethyl ketone and 0.66 g (4.0 mmol) of 2,2'-azobisisobutyronitrile under nitrogen atmosphere to carry out polymerization reaction at 80° C. for 4 hours.

A reaction mixture obtained was dropwise added to methanol of about 20 times mass at room temperature while stirring, whereby a white precipitate was obtained. The above precipitate was separated by filtering and dried at 50° C. for 10 hours under reduced pressure (26.7 Pa) to obtain 6.06 g of a polymer (D) comprising a repetitive unit shown below. The polymer (D) thus obtained had Mw of 10000 and a dispersion degree of 1.50.

polymer (D)

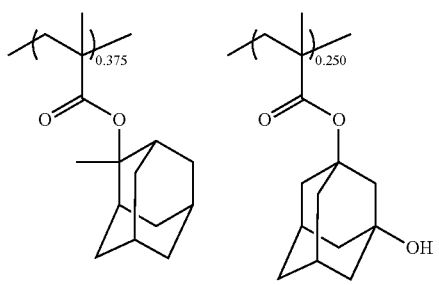

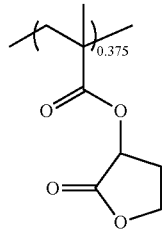

Comparative Synthetic Example 5

Production of Polymer (E)

The polymerization reaction was carried out in the same charge amounts on the same conditions as in Comparative Synthetic Example 4, except that in Comparative Synthetic Example 4, 3.18 g (18.7 mmol) of tetrahydropyran-2-yl=methacrylate was used in place of 4.39 g (18.7 mmol) of 2-methacryloyloxy-2-methyladamantane.

A reaction mixture obtained was dropwise added to methanol of about 20 times mass at room temperature while stirring, whereby a white precipitate was obtained. The above precipitate was separated by filtering and dried at 50° C. for 10 hours under reduced pressure (26.7 Pa) to obtain 5.82 g of a polymer (E) comprising a repetitive unit shown below. The polymer (E) thus obtained had Mw of 6500 and a dispersion degree of 1.60.

polymer (E)

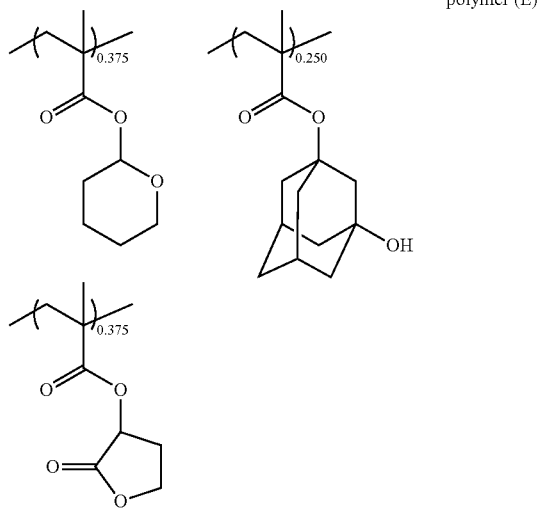

Comparative Synthetic Example 6

Production of Polymer (F)

The polymerization reaction was carried out in the same charge amounts on the same conditions as in Comparative Synthetic Example 4, except that in Comparative Synthetic Example 4, 3.41 g (18.7 mmol) of 1-methyl-1- cyclohexyl=methacrylate was used in place of 4.39 g (18.7 mmol) of 2-methacryloyloxy-2-methyladamantane.

A reaction mixture obtained was dropwise added to methanol of about 20 times mass at room temperature while stirring, whereby a white precipitate was obtained. The above precipitate was separated by filtering and dried at 50° C. for 10 hours under reduced pressure (26.7 Pa) to obtain 5.69 g of a polymer (F) comprising a repetitive unit shown below. The polymer (F) thus obtained had Mw of 6900 and a dispersion degree of 1.58.

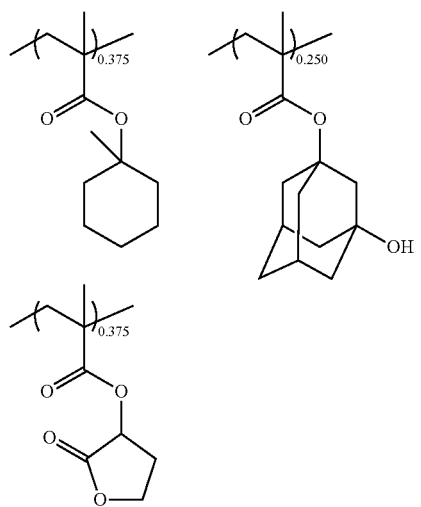

polymer (F)

Comparative Synthetic Example 7

Production of Polymer (G)

The polymerization reaction was carried out in the same charge amounts on the same conditions as in Comparative Synthetic Example 1, except that in Comparative Synthetic Example 1, 7.59 g (42.7 mmol) of 5-methacryloyloxy-1,3-dioxan was used in place of 10.0 g (42.3 mmol) of 2-methyl-2-adamantyl=methacrylate.

A reaction mixture obtained was dropwise added to diisopropyl ether of about 20 times mass based on the reaction mixture at room temperature while stirring, and a precipitate produced was separated by filtering. The above precipitate was dissolved in 100.0 g of 1,4-dioxane, and the solution prepared was dropwise added to a diisopropyl ether/methanol mixed solution (mass ratio diisopropyl ether:methanol=4:1) of the same mass as described above while stirring. A precipitate produced was separated by filtering and then washed with the diisopropyl ether/methanol mixed solution (mass ratio diisopropyl ether:methanol=4:1) of the same mass as described above, whereby a white precipitate was obtained. The above precipitate was dried at 50° C. for 10 hours under reduced pressure (26.7 Pa) to obtain 9.01 g of a polymer (G) comprising a repetitive unit shown below. The polymer (G) thus obtained had Mw of 16700 and a dispersion degree of 1.71.

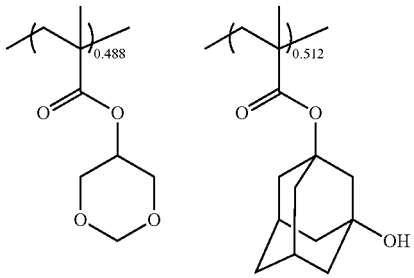

polymer (G)

Comparative Synthetic Example 8

Production of Polymer (H)

The polymerization reaction was carried out in the same charge amounts on the same conditions as in Comparative Synthetic Example 4, except that in Comparative Synthetic Example 4, 3.32 g (18.7 mmol) of 5-methacryloyloxy-1,3-dioxane was used in place of 4.39 g (18.7 mmol) of 2-methacryloyloxy-2-methyladamantane.

A reaction mixture obtained was dropwise added to methanol of about 20 times mass at room temperature while stirring, whereby a white precipitate was obtained. The above precipitate was separated by filtering and dried at 50° C. for 10 hours under reduced pressure (26.7 Pa) to obtain 6.02 g of a polymer (H) comprising a repetitive unit shown below. The polymer (H) thus obtained had Mw of 12200 and a dispersion degree of 1.55.

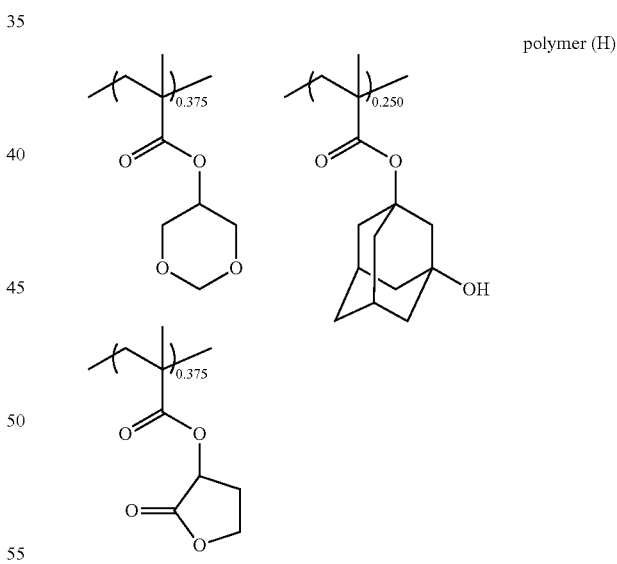

polymer (H)

Examples 43 to 60 and Comparative Examples 1 to 8

Evaluation of Dissolution Characteristics in Developer by QCM Method

Used were 100 parts by mass of the polymers obtained in Examples 25 to 42 or Comparative Synthetic Examples 1 to 8, 3 parts by mass of TPS-109 (trade name, component: triphenylsulfonium nonafluoro-n-butanesulfonate, manufactured by Midori Kagaku Co., Ltd.) as a photoacid generator and as solvents, ethyl lactate when the polymers (a), (b), (c), (f), (g), (h), (k), (m), (o), (q), (A), (B), (C) and (G) were used and a mixed solvent of propylene glycol monomethyl ether acetate/ethyl lactate=1/1 (volume ratio) when the polymers other than the above polymers were used, and the respective components were mixed to prepare photoresist compositions in which a concentration of the polymer was 12% by mass.

The respective photoresist compositions thus obtained were filtrated through a filter (made of a tetrafluoroethylene resin (PTFE), pore diameter: 0.2 μm), and then they were coated respectively by a spin coating method on a quartz substrate of a 1 inch size in which a gold electrode was vacuum-deposited on a surface to form a photosensitive layer having a thickness of 300 nm. The quartz substrate having a photosensitive layer formed thereon was pre-baked at 110° C. for 90 seconds on a hot plate and then exposed at an exposure dose of 100 mJ/cm$^2$ with an ArF excimer laser (wavelength: 193 nm), and subsequently it was subjected to post-exposure baking at 110° C. for 90 seconds.

The quartz substrate described above was set in a quartz oscillator microbalance equipment "RQCM" (trade name; manufactured by Maxtek Corp.) and subjected to developing treatment by a tetramethylammonium hydroxide aqueous solution of 2.38% by mass for 120 seconds. A change in an oscillation frequency of the quartz substrate during the developing treatment was monitored with the passage of time, and then a change in the oscillation frequency was reduced to a change in the film thickness to calculate the maximum swelling amount from a change in an increase of the film thickness and calculate the dissolution rate from a change in a decrease of the film thickness. The results thereof are shown in Table 3.

TABLE 3

| evaluation of dissolution characteristics in developer by QCM method | | | |
|---|---|---|---|
| | Polymer in photoresist composition | Dissolution rate in developing (nm/second) | Maximum swelling amount (nm) |
| Example 43 | (a) | 1300 | 10 |
| Example 44 | (b) | 1340 | 8 |
| Example 45 | (c) | 1380 | 8 |
| Example 46 | (d) | 1210 | 12 |
| Example 47 | (e) | 1280 | 10 |
| Example 48 | (f) | 1300 | 9 |
| Example 49 | (g) | 1360 | 12 |
| Example 50 | (h) | 1420 | 8 |
| Example 51 | (i) | 1290 | 9 |
| Example 52 | (j) | 1390 | 10 |
| Example 53 | (k) | 1290 | 9 |
| Example 54 | (l) | 1330 | 9 |
| Example 55 | (m) | 1310 | 10 |
| Example 56 | (n) | 1350 | 10 |
| Example 57 | (o) | 1290 | 9 |
| Example 58 | (p) | 1210 | 9 |
| Example 59 | (q) | 1200 | 10 |
| Example 60 | (r) | 1300 | 10 |
| Comparative Example 1 | (A) | 950 | 100 |
| Comparative Example 2 | (B) | 1200 | 10 |
| Comparative Example 3 | (C) | 500 | 20 |
| Comparative Example 4 | (D) | 600 | 40 |
| Comparative Example 5 | (E) | 1100 | 10 |
| Comparative Example 6 | (F) | 530 | 19 |
| Comparative Example 7 | (G) | 90 | 150 |
| Comparative Example 8 | (H) | 120 | 210 |

Examples 61 to 78 and Comparative Examples 9 to 16

Evaluation of Exposure by Two-Beam Interference Method

Used were 100 parts by mass of the polymers obtained in Examples 25 to 42 or Comparative Synthetic Examples 1 to 8, 3 parts by mass of TPS-109 (trade name, component: triphenylsulfonium nonafluoro-n-butanesulfonate, manufactured by Midori Kagaku Co., Ltd.) as a photoacid generator and as solvents, ethyl lactate when the polymers (a), (b), (c), (f), (g), (h), (k), (m), (o), (q), (A), (B), (C) and (G) were used and a mixed solvent of propylene glycol monomethyl ether acetate/ethyl lactate=1/1 (volume ratio) when the polymers other than above polymers were used, and the respective components were mixed to prepare photoresist compositions in which a concentration of the polymer was 12% by mass.

The respective photoresist compositions thus obtained were filtrated through a filter (made of a tetrafluoroethylene resin (PTFE), pore diameter: 0.2 μm). A propylene glycol monomethyl ether acetate solution of a cresol novolac resin (PS-6937, manufactured by Gunei Chemical Industry Co., Ltd.) having a concentration of 6% by mass was coated on a silicon wafer having a diameter of 10 cm by a spin coating method and baked at 200° C. for 90 seconds on a hot plate to thereby form a anti-reflective coat (undercoat film), and the above filtrates were coated respectively on the above silicon wafer by a spin coating method and pre-baked at 130° C. for 90 seconds on a hot plate to thereby form a resist film having a film thickness of about 300 nm.

The above resist film was exposed with an ArF excimer laser having a wavelength of 193 nm by a two-beam interference method. Subsequently, it was subjected to post-exposure baking at 130° C. for 90 seconds and then to developing treatment for 60 seconds by a 2.38 mass % tetramethylammonium hydroxide aqueous solution to thereby form a line and space pattern of 1:1. A piece obtained by cutting the wafer subjected to the development was observed under a scanning electron microscope (SEM) to observe a form of the pattern in an exposure dose in which the line and space having a line width of 100 nm was subjected to resolution by 1:1 and measure a change in the line width (hereinafter referred to as LWR). The line width was detected in plural positions in a measuring monitor, and dispersion (3σ) in variation of the detected positions was set to an index for LWR. The results thereof are shown in Table 4.

TABLE 4 evaluation of exposure by two-beam interference method

| | Polymer in photoresist composition | LWR (nm) | Pattern form |
|---|---|---|---|
| Example 61 | (a) | 7.5 | Good |
| Example 62 | (b) | 7.2 | Good |
| Example 63 | (c) | 7.1 | Good |
| Example 64 | (d) | 7.6 | Good |
| Example 65 | (e) | 7.1 | Good |
| Example 66 | (f) | 7.7 | Good |
| Example 67 | (g) | 7.6 | Good |
| Example 68 | (h) | 7.1 | Good |
| Example 69 | (i) | 7.9 | Good |
| Example 70 | (j) | 7.9 | Good |
| Example 71 | (k) | 7.9 | Good |
| Example 72 | (l) | 8.1 | Good |
| Example 73 | (m) | 7.2 | Good |
| Example 74 | (n) | 7.6 | Good |
| Example 75 | (o) | 7.5 | Good |
| Example 76 | (p) | 7.4 | Good |
| Example 77 | (q) | 7.9 | Good |
| Example 78 | (r) | 7.8 | Good |
| Comparative Example 9 | (A) | 13.4 | Good |
| Comparative Example 10 | (B) | 8.1 | Good |
| Comparative Example 11 | (C) | 10.1 | Good |
| Comparative Example 12 | (D) | 12.3 | Good |
| Comparative Example 13 | (E) | 8.5 | Good |
| Comparative Example 14 | (F) | 9.3 | Good |
| Comparative Example 15 | (G) | Unable to form pattern | — |
| Comparative Example 16 | (H) | Unable to form pattern | — |

Examples 79 to 88 and Comparative Examples 17 to 20

Evaluation of Heat Stability

The heat stabilities of the polymers obtained in Examples 25 to 27, 30 to 32, 35, 37, 39 and 41 and Comparative Synthetic Examples 1 to 3 and 7 were confirmed by means of a micro heat weight measuring equipment "TGA-50" (trade name; manufactured by Shimadzu Corporation). A sample amount of the polymer was set to about 5.0 mg, and the heat stability was measured at a nitrogen gas flow rate of 50 mL/minute and a heating rate of 10° C./minute in a range of 20 to 600° C. The temperature at which a reduction in the weight was initiated and the temperature at which the weight was reduced by 5% based on the original weight were read from a graph obtained. A reduction in the weight shows that the polymer is decomposed by heat, and it can usually be understood that the higher the temperature at which a reduction in the weight is shown is, the more stable to heat the polymer is. The results thereof are shown in Table 5.

TABLE 5 evaluation of heat stability

| | Polymer in photoresist composition | Weight reduction initiating temperature (° C.) | Temperature in 5% weight reduction (° C.) |
|---|---|---|---|
| Example 79 | (a) | 130 | 198 |
| Example 80 | (b) | 140 | 195 |
| Example 81 | (c) | 130 | 202 |
| Example 82 | (f) | 130 | 190 |
| Example 83 | (g) | 130 | 192 |
| Example 84 | (h) | 130 | 190 |
| Example 85 | (k) | 140 | 202 |
| Example 86 | (m) | 130 | 189 |
| Example 87 | (o) | 140 | 210 |
| Example 88 | (q) | 130 | 190 |
| Comparative Example 17 | (A) | 190 | 227 |
| Comparative Example 18 | (B) | 120 | 162 |
| Comparative Example 19 | (C) | 180 | 209 |
| Comparative Example 20 | (G) | 170 | 215 |

It can be found from the results shown in Table 3 to Table 5 that in the case of the polymers (VIII) containing the acrylic ester derivative (I) of the present invention in a constitutional unit, a dissolution rate in an alkali developer used in a developing step when a pattern is formed on the photoresist is very high as compared with the case of the polymers containing no acrylic ester derivative (I) in a constitutional unit and that they have a very small maximum swelling amount in developing (refer to Examples 43 to 60 and Comparative Examples 1 to 8) and are improved in LWR (refer to Examples 61 to 78 and Comparative Examples 9 to 16). Further, they are excellent as well in a heat stability (refer to Examples 79 to 88 and Comparative Examples 17 to 20), and therefore it can be found that they are useful as a chemically amplified resist for producing semiconductor devices.

Industrial Applicability

The polymer (VIII) obtained by polymerizing a raw material containing the acrylic ester derivative (I) obtained in the present invention is useful as a raw material for photoresist compositions.

Further, the cyclic alcohol (II-1) obtained in the present invention is useful as a raw material for the acrylic ester derivative (I).

The invention claimed is:

1. An acrylic ester derivative of Formula (I):

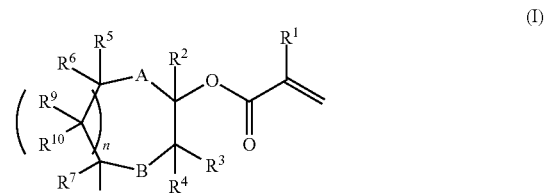

(I)

wherein:
R$^1$ is a hydrogen atom, methyl, or trifluoromethyl;
combination of R$^2$, R$^3$, and R$^4$ is any of:
1) R$^2$, R$^3$, and R$^4$ are each independently a hydrogen atom, a linear alkyl group comprising 1 to 6 carbon atoms, a branched alkyl group comprising 3 to 6 carbon atoms, or a cyclic alkyl group comprising 3 to 6 carbon atoms;

2) $R^2$ and $R^3$ are combined to form an alkylene group comprising 3 to 6 carbon atoms, and $R^4$ is a hydrogen atom, a linear alkyl group comprising 1 to 6 carbon atoms, a branched alkyl group comprising 3 to 6 carbon atoms, or a cyclic alkyl group comprising 3 to 6 carbon atoms; or 3) $R^2$ is a hydrogen atom, a linear alkyl group comprising 1 to 6 carbon atoms, a branched alkyl group comprising 3 to 6 carbon atoms, or a cyclic alkyl group comprising 3 to 6 carbon atoms, and $R^3$ and $R^4$ are combined to form an alkylene group comprising 3 to 6 carbon atoms;

in n, $R^5$, $R^6$, $R^7$, $R^8$, $R^9$, and $R^{10}$:

1) when n is 0, $R^5$ and $R^8$ are each independently a hydrogen atom, a linear alkyl group comprising 1 to 6 carbon atoms, a branched alkyl group comprising 3 to 6 carbon atoms, or a cyclic alkyl group comprising 3 to 6 carbon atoms; $R^6$ and $R^7$ are each independently a hydrogen atom, a linear alkyl group comprising 1 to 6 carbon atoms, a branched alkyl group comprising 3 to 6 carbon atoms, or a cyclic alkyl group comprising 3 to 6 carbon atoms, or $R^6$ and $R^7$ are combined to form an alkylene group comprising 3 to 6 carbon atoms; or 2) when n is 1 or 2, $R^5$, $R^6$, $R^7$, $R^8$, $R^9$, and $R^{10}$ are each independently a hydrogen atom, a linear alkyl group comprising 1 to 6 carbon atoms, a branched alkyl group comprising 3 to 6 carbon atoms, or a cyclic alkyl group comprising 3 to 6 carbon atoms; and A and B are each independently an oxygen atom or a sulfur atom, wherein A and B are not both a sulfur atom.

2. A polymer obtained by polymerizing a monomer mixture comprising an acrylic ester derivative according to claim 1.

3. A photoresist composition containing the polymer according to claim 2.

4. A process for producing an acrylic ester derivative according to claim 1, the process comprising:

reacting a cyclic alcohol of Formula (II):

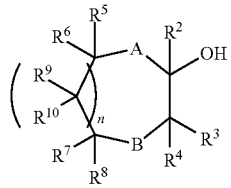

(II)

with a polymerizable group-introducing agent having a formula selected from the group consisting of:

$CH_2=CR^1COX^1$, wherein $X^1$ is a chlorine, bromine, or iodine atom;

$(CH_2=CR^1CO)_2O$;

$CH_2=CR^1COOC(=O)R^{15}$, wherein $R^{15}$ is a t-butyl or 2,4,6-tricholorophenyl; and $CH_2=CR^1COOSO_2R^{16}$, wherein $R^{16}$ is a methyl or p-tolyl, in the presence of a basic substance.

5. The acrylic ester derivative according to claim 1, wherein, in Formula (I):

A is an oxygen atom; and $R^4$ is a hydrogen atom.

6. The acrylic ester derivative according to claim 1, wherein, in formula (I):

n is 0 or 1; and $R^2$, $R^3$, $R^4$, $R^5$, $R^6$, $R^7$, $R^8$, $R^9$, and $R^{10}$ are a hydrogen atom or methyl.

7. A process for producing an acrylic ester derivative according to claim 5, the process comprising:

reacting a cyclic olefin. of Formula (III):

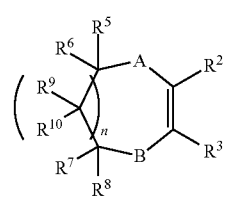

(III)

wherein:

A is an oxygen atom; and

B is an oxygen atom or a sulfur atom, with acrylic acid, methacrylic acid, or 2-trifluoromethylacrylic acid.

* * * * *